(12) United States Patent
Chen et al.

(10) Patent No.: US 12,421,499 B2
(45) Date of Patent: Sep. 23, 2025

(54) METHOD OF DIFFERENTIATION OF HUMAN PLURIPOTENT STEM CELLS TO MONOHORMONAL CELLS

(71) Applicant: Cornell University, Ithaca, NY (US)

(72) Inventors: Shuibing Chen, Pelham, NY (US); Sadaf Amin, New York, NY (US)

(73) Assignee: Cornell University, Ithaca, NY (US)

( * ) Notice: Subject to any disclaimer, the term of this patent is extended or adjusted under 35 U.S.C. 154(b) by 1133 days.

(21) Appl. No.: 17/054,633

(22) PCT Filed: May 10, 2019

(86) PCT No.: PCT/US2019/031805
§ 371 (c)(1),
(2) Date: Nov. 11, 2020

(87) PCT Pub. No.: WO2019/217875
PCT Pub. Date: Nov. 14, 2019

(65) Prior Publication Data
US 2021/0071146 A1    Mar. 11, 2021

Related U.S. Application Data

(60) Provisional application No. 62/670,451, filed on May 11, 2018.

(51) Int. Cl.
C12N 5/071 (2010.01)
(52) U.S. Cl.
CPC ........ C12N 5/0676 (2013.01); *C12N 2510/00* (2013.01)
(58) Field of Classification Search
CPC ................ C12N 5/0676; C12N 2510/00
See application file for complete search history.

(56) References Cited

U.S. PATENT DOCUMENTS

| | | |
|---|---|---|
| 7,776,597 B2 | 8/2010 | Deng et al. |
| 9,540,613 B2 | 1/2017 | Odorico et al. |
| 10,344,264 B2 | 7/2019 | Rezania |
| 10,457,916 B2 | 10/2019 | Kume et al. |
| 2011/0112015 A1 | 5/2011 | Julier et al. |
| 2014/0234963 A1 | 8/2014 | Funa et al. |
| 2015/0218522 A1* | 8/2015 | Peterson ............. C12N 5/0696 |
| 2015/0376574 A1 | 12/2015 | Talavera-Adame et al. |
| 2017/0029778 A1 | 2/2017 | Peterson et al. |
| 2017/0362572 A1 | 12/2017 | Rieck et al. |
| 2018/0327719 A1 | 11/2018 | Osafune et al. |
| 2019/0169575 A1 | 6/2019 | Peterson et al. |
| 2019/0292523 A1 | 9/2019 | Rezania |
| 2019/0338250 A1 | 11/2019 | Melton et al. |

FOREIGN PATENT DOCUMENTS

| | | |
|---|---|---|
| WO | 2017205511 A1 | 11/2017 |
| WO | 2019/169351 A1 | 9/2019 |
| WO | 2019/222487 A1 | 11/2019 |

OTHER PUBLICATIONS

Metzger, D. E., et al., "Grg3/TLE3 and Grg1/TLE1 induce monohormonal pancreatic B-cells while repressing α-cell functions," Diabetes 63(5): 1804-1816. doi: 10.2337/db13-0867. (Year: 2014).*
Arora, M., "Cell Culture Media: A Review," Mater. Methods. 2013;3:175. doi.org/10.13070/mm.en.3.175. (Year: 2013).*
Scoville, D. W., et al., "GLIS1-3: emerging roles in reprogramming, stem and progenitor cell differentiation and maintenance," Stem Cell Investig. 4:80. doi: 10.21037/sci.2017.09.01. (Year: 2017).*
Karimova et al., "Overcoming the Limitations of Stem Cell-Derived Beta Cells," Biomolecules 12(6): 810. doi: 10.3390/biom12060810. (Year: 2022).*
Kumar, S.S., et al., Recent Developments in β-Cell Differentiation of Pluripotent Stem Cells Induced by Small and Large Molecules, International Journal of Molecular Sciences, Dec. 17, 2014, vol. 15, Issue 12, pp. 23418-23447.
Rezania, A., et al., Reversal of diabetes with insulin-producing cells derived in vitro from human pluripotent stem cells, Nature Biotechnology, Sep. 11, 2014, vol. 21, pp. 1121-1133.
Ma, X., et al., Chemical strategies for pancreatic β cell differentiation, reprogramming, and regeneration, Acta Biochimica et Biophysica Sinica, Feb. 22, 2017, vol. 49, Issue 4, pp. 289-301.
Kunisada, Y., et al., Small molecules induce efficient differentiation into insulin-producing cells from human induced pluripotent stem cells, Stem Cell Research, Mar. 2012, vol. 8, Issue 2, pp. 274-284.
Pagliuca, F.W., et al., Generation of Functional Human Pancreatic Beta Cells In Vitro, Cell, Oct. 9, 2014, vol. 159, pp. 428-439.
Wang, Q., et al., Real-time observation of pancreatic beta cell differentiation from human induced pluripotent stem cells, Am J Transl Res, Jun. 15, 2019, vol. 11, No. 6, pp. 3490-3504.
Shahjalal, H., et al., Generation of insulin-producing beta-like cells from human iPS cells in a defined and completely xeno-free culture system, Journal of Molecular Cell Biology, Oct. 2014, vol. 6, No. 5, pp. 394-408.
Yabe, S.G., et al., Efficient generation of functional pancreatic beta-cells from human induced pluripotent stem cells, Journal of Diabetes, Feb. 2017, vol. 9, No. 2, pp. 168-179.

* cited by examiner

*Primary Examiner* — Tracy Vivlemore
*Assistant Examiner* — Eric J Rogers
(74) *Attorney, Agent, or Firm* — Hodgson Russ LLP

(57) ABSTRACT

Compositions and methods are provided for generation of a population of monohormonal from human pluripotent cells. The method comprises sequentially exposing pluripotent stem cells to medium comprising CHIR99021 and Activin A; medium comprising Activin A; medium comprising FGF7; medium comprising retinoic acid, LDN193189, SANT1; medium comprising retinoic acid, LDN193189, SANT1, EGF and FGF2; and differentiation medium. A majority of cells in the population are monohormonal cells produce insulin, but not glucagon, somatostatin or ghrelin.

4 Claims, 47 Drawing Sheets
Specification includes a Sequence Listing.

g
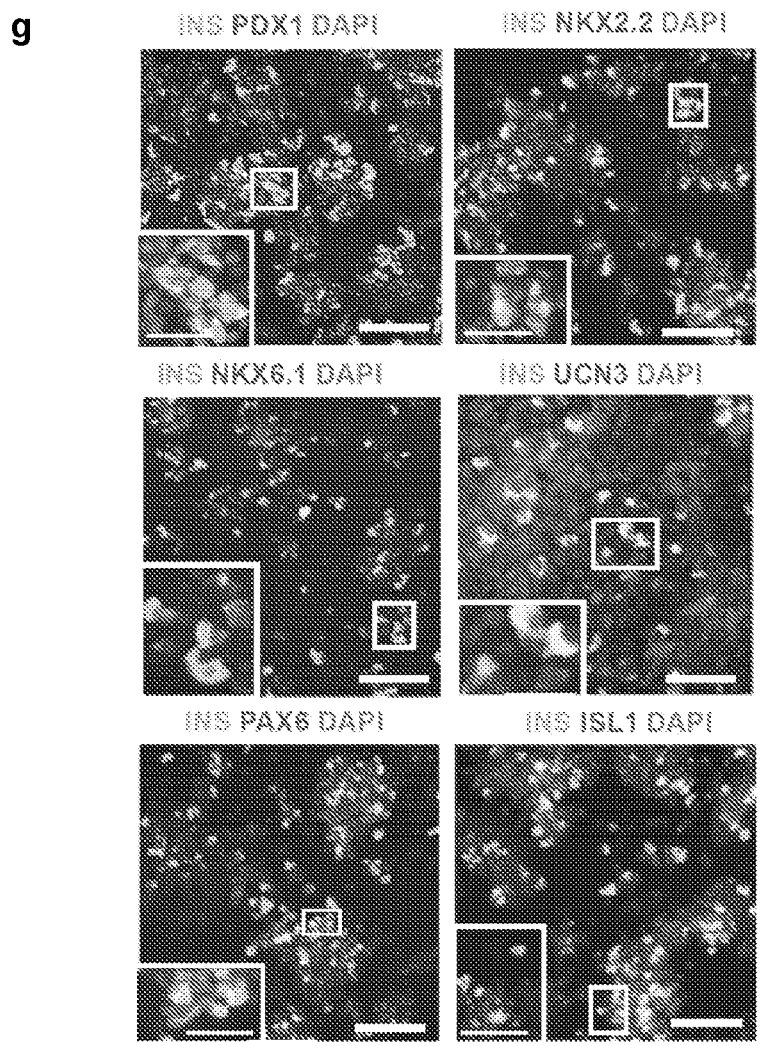
h
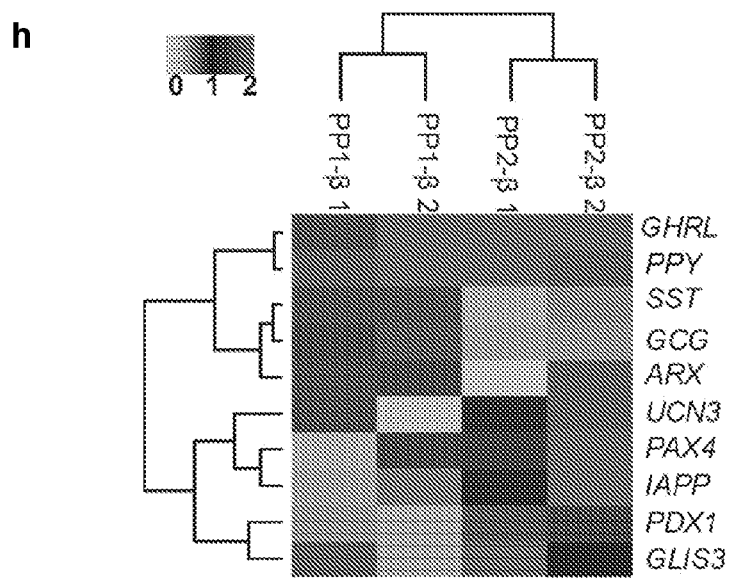
Fig. 1 (cont.)

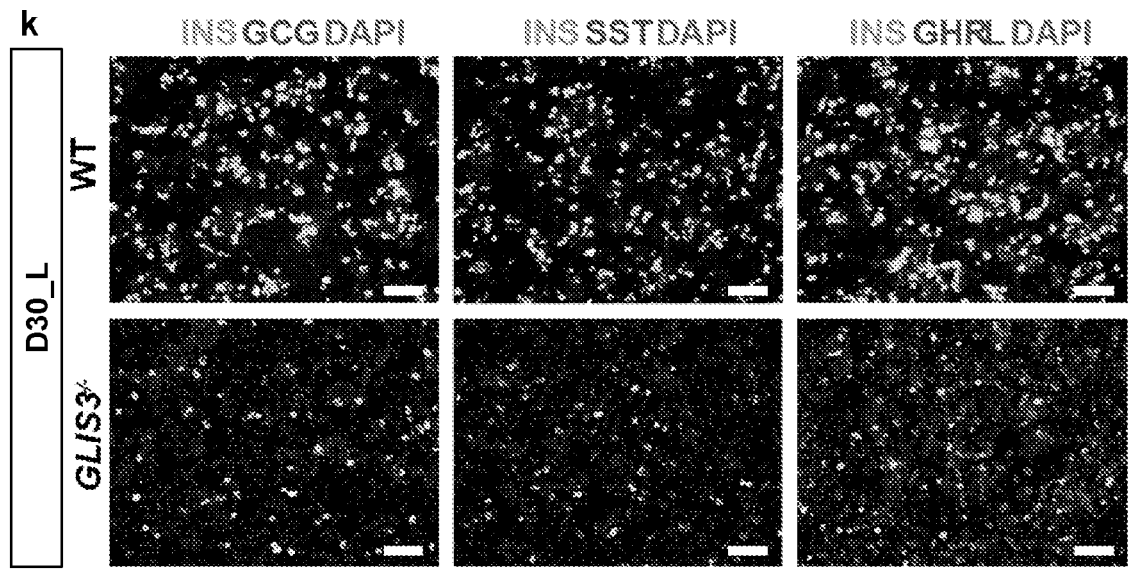
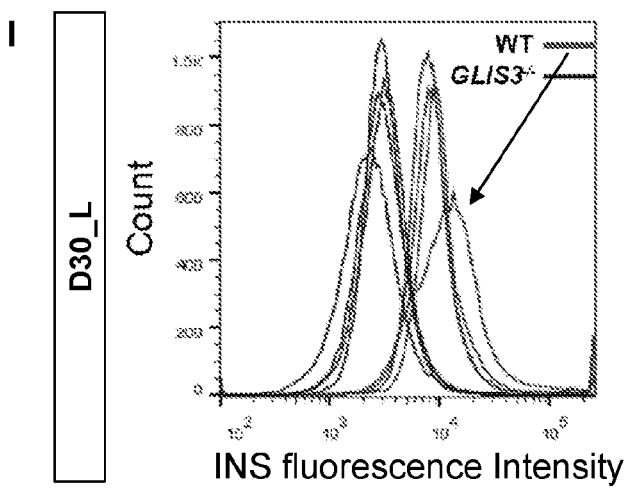
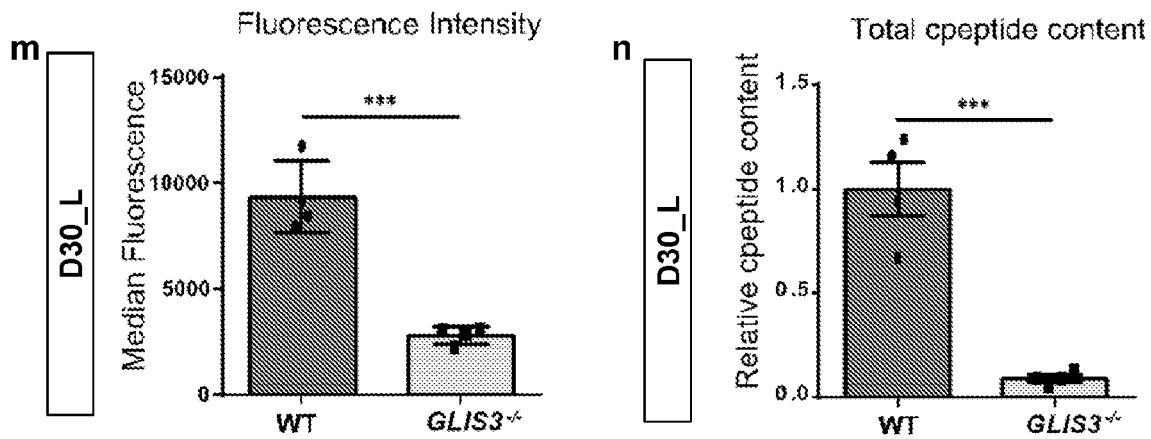
Fig. 2 (cont.)

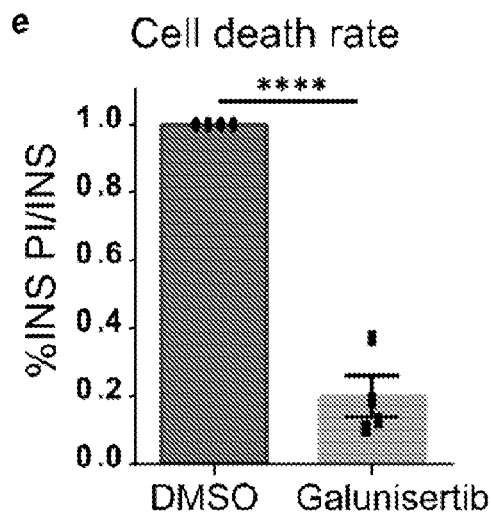
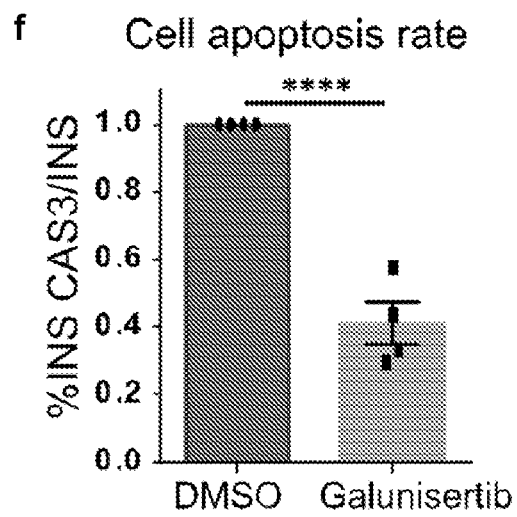
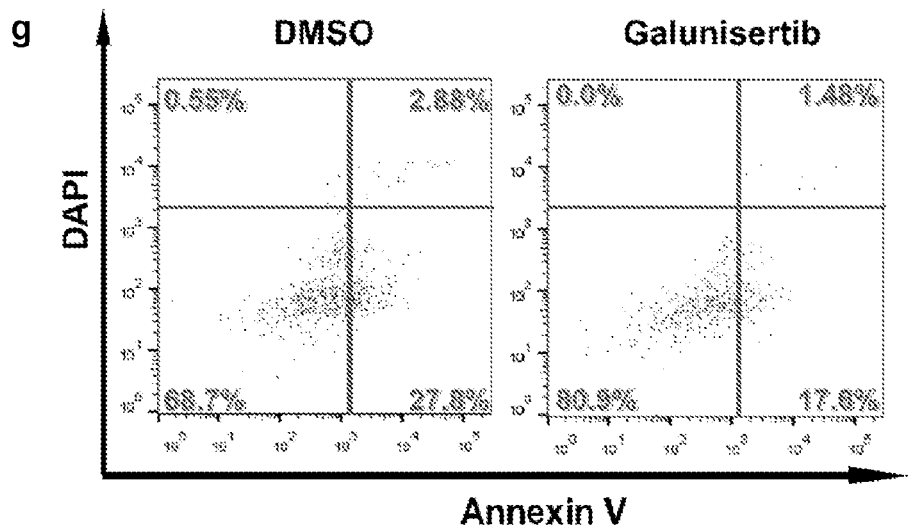
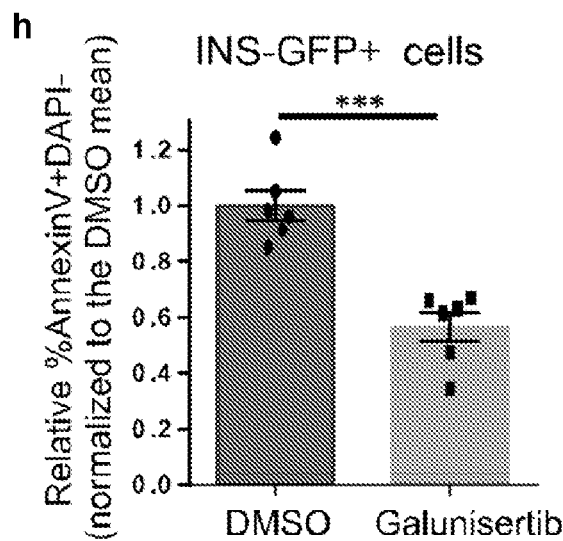
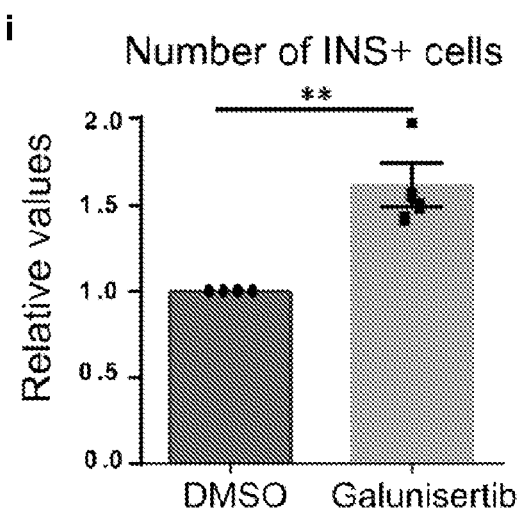
Fig. 4 (cont.)

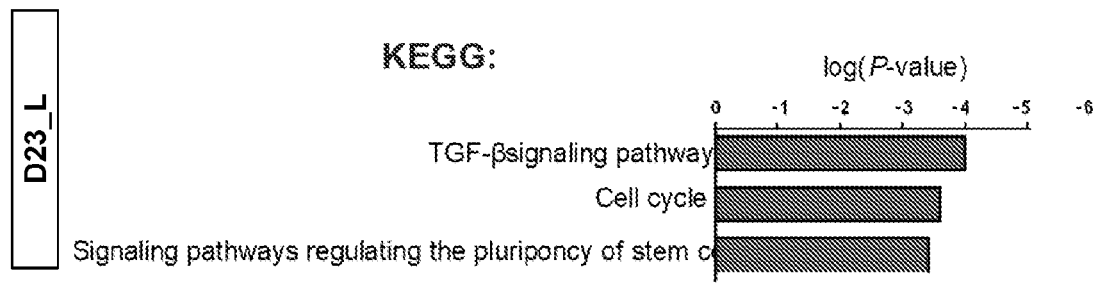
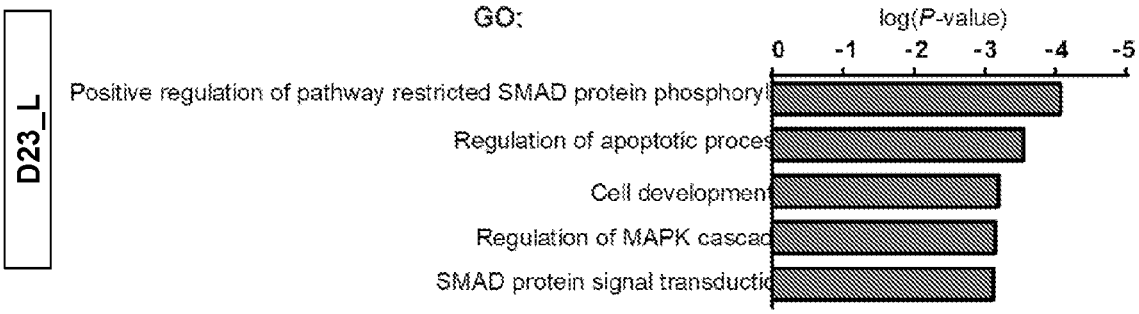
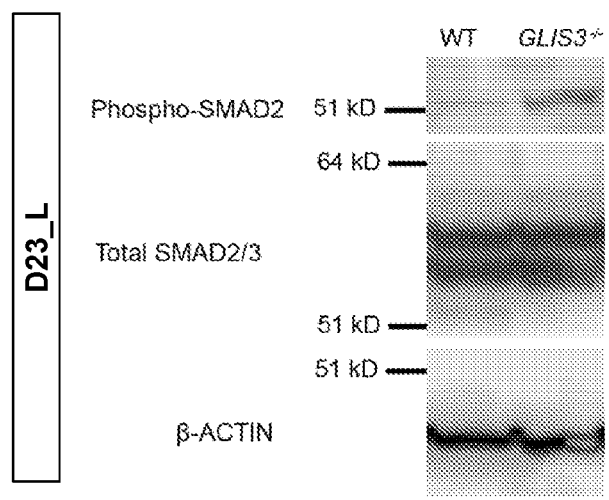
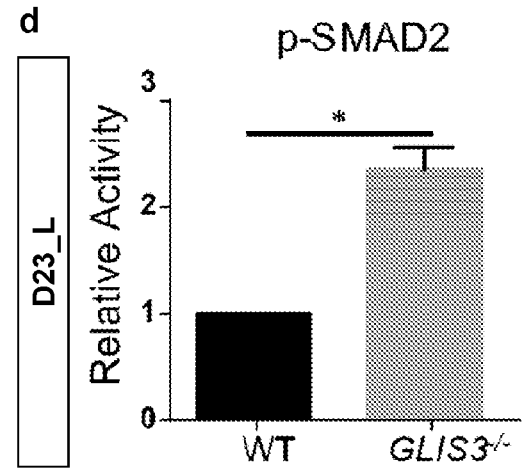
Fig. 5

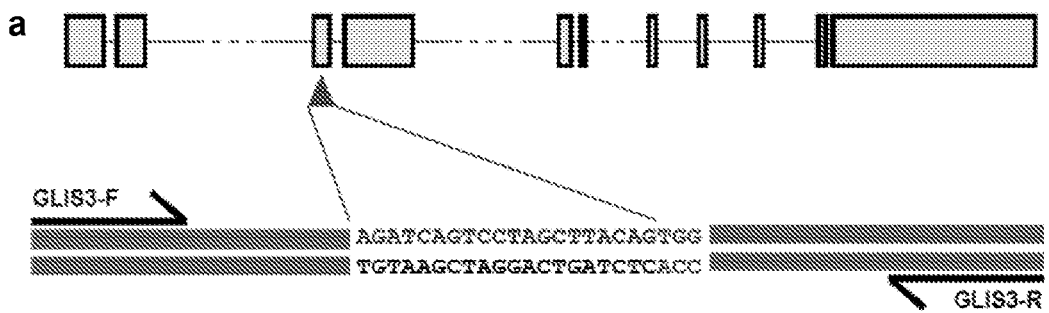
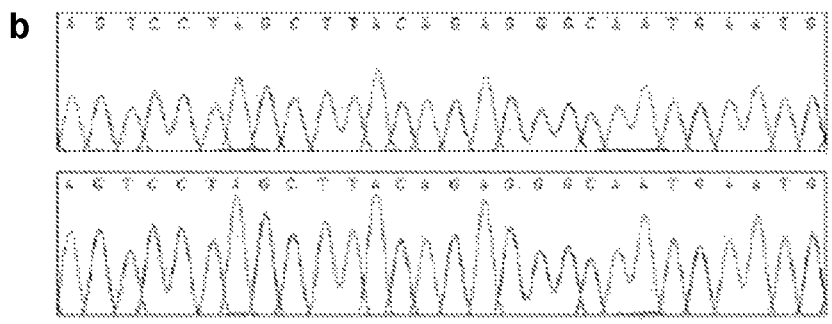
GLIS3+/+-2 (WT2)   AGTCCTAGCTTACAGAGGGCAATGAATG
GLIS3+/+-7 (WT7)   AGTCCTAGCTTACAGAGGGCAATGAATG
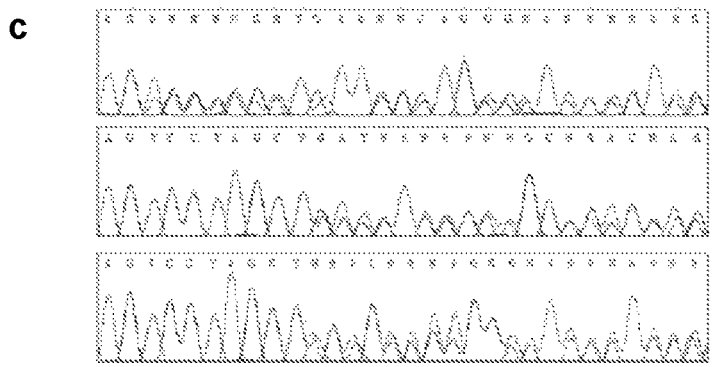
```
                        S179fs/Q183fs
GLIS3-/--22 (KO22)   AG--------------AGGGCAATGAATG
                     AGTCCTAGCTTAACAGAGGGCAATGAATG
                        L182fs/Q183fs
GLIS3-/--28 (KO28)   AGTCCTAGCT-------GGTGAAGAATG
                     AGTCCTAGCTTACA----------AATG
                        L182fs/L182fs
GLIS3-/--29 (KO29)   AGTCCTAGCTTAACAGAGGGCAATGAATG
                     AGTCCTAGCTAGTCCAGAGGGCAATGAATG
```
Fig. 7

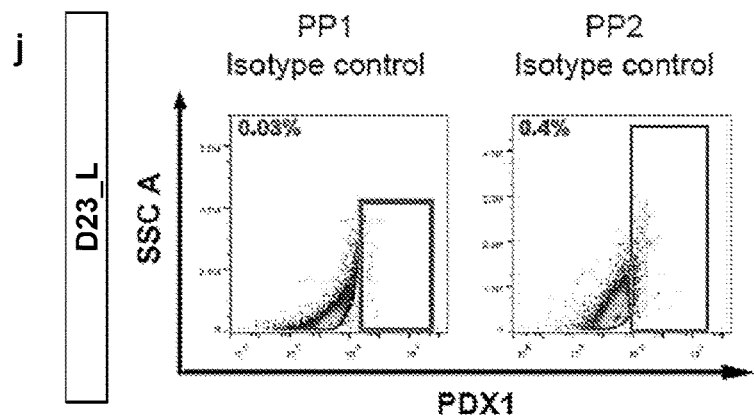
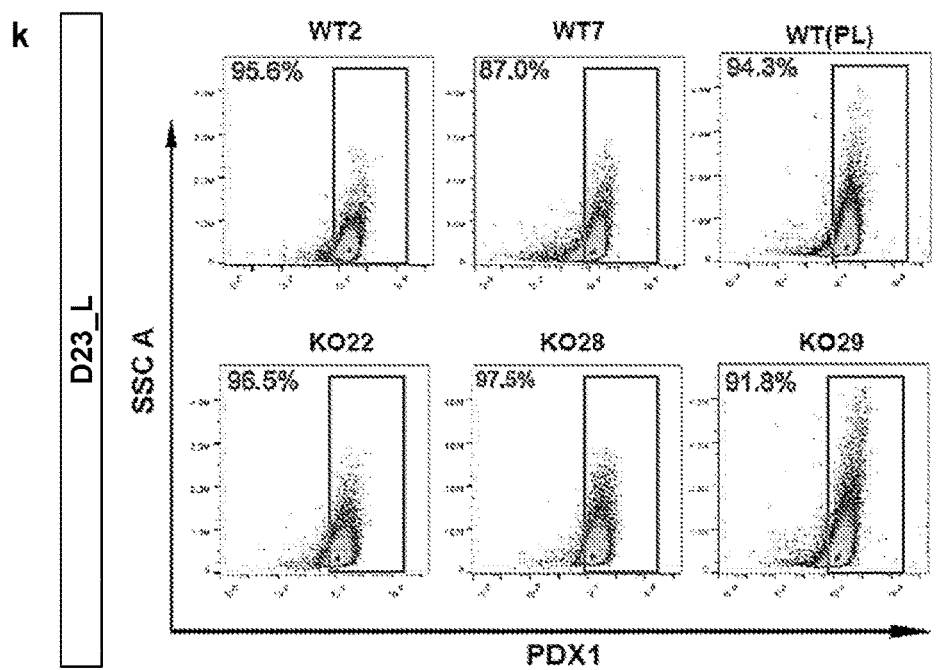
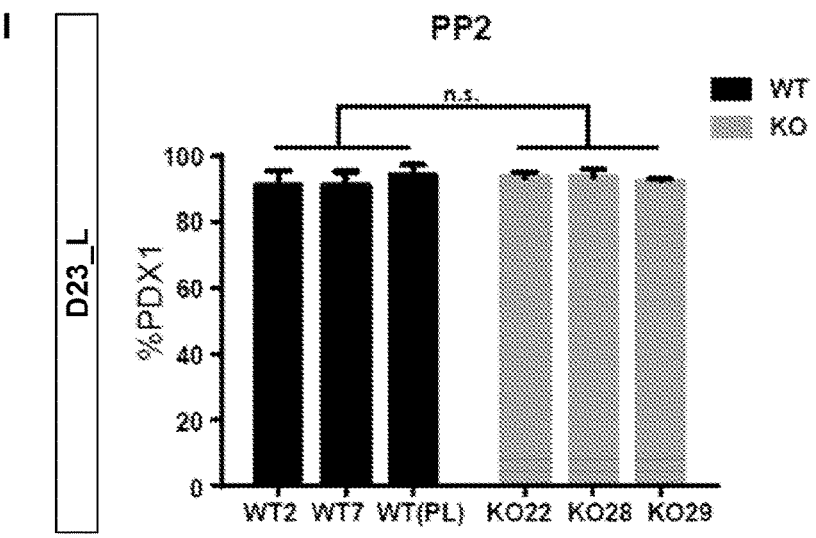
Fig. 7 (cont.)

a
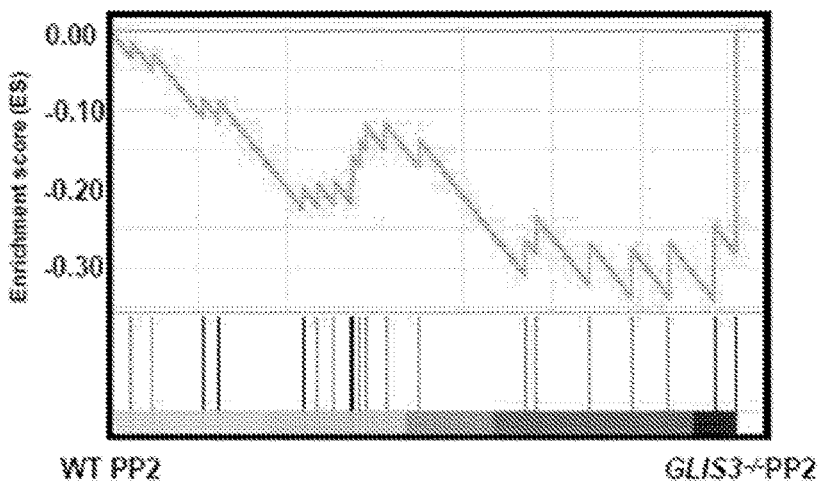
b
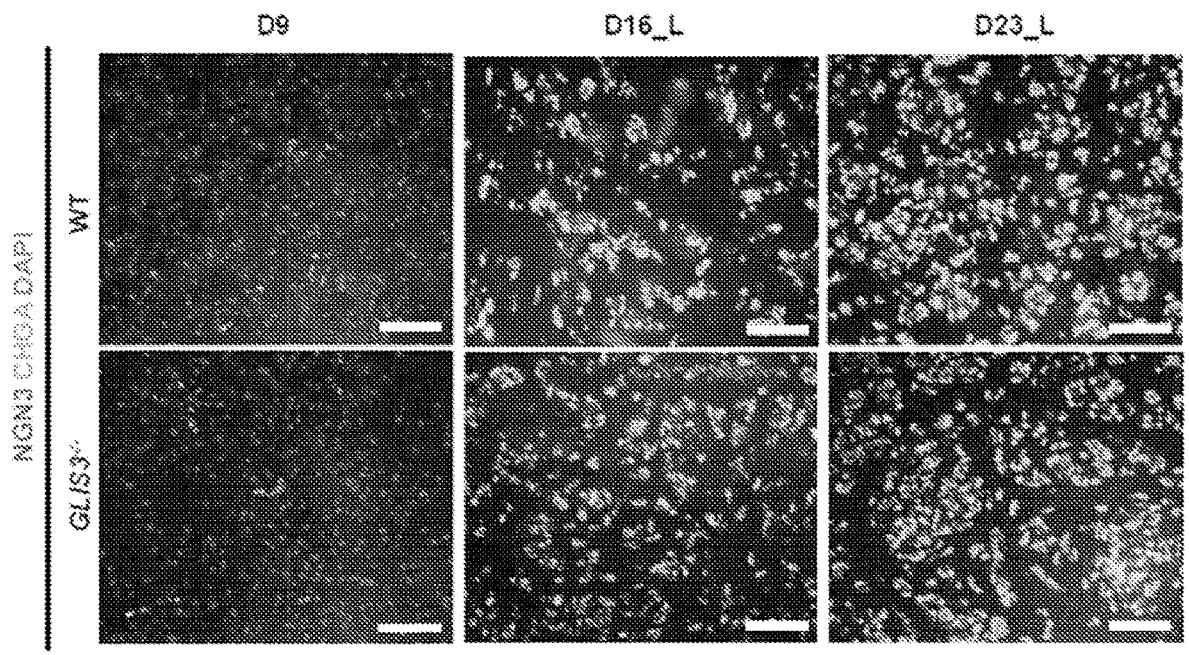
Fig. 8

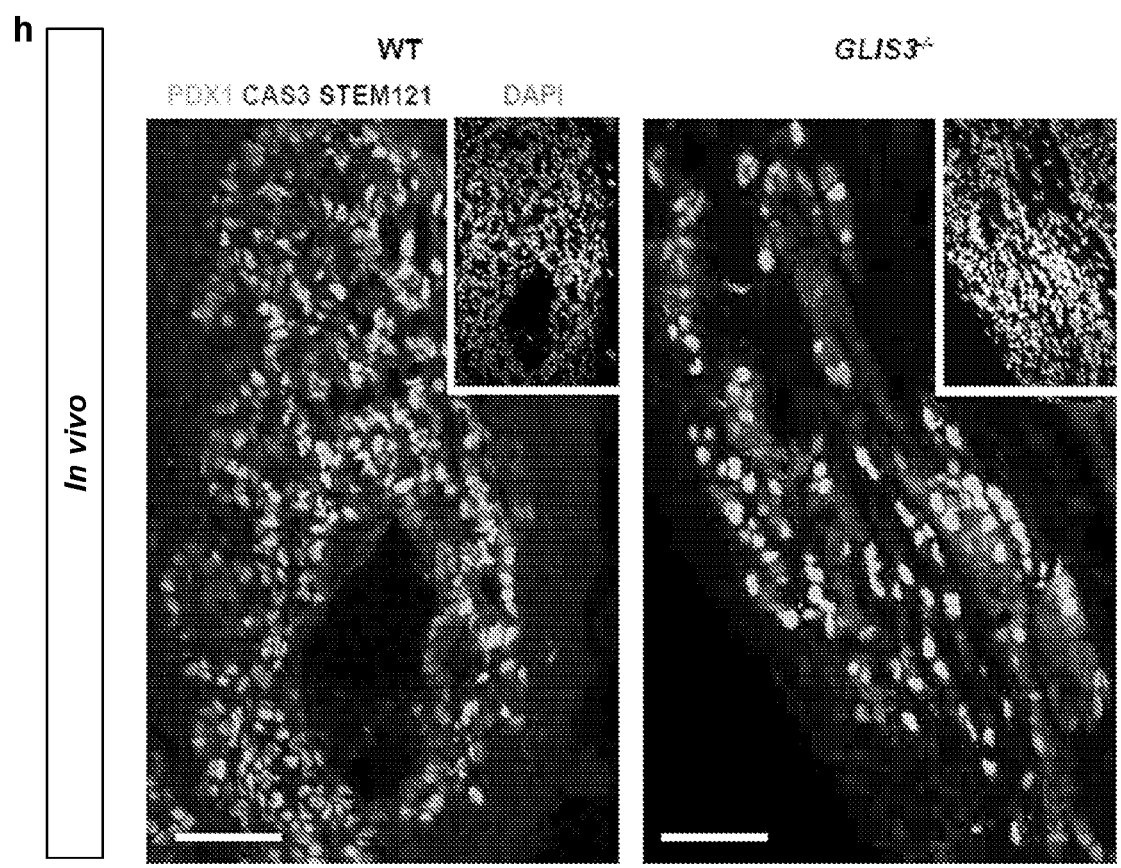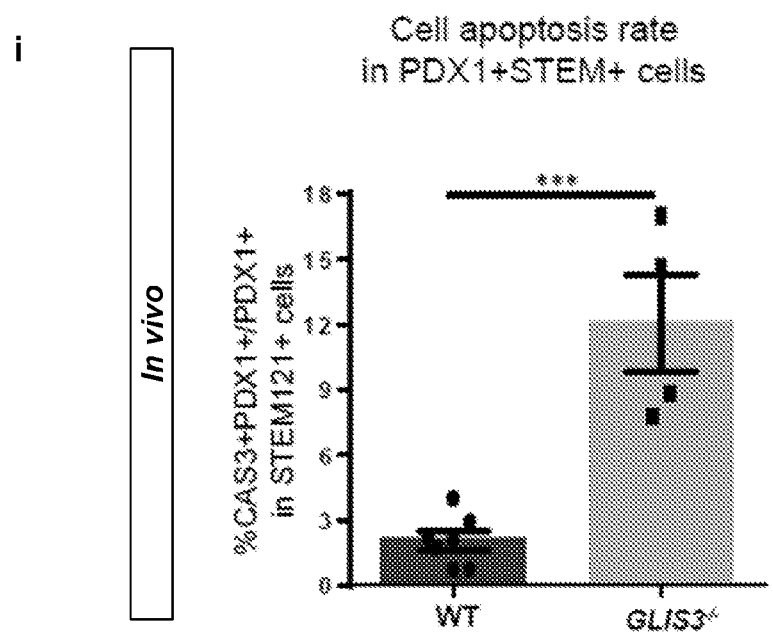
Fig. 10 (cont.)

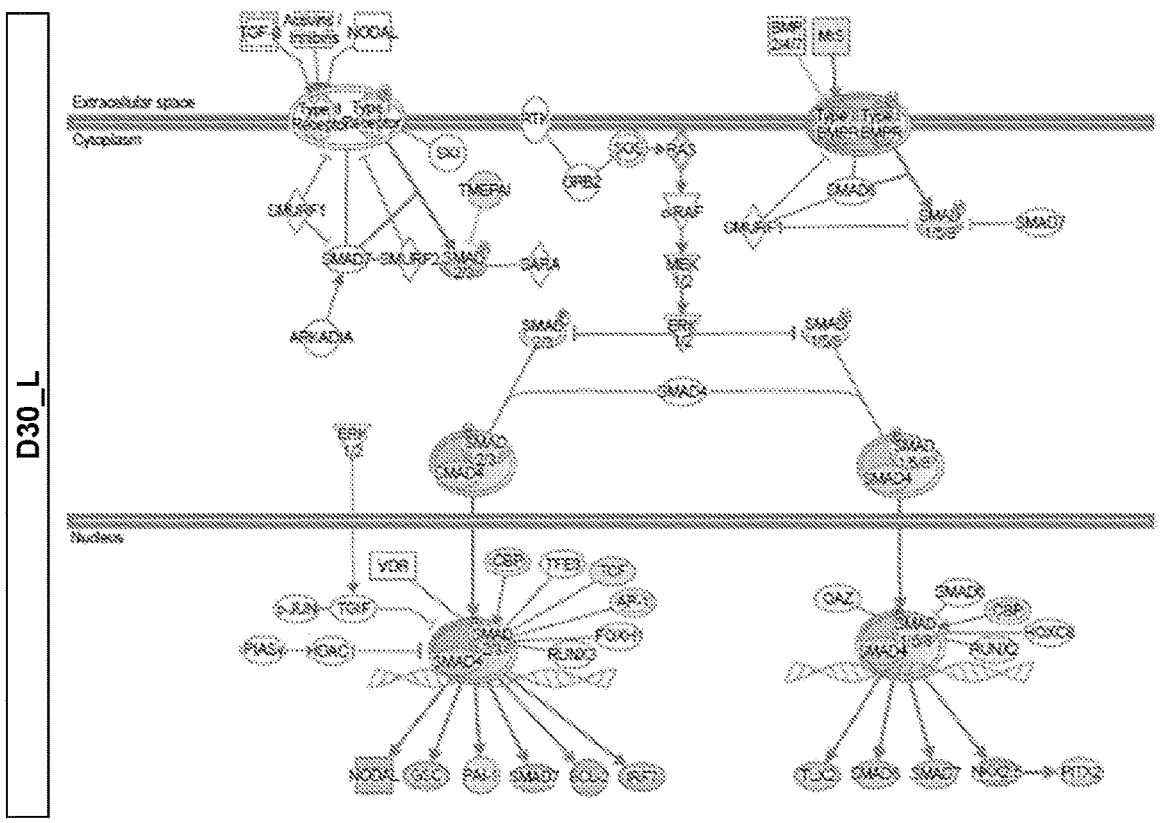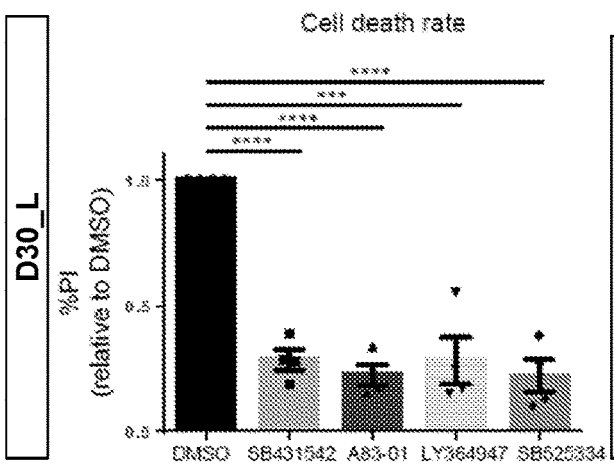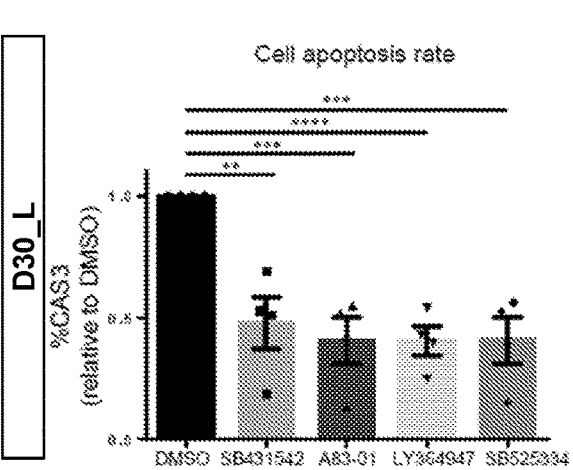
Fig. 14 (cont.)

Table 1. Definition of differentiation stage and cells.

| Stage | Cells |
|---|---|
| D9/day 9 | PP1 cells |
| D16_E/day 16 using the early progenitor protocol | PP2 cells |
| D23_L/day 23 using the late progenitor protocol | INS-GFP$^+$ cells were defined as PP1-β cells |
| D30_L/day 23 using the late progenitor protocol | INS-GFP$^+$ cells were defined as PP2-β cells |

Fig. 16

Table 2. QRT-PCR primers.

| Gene | | Primer Sequence (5'-3') |
|---|---|---|
| ACTB | F | CAATGTGGCCGAGGACTTTG (SEQ ID NO:14) |
| | R | CATTCTCCTTAGAGAGAAGTGG (SEQ ID NO:15) |
| PDX1 | F | CCTTTCCCATGGATGAAGTC (SEQ ID NO:16) |
| | R | CGTCCGCTTGTTCTCCTC (SEQ ID NO:17) |
| NKX6.1 | F | TCGTTTGGCCTATTCGTTGG (SEQ ID NO:18) |
| | R | TGTCTCCGAGTCCTGCTTC (SEQ ID NO:19) |
| NEUROD1 | F | ATGACCAAATCGTACAGCGAG (SEQ ID NO:20) |
| | R | GTTCATGGCTTCGAGGTCGT (SEQ ID NO:21) |
| MAFA | F | CTTCAGCAAGGAGGAGGTCATC (SEQ ID NO:22) |
| | R | CTCGTATTTCTCCTTGTACAGGTCC (SEQ ID NO:23) |
| GLIS3 | F | GACTCACTCGGGCATTACAG (SEQ ID NO:24) |
| | R | TCCACGGTGCTGATCTGCAAG (SEQ ID NO:25) |
| UCN3 | F | CCCACAAGTTCTACAAAGCCA (SEQ ID NO:26) |
| | R | TCCCGAAGAGGCGTCTCTG (SEQ ID NO:27) |

Fig. 17

Table 3. hPSCs used in the study.

| hPSC line | Source |
|---|---|
| INS[w/GFP] HES3 | Stanley lab at Monash University |
| HUES8 | Harvard University |
| H1 | WiCell Research Institute |

Fig. 18

Table 4. CRISPR sgRNA sequences.

| Gene | sgRNA Sequence (5'-3') | |
|---|---|---|
| GLIS3-CRISPR-1 | F | CACCGTCCCATGATGGTTCAGCGAC (SEQ ID NO:28) |
| | R | AAACGTCGCTGAACCATCATGGGAC (SEQ ID NO:29) |
| GLIS3-CRISPR-2 | F | CACCGAGATCAGTCCTAGCTTACAG (SEQ ID NO:30) |
| | R | AAACCTGTAAGCTAGGACTGATCTC (SEQ ID NO:31) |

Fig. 19

Table 5. PCR and sequencing primers used for genotyping the knockout hESC lines.

| Gene | Primer Sequence (5'-3') | |
|---|---|---|
| GLIS3-seq | F | GGGTCCTGATATAAGCGTGC (SEQ ID NO:32) |
| | R | TCACTCACACCACAAGACAGT (SEQ ID NO:33) |

Fig. 20

Table 6. Efficiency for the creation of biallelic knockout hESC lines.

| Gene | Sequenced Subclones | Monoallelic knockout clones | Biallelic knockout clones | Biallelic knockout efficiency |
|---|---|---|---|---|
| GLIS3 | 30 | 2 | 24 | 80% |

Fig. 21

Table 7. Clonal lines used for each experiment.

| Figure | WT lines used | KO lines used |
| --- | --- | --- |
| 2A | WT(PL)*, WT2 | KO28, KO29 |
| 2A-MAFA | WT2, WT7, WT(PL) | KO22, KO28, KO29 |
| 2B | WT(PL), WT2 | KO28, KO29 |
| 2C | WT(PL) | KO29 |
| 2D, 2E | WT(PL), WT2 | KO28, KO29 |
| 2F, 2G | WT2, WT7 | KO22, KO28, KO29 |
| 2H-2J | WT2, WT7, WT(PL) | KO22, KO28, KO29 |
| 2K | WT2 | KO22 |
| 2L, 2M | WT2, WT7, WT(PL) | KO22, KO28, KO29 |
| 2N | WT2, WT7, WT(PL) | KO22, KO29 |
| 3A | WT2, WT7, WT(PL) | KO22, KO28, KO29 |
| 3B | WT2 | KO29 |
| 3C | WT7 | KO29 |
| 3D | WT2 | KO22 |
| 3E | WT2, WT7 | KO22, KO28, KO29 |
| 3F | WT2, WT7 | KO22, KO28, KO29 |
| 3G | WT(PL) | KO29 |
| 3H | WT2, WT7, WT(PL) | KO22, KO28, KO29 |
| 3I-3L | WT2 | KO29 |
| 4C | - | KO29 |
| 4D | - | KO22 |
| 4E, 4F | - | KO22, KO28, KO29 |

Fig. 22

| Figure | WT lines used | KO lines used |
|---|---|---|
| 4G | - | |
| 4H, 4I | - | KO22, KO28, KO29 |
| 4J-4M | - | KO29 |
| 5A, 5B | WT(PL), WT2 | KO28, KO29 |
| 5C, 5D | WT2 | KO22 |
| 5E | WT2, WT(PL) | KO28, KO29 |
| 5F, 5G | - | KO22 |
| 5H, 5I | - | KO22, KO28, KO29 |
| S2A-S2L | WT2, WT7, WT(PL) | KO22, KO28, KO29 |
| S3A | WT(PL), WT2 | KO28, KO29 |
| S3B-S3F | WT2, WT7 | KO22, KO28, KO29 |
| S3G, S3H | WT2 | KO29 |
| S3I | WT2, WT7 | KO22, KO28, KO29 |
| S4A, S4C, S4E | WT2, WT7 | KO22, KO28, KO29 |
| S4B, S4D, S4F | WT2, WT7, WT(PL) | KO22, KO28, KO29 |
| S4G, S4H | WT2, WT7 | KO22, KO28, KO29 |
| S4I, S4J | WT2, WT7 | KO22, KO28, KO29 |
| S4K | WT2 | KO29 |
| S4L, S4M | WT2, WT7, WT(PL) | KO22, KO28, KO29 |
| S5A | WT2 | KO22 |
| S5B | WT2, WT7 | KO22, KO28, KO29 |
| S5C | WT2 | KO29 |
| S5D | WT2, WT7 | KO22, KO28, KO29 |
| S5E | WT2 | KO22 |

Fig. 22 (cont.)

| Figure | WT lines used | KO lines used |
|---|---|---|
| S5F, S5G | WT2, WT7 | KO22, KO28, KO29 |
| S5H, S5I | WT2 | KO29 |
| S6A | WT2, WT7 | KO22, KO28, KO29 |
| S6C | WT2 (control wells) | KO29 |
| S7A | WT2 | - |
| S7B | WT2, WT7, WT(PL) | - |
| S8A, S8B | - | KO22, KO28, KO29 |
| S8C, S8D | - | KO29 |
| S8E, S8F | - | KO22, KO28, KO29 |
| S9A | WT2, WT(PL) | KO28, KO29 |
| S9B | WT2 | KO29 |
| S9C | WT2, WT(PL) | KO28, KO29 |

Fig. 22 (cont.)

Table 8. Top hit compounds from the drug screening. Z-scores were calculated for the cleaved caspase-3 percentage using the formula $Z=(x-\mu)/\sigma$.

| Compound name | Z-score | Bioactivity |
|---|---|---|
| SB-525334 | -2.33797 | TGF-β RI Kinase Inhibitor VIII |
| LY2157299 (Galunisertib) | -2.2971 | TGF-β RI Kinase Inhibitor |
| Protriptyline HCl | -2.26557 | Norepinephrine uptake blocker |
| Suxibuzone | -2.15349 | Analgesic, Anti-inflammatory |
| A83-01 | -2.14045 | TGF-beta RI Inhibitor IV |
| (±)-Ibuprofen | -2.13479 | COX inhibitor, Anti-inflammatory |
| Hesperetin | -2.12035 | P450 inhibitor |
| PD169316 | -1.97457 | P38 MAPK inhibitor |
| Betamethasone Valerate | -1.88811 | Glucocorticoid |
| Ambroxol HCl | -1.85367 | Expectorant |
| LY 364947 | -1.59577 | ALK5 Inhibitor I TGF-β RI Kinase Inhibitor |

Fig. 23

Table 9. Summary of TGFβ inhibitors used in Figure 5.

| Compound | Activity |
|---|---|
| SB 431542 | Potent and selective inhibitor of the transforming growth factor-β (TGF-β) type I receptor activin receptor-like kinase ALK5 and its relatives ALK4 and ALK7 |
| A83-01 | Potent inhibitor of TGF-β type I receptor ALK5 kinase, type I activin/nodal receptor ALK4 and type I nodal receptor ALK7.<br>Weak inhibitor of ALK-1, -2, -3, -6 and MAPK activity |
| SB 525334 | Selective inhibitor of transforming growth factor-β receptor I (ALK5, TGF-βRI) |
| LY-364947 | Selective inhibitor of TGF-β type-I receptor (TGF-β RI, TGFR-I, TβR-I, ALK-5) |

Fig. 24

SEQUENCE LISTING

```
<160> NUMBER OF SEQ ID NOS: 33

<210> SEQ ID NO 1
<211> LENGTH: 23
<212> TYPE: DNA
<213> ORGANISM: Homo sapiens

<400> SEQUENCE: 1
agatcagtcc tagcttacag tgg                                              23

<210> SEQ ID NO 2
<211> LENGTH: 23
<212> TYPE: DNA
<213> ORGANISM: Homo sapiens

<400> SEQUENCE: 2
ccactctagt caggatcgaa tgt                                              23

<210> SEQ ID NO 3
<211> LENGTH: 28
<212> TYPE: DNA
<213> ORGANISM: Homo sapiens

<400> SEQUENCE: 3
agtcctagct tacagagggc aatgaatg                                         28

<210> SEQ ID NO 4
<211> LENGTH: 29
<212> TYPE: DNA
<213> ORGANISM: Homo sapiens
<220> FEATURE:
<221> NAME/KEY: misc_feature
<222> LOCATION: (4)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (23)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 4
```
agannnngnt gaanncaggg nannnnang                              29

<210> SEQ ID NO 5
<211> LENGTH: 29
<212> TYPE: DNA
<213> ORGANISM: Homo sapiens
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 5
agtcctagct gatnannnnn gcngacnag                              29

<210> SEQ ID NO 6
<211> LENGTH: 30
<212> TYPE: DNA
<213> ORGANISM: Homo sapiens
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (15)..(17)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (24)..(26)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t

<400> SEQUENCE: 6
agtcctagct nnacnnnagg gnannnannn                             30

<210> SEQ ID NO 7
<211> LENGTH: 13
<212> TYPE: DNA
<213> ORGANISM: Homo sapiens

<400> SEQUENCE: 7
agggcaatga atg                                               13

<210> SEQ ID NO 8
<211> LENGTH: 29
<212> TYPE: DNA
<213> ORGANISM: Homo sapiens

<400> SEQUENCE: 8
gtaagtaacg ggagacaatt cgatcctga                              29

```
<210> SEQ ID NO 9
<211> LENGTH: 10
<212> TYPE: DNA
<213> ORGANISM: Homo sapiens

<400> SEQUENCE: 9
agtcctagct                                                          10

<210> SEQ ID NO 10
<211> LENGTH: 12
<212> TYPE: DNA
<213> ORGANISM: Homo sapiens

<400> SEQUENCE: 10
ggtgaagaaa tg                                                       12

<210> SEQ ID NO 11
<211> LENGTH: 14
<212> TYPE: DNA
<213> ORGANISM: Homo sapiens

<400> SEQUENCE: 11
acattcgatc ctga                                                     14

<210> SEQ ID NO 12
<211> LENGTH: 29
<212> TYPE: DNA
<213> ORGANISM: Homo sapiens

<400> SEQUENCE: 12
agtcctagct taacagaggg caatgaatg                                     29

<210> SEQ ID NO 13
<211> LENGTH: 30
<212> TYPE: DNA
<213> ORGANISM: Homo sapiens

<400> SEQUENCE: 13
gtaagtaacg ggagacctga tcgatcctga                                    30

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
caatgtggcc gaggactttg                                               20

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
cattctcctt agagagaagt gg                                            22

<210> SEQ ID NO 16
<211> LENGTH: 20
<212> TYPE: DNA
<213> ORGANISM: Artificial Sequence
```

```
<220> FEATURE:
<223> OTHER INFORMATION: primer

<400> SEQUENCE: 16
cctttcccat ggatgaagtc                                              20

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
cgtccgcttg ttctcctc                                                18

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tcgtttggcc tattcgttgg                                              20

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
tgtctccgag tcctgcttc                                               19

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
atgaccaaat cgtacagcga g                                            21

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gttcatggct tcgaggtcgt                                              20

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
cttcagcaag gaggaggtca tc                                           22
```

<210> SEQ ID NO 23
<211> LENGTH: 25
<212> TYPE: DNA
<213> ORGANISM: Artificial Sequence
<220> FEATURE:
<223> OTHER INFORMATION: primer

<400> SEQUENCE: 23
ctcgtatttc tccttgtaca ggtcc                                  25

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
gactcactcg ggcattacag                                        20

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
tccacggtgc tgatctgcaa g                                      21

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
cccacaagtt ctacaaagcc a                                      21

<210> SEQ ID NO 27
<211> LENGTH: 19
<212> TYPE: DNA
<213> ORGANISM: Artificial Sequence
<220> FEATURE:
<223> OTHER INFORMATION: primer

<400> SEQUENCE: 27
tcccgaagag gcgtctctg                                         19

<210> SEQ ID NO 28
<211> LENGTH: 25
<212> TYPE: DNA
<213> ORGANISM: Artificial Sequence
<220> FEATURE:
<223> OTHER INFORMATION: CRISPR sgRNA

<400> SEQUENCE: 28
caccgtccca tgatggttca gcgac                                  25

<210> SEQ ID NO 29
<211> LENGTH: 25
<212> TYPE: DNA
<213> ORGANISM: Artificial Sequence
<220> FEATURE:
<223> OTHER INFORMATION: CRISPR sgRNA -continued

```
<400> SEQUENCE: 29
aaacgtcgct gaaccatcat gggac                                    25

<210> SEQ ID NO 30
<211> LENGTH: 25
<212> TYPE: DNA
<213> ORGANISM: Artificial Sequence
<220> FEATURE:
<223> OTHER INFORMATION: CRISPR sgRNA

<400> SEQUENCE: 30
caccgagatc agtcctagct tacag                                    25

<210> SEQ ID NO 31
<211> LENGTH: 25
<212> TYPE: DNA
<213> ORGANISM: Artificial Sequence
<220> FEATURE:
<223> OTHER INFORMATION: CRISPR sgRNA

<400> SEQUENCE: 31
aaacctgtaa gctaggactg atctc                                    25

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
gggtcctgat ataagcgtgc                                          20

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
tcactcacac cacaagacag t                                        21
```

METHOD OF DIFFERENTIATION OF HUMAN PLURIPOTENT STEM CELLS TO MONOHORMONAL CELLS

CROSS REFERENCE TO RELATED APPLICATIONS

This application claims priority to U.S. Provisional application no. 62/670,451, filed on May 11, 2018, the disclosure of which is incorporated herein by reference.

STATEMENT REGARDING FEDERALLY SPONSORED RESEARCH

This invention was made with government support under Grant DP2DK098093-01 and DP3DK111907-01 awarded by the National Institutes of Health. The government has certain rights in the invention.

BACKGROUND OF THE INVENTION

Human pluripotent stem cells (hPSCs) have been used to generate pancreatic β-cell defects for potential use in diabetes, including maturity-onset diabetes of the young (Teo et al. Stem cell reports 6, 357-367 (2016)) and neonatal diabetes (Shang et al. Diabetes 63, 923-933 (2014); Zhu et al. Cell Stem Cell 18, 755-768 (2016); Shi et al. Cell Stem Cell (2017)). However, populations of cells that are enriched for desired cell types have been difficult to obtain. In particular, it has been difficult to obtain enriched populations of monohormonal pancreatic beta cells.

SUMMARY OF THE DISCLOSURE

This disclosure provides compositions and methods for producing enriched populations of mono-hormonal pancreatic beta cells, such as, for example, enriched populations of cells producing exclusively insulin.

In an aspect, this disclosure provides a method for generation of enriched populations of monohormonal cells from pluripotent stem cells. The method comprises exposing pluripotent stem cells (such as human pluripotent stem cells) sequentially to basal medium supplemented with at least CHIR99021 and Activin A; basal medium supplemented with at least Activin A; basal medium supplemented with at least FGF7; basal medium supplemented with at least retinoic acid, LDN193189, SANT1; basal medium supplemented with at least retinoic acid, LDN193189, SANT1, EGF and FGF2; and then allowing the cells to differentiate in basal differentiation medium to generate enriched population of monohormonal cells (PP2-β), wherein at least a majority of the cells produce insulin, but not glucagon, somatostatin or ghrelin.

BRIEF DESCRIPTION OF THE DRAWINGS

FIGS. 16 to 24 are Tables 1-9.

DETAILED DESCRIPTION OF THE DISCLOSURE

Figure 1:
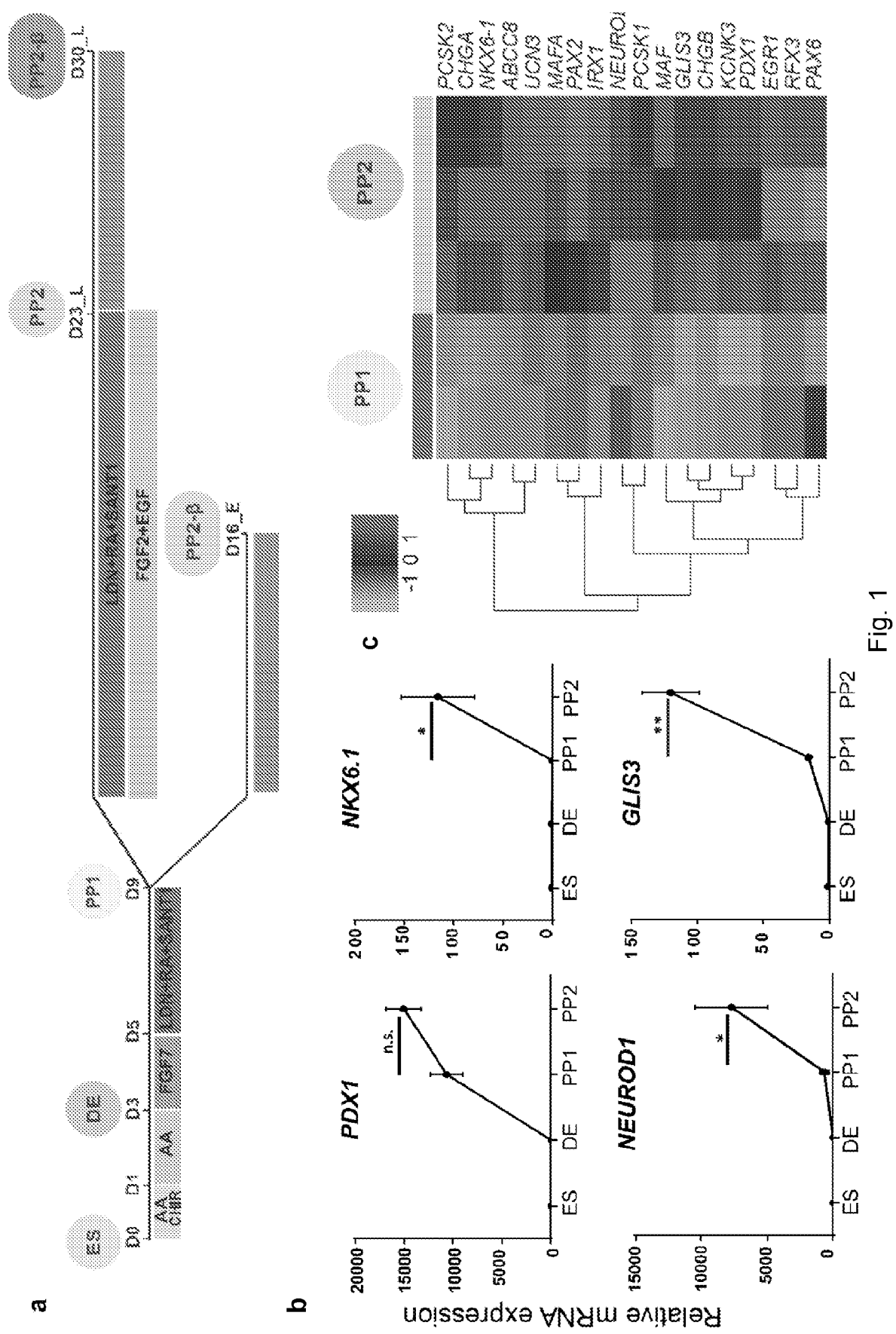
FIG. 1. Generation of mono-hormonal pancreatic β-like cells through the induction of late stage pancreatic progenitors (PP2). (a) Schematic representation of the stepwise differentiation protocol. (b) qRT-PCR analysis of pancreatic progenitor markers in hESCs, definitive endoderm (DE), PP1 and PP2 cells (ES, DE n=3, PP1 n=6, PP2 n=8). (c) Heatmap representing relative expression profiles of genes related to β-cell development in PP1 and PP2 cells (PP1 n=2, PP2 n=3). (d) Immunocytochemistry analysis of insulin (INS) and glucagon (GCG) expression at D16_E and D30_L, insets show a higher magnification image. Scale bar=100 μm. (e, f) Intracellular flow cytometry analysis (e) and quantification (f) of INS and GCG expression at D16_E and D30_L (D16_E n=4, D30_L n=8). (g) Immunocytochemistry analysis of cells at D30_L. Scale bar=100 μm, Scale bar of high magnification insets=40 (h) Heatmap representing the relative expression level of endocrine markers in PP1-β and PP2-β cells. (i) GSEA analysis shows that PP2-β cells are transcriptionally closer to human adult (3 cells than PP1-β cells. The adult β cells_UP and adult β cells_DN gene sets consist of the top 1000 differentially expressed genes (higher expression for UP and lower expression for DN) in primary human β-cells compared to PP1-βcells. (j) FPKM values of GLIS3 in PH-β cells derived using Zhu et al protocol and the purified INS-GFP$^+$ PP1-β (n=4) and PP2-β cells (n=2). (k) Glucose-stimulated c-peptide secretion of cells at D30_L and human islets. The amount of c-peptide secretion in 20 mM (high) D-glucose condition was normalized to the amount of c-peptide secreted in 2 mM (low) D-glucose condition. (n=6 for cells at D30_L and n=10 for islets). (l) Insulin secretion of cells at D30_L in response to other secretagogues, including 30 mM KCl (n=7), 30 μM Forskolin (n=5) or 10 mM Arginine (n=5) relative to basal Krebs-Ringer bicarbonate HEPES (KRBH) buffer treatment (n=7). The fold change was normalized to the amount of c-peptide secreted in KRBH condition. P values by unpaired two-tailed t-test were *P<0.05, P<0.01, *P<0.001, ****P<0.0001. Data are presented as individual biological replicates. The center value is "mean". Error bar is SEM.
Figure 1:
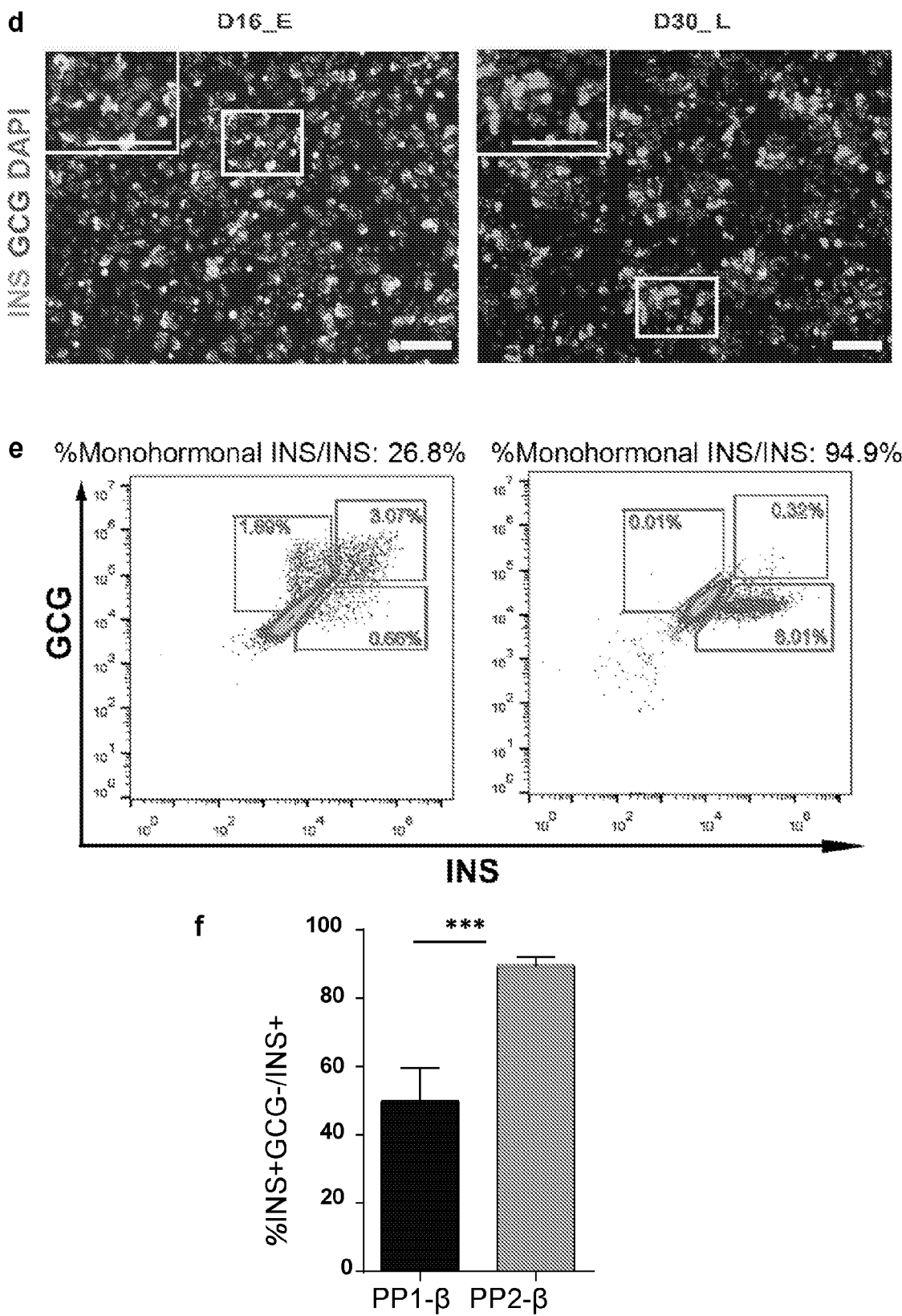
Figure 1:
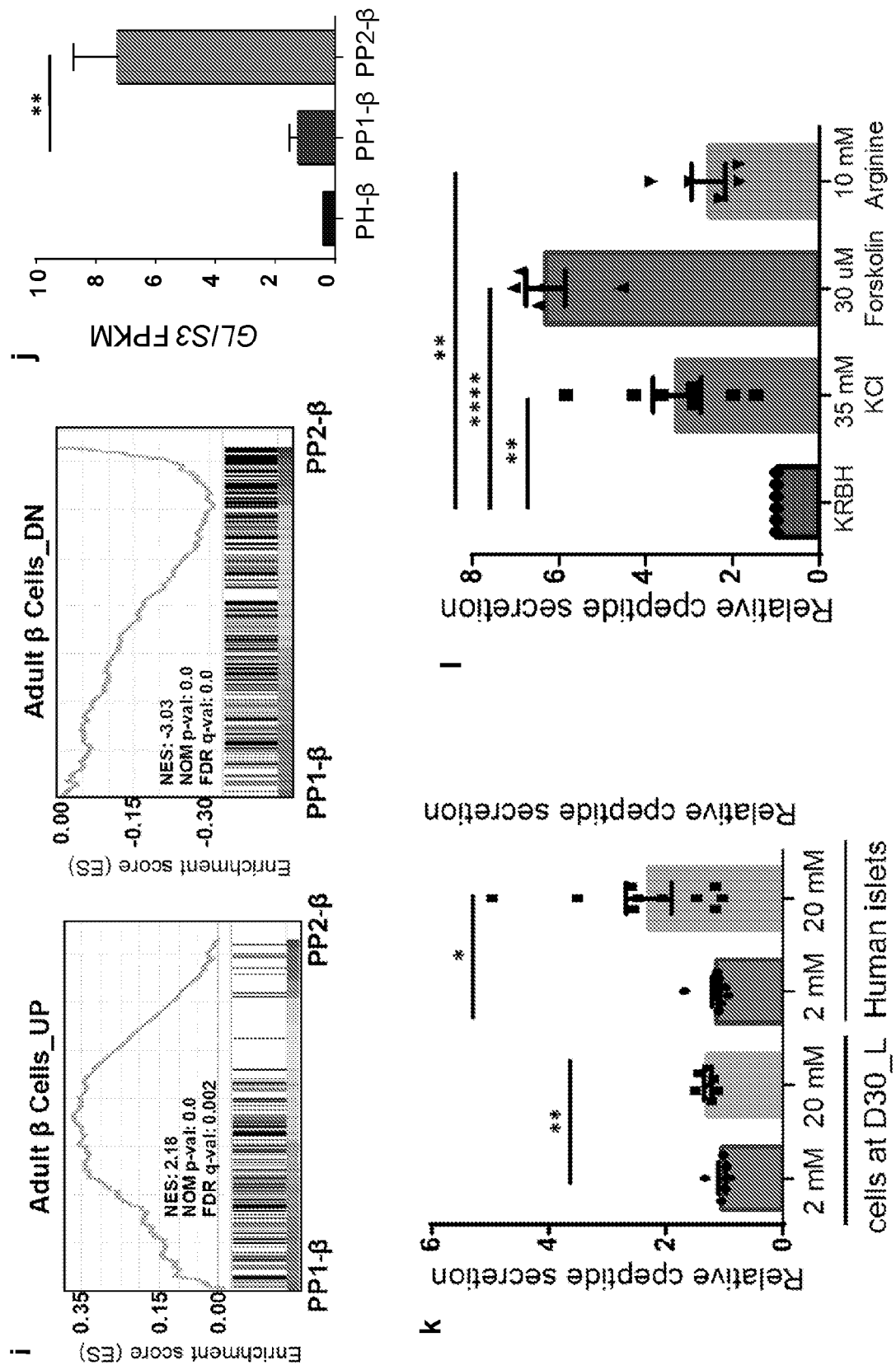

We tested previous protocols for differentiating and generating pancreatic β-cells. We monitored GLIS3 mRNA in hESC-derived pancreatic progenitors and INS+ cells and found that the expression GLIS3 mRNA is not detectable, suggesting that the previous protocol (D'Amour, et al. Nature biotechnology 24, 1392-1401 (2006)) failed to efficiently generate disease relevant cells. In this disclosure, we describe an optimized strategy to efficiently derive GLIS3+ late stage pancreatic progenitors (PP2), which give rise to mono-hormonal pancreatic β-cells (PP2-β cells). The process can also be used for generation of populations enriched in mono-hormonal pancreatic β-cells, which can be used for in vivo implantation (such as in humans afflicted with diabetes). This method and cells can be used to elucidate cellular functions and mechanisms, such as, for example to determine the role of GLIS3 in human pancreatic β-cell generation and survival. The platform can also be used to screen and identify drug candidates for treating the broad range of human patients who suffer from diabetes. Finally, these monohormonal cells can provide an advanced cell population for transplantation therapy of diabetes.

The present disclosure provides a method to generate late stage pancreatic progenitors (PP2 cells) that differentiate to mono-hormonal glucose-responding pancreatic β-like cells (PP2-β cells). In one embodiment, the medium useful in the process for generation of the monohormonal cells comprises, consists essentially of, or consists of RA, an inhibitor of ALK2 and ALK3 (such as LDN193189), smoothened and hedgehog signaling antagonist (SANT1, Abcam), EGF and FGF2.

In one aspect, this disclosure provides populations of cells differentiated from enriched for mono-hormonal pancreatic β-cells (PP2-β cells). In an embodiment, this disclosure provides population of cells produced from stem cells (such as hESCs and human induced pluripotent stem cells/iPSCs) that are enriched for PP2-β cells, which express insulin, but not glucagon. In embodiments, the population of cells may comprise at least 50%, 60%, 70%, 80%, 90%, or 95% monohormonal PP2-β cells.

Compared with PP1, the PP2 cells generated using the compositions and methods of the present disclosure express higher levels of late trunk PP markers, including NKX6.1, and NEUROD1 (as indicated by qRT-PCR assays or RNA-seq profiling). In one embodiment, after a period of differentiation (such as 7 days), at least 85% of INS$^+$ cells derived from PP2 cells can be mono-hormonal, expressing insulin, but not glucagon, somatostatin, or ghrelin. In contrast, when cells are obtained by differentiation of PP1 cells, only 30-40% of INS$^+$ PP1-β cells are mono-hormonal. The majority of the PP2-β cells express insulin, but not glucagon, somatostatin, or ghrelin. The PP2-β cells may co-express mature β-cell markers including one or more of PDX1, NKX2.2, PAX6, ISL1 and NKX6.1. They may also express UCN3, a mature β-cell marker that was not reported as expressed using any of three previously published protocols (Rezania, A. et al. Nature biotechnology 32, 1121-1133 (2014); Pagliuca et al. Cell 159, 428-439 (2014); Russ et al. The EMBO journal 34, 1759-1772 (2015)). Gene set enrichment analysis (GSEA) indicates that PP2-β cells described in this disclosure closely resemble primary adult human β-cells.

Any pluripotent stem cells may be used in the methods of the present disclosure. For example, established lines of pluripotent cells, including pre-embryonic tissue (such as, a blastocyst), embryonic tissue may be used. Other sources include human umbilical cord tissue-derived cells, human amniotic fluid-derived cells, and human placental-derived cells. Examples of cells include established lines of human embryonic stem cells (hESCs) or human embryonic germ cells, such as, the human embryonic stem cell lines H1 (NIH Code: WA01), H7 (NIH Code: WA07), H9 (NIH Code: WA09) (WiCell Research Institute, Madison, Wis., USA), and SA002 (Cellartis AB Corporation, Goteburg, Sweden). Cells that have been taken from a pluripotent stem cell population already cultured in the absence of feeder cells may also be used. Induced pluripotent cells (IPS), or reprogrammed pluripotent cells, derived from adult somatic cells using forced expression of a number of pluripotent related transcription factors, such as OCT4, NANOG, SOX2, KLF4, and ZFP42 (Annu Rev Genomics Hum Genet 2011, 12:165-185; Cell, 126(4): 663-676) may also be used.

Methods are known in the art for expanding and culturing pluripotent stem cells. Pluripotent stem cells may be plated onto a suitable culture substrate, such as an extracellular matrix component, such as those derived from basement membrane or that may form part of adhesion molecule receptor-ligand couplings. Examples include Matrigel. (Corning Life Sciences, Corning, N.Y.). Other extracellular matrix components and component mixtures include laminin, fibronectin, proteoglycan, entactin, heparin sulfate, and the like, alone or in various combinations.

In an embodiment, for generating PP2-β cells, human embryonic stem cells (ESC) or human ESC lines INS$^{GFP/W}$ HES3, HUES8, and H1 can be used. The cells can be grown on suitable substrate (such as Matrigel-coated plates) in suitable media (such as mTeSR1 medium (STEMCELL Technologies)). The medium can be supplemented with antibiotics. Cells are generally maintained at 37C with 5% $CO_2$. Cells can be passaged frequently (such as every 4-6 days).

To prepare for differentiation, hESCs can be dissociated with (such as with EDTA) and replated. Once the cells reach near-confluency (generally about 95%), differentiation can be initiated. On day 0, cells can be exposed to basal medium RPMI 1640 and a GSK3β inhibitor 3 (e.g., CHIR99021) and Activin A for a period (such as 24 hr). The medium may be supplemented with Glutamax, and Normocin. The medium can then be changed to basal medium and Activin A. The medium may be supplemented with Glutamax, normocin and fetal bovine serum (such as 0.2%) for another period (such as 2 days). The resulting cells (definite endoderm cells) can be cultured for a period (such as 2 to 6 days, and example is 4 days) in basal medium containing FGF7. The medium may be supplemented with Glutamax, normocin and fetal bovine serum or bovine serum albumin (such as 2%). This results in cells acquiring foregut fate. The cells can then be induced to differentiate to pancreatic endoderm in basal medium (such as DMEM with high glucose) supplemented with retinoic acid (RA), LDN193189 (LDN) and SANT-1 for a period (such as 4 days). These cells are termed PP1. The medium may then be refreshed and further supplemented with EGF and FGF2 to facilitate the transition from PP1 to PP2. In the case of the H1 line, cells can be treated with RA, LDN, SANT-1, EGF and FGF2 for a 14-day period. This period can vary between 5-25 days depending on different cell lines. After a period (such as on day 23), the PP2 cells differentiate into late stage INS$^+$ PP2-β-like cells in basal differentiation medium including DMEM supplemented with Glutamax, Normocin, B27 for 7 days (D30_L). For differentiation to PP1-β cells, PP1 cells on day 9 can be cultured for a period (such as 7 days) in the basal differentiation medium (D16_E). An example of this scheme is shown in FIG. 1a.

In an aspect, this disclosure provides a method for generation of enriched populations of monohormonal cells from pluripotent stem cells. The method comprises exposing pluripotent stem cells (such as human pluripotent stem cells) sequentially to basal medium supplemented with at least CHIR99021/GSK3beta inhibitor and Activin A; basal medium supplemented with at least Activin A to result in definitive endoderm (DE) cells; basal medium supplemented with at least FGF7; basal medium supplemented with at least retinoic acid, LDN193189, SANT1 to result in PP1 cells; basal medium supplemented with at least retinoic acid, LDN193189, SANT1, EGF and FGF2 to result in PP2 cells; and then allowing the cells to differentiate in basal differentiation medium to generate enriched population of mono-hormonal cells (PP2-β). Components like glutamine source (e.g., Glutamax), antibiotics, serum may be added to the medium. In an embodiment, the method consists essentially of or consists of exposing pluripotent stem cells (such as human pluripotent stem cells) sequentially to: basal medium supplemented with only CHIR99021/GSK3beta inhibitor and Activin A, and optionally, glutamine source, antibiotics, and/or serum; basal medium supplemented with only Activin A, and optionally glutamine source, antibiotics, serum; basal medium supplemented with only FGF7, and optionally glutamine source, antibiotics, and/or serum; basal medium supplemented with only retinoic acid, LDN193189, SANT1, and optionally glutamine source, antibiotics, and/or serum; basal medium supplemented with only retinoic acid, LDN193189, SANT1, EGF and FGF2, and optionally glutamine source, antibiotics, and/or serum; and then allowing the cells to differentiate in basal differentiation medium to generate enriched population of monohormonal cells (PP2-β).

In the enriched population of PP2-β cells, a majority of the cells produce insulin, but not glucagon, somatostatin or ghrelin. In embodiments, the enriched population has at least 50, 60, 70, 80, 90, or 95% monohormonal cells producing insulin. In an embodiment, the cells producing insulin do not produce glucagon, somatostatin or ghrelin. The generated PP2 cells are characterized as expressing NKX6.1 and NEUROD1 at levels higher than PP1 cells. In the enriched population of PP2-β cells, one or more of the following features are present: at least 95% of the cells express PDX1, at least 95% of the cells express NKX2.2, at least 85% of the cells express PAX6, at least 90% of the cells express ISL1, at least 50% of the cells express NKK6.1, and at least 60% of the cells express UCN3. In an embodiment the enriched population of PP2-β cells has all of the following features at least 95% of the cells express PDX1, at least 95% of the cells express NKX2.2, at least 85% of the cells express PAX6, at least 90% of the cells express ISL1, at least 50% of the cells express NKK6.1, and at least 60% of the cells express UCN3. The monohormonal cells were also observed to be Glis3$^+$.

In an aspect, this disclosure provides enriched populations of PP2-β cells generated from pluripotent stem cells (such as human pluripotent stem cells), wherein at least 50, 60, 70, 80, 90 or 95% of the cells are monohormonal producing insulin, but not glucagon, somatostatin or ghrelin and the enriched cell population has all of the following features at least 95% of the cells express PDX1, at least 95% of the cells express NKX2.2, at least 85% of the cells express PAX6, at least 90% of the cells express ISL1, at least 50% of the cells express NKK6.1, and at least 60% of the cells express UCN3. The monohormonal cells were also observed to be GLIS3$^+$.

In an aspect, this disclosure provides a kit for generation of enriched population of monohormonal cells from pluripotent stem cells, wherein the monohormonal cells produce insulin but not glucagon, somatostatin or ghrelin. The kit comprises in separate containers the cocktail of factors required for sequentially culturing the pluripotent stem cells. For example, a kit may contain separate sealed vials of: a) CHIR99021 and Activin A; b) Activin A; c) FGF7; d) retinoic acid, LDN193189, SANT1; and e) retinoic acid, LDN193189, SANT1, EGF and FGF2. The kit may also contain one or more containers of basal medium and basal differentiation medium. Optionally, the kit may contain instructions for use, including the times for exposure to medium comprising the above components.

This disclosure describes that small molecules, galunisertib, and other TGFβ inhibitors can effectively improve survival of primary β cells, hESC/iPSC-derived β cells and β cells derived from other resource. These small molecules, including galunisertib, and other TGFβ inhibitors, can be used for improving survival/rescue cell death of β cells both in vitro and in vivo, including, but not limited to, improving the survival of β cells for transplantation therapy.

This disclosure describes that small molecules, galunisertib, and other TGFβ inhibitors can be used for the treatment of neonatal diabetes and broadens the scope of precision medicine for more complex conditions, including T1D and T2D.

This disclosure identifies TGFβ pathway as a drugable target to improve the generation and survival of β cells both in vitro and for the direct treatment of diabetes patients.

EXAMPLE 1

GLIS3 mutations are associated with type 1, type 2 and neonatal diabetes, reflecting a key function for this gene in pancreatic β-cell biology. Previous attempts to recapitulate disease-relevant phenotypes in GLIS3$^{-/-}$ β-like cells have been unsuccessful. Here, we developed a "minimal component" protocol to generate the late stage pancreatic progenitors (PP2 cells) that differentiate to mono-hormonal glucose-responding pancreatic β-like cells (PP2-β cells). Using this directed differentiation platform, we discovered that GLIS3$^{-/-}$ hESCs show impaired differentiation, with significant death of PP2 and PP2-β cells, without impacting the total endocrine cell pool. Furthermore, we performed a high content chemical screen and identified a drug candidate that rescues mutant GLIS3-associated β-cell death both in vitro and in vivo. Finally, we discovered that loss of GLIS3 causes β-cell death, by activating TGFβ pathway. This study establishes an optimized directed differentiation protocol for modeling human β-cell disease and identifies a drug candidate for treating a broad range of GLIS3-associated diabetic patients.

Candidate gene and genome wide association studies (GWAS) have identified ~150 susceptibility loci for type 1 (T1D) and type 2 (T2D) diabetes. Of the genes identified so far, GLIS3 is the only one (other than insulin) associated with T1D (Barrett et al. *Nature genetics* 41, 703-707 (2009); Stecket al. *Pediatric diabetes* 15, 355-362 (2014); Winkler et al. *Diabetologia* 57, 2521-2529 (2014)), T2D (Dupuis et al. *Nature genetics* 42, 105-116 (2010); Cho et al. *Nature genetics* 44, 67-72 (2011); Li et al. *Diabetes* 62, 291-298 (2013); Goodarzi et al. *Diabetologia* 56, 1282-1290 (2013)), and in addition neonatal diabetes (Senee et al. *Nature genetics* 38, 682-687 (2006)). During mouse development, PDX1$^+$ pancreatic progenitors appear around embryonic day (E) E8.5; at E11.5, a small subset give rise to mostly poly-hormonal endocrine cells commonly referred to as "primary transition" endocrine cells that likely do not contribute to the mature β-cell pool (Herrera, *Development* 127, 2317-2322 (2000)). At E14.5, the "secondary transition" begins with extensive differentiation and emergence of mono-hormonal β-cells (Murtaugh, *Development* 134, 427-438 (2007)). *Glis*3 begins to be expressed only in the secondary transition stage, is continually expressed in pancreatic β-cells and ductal cells (Kang et al. *PloS one* 11, e0157138 (2016)), and plays a critical role in endocrine development (Kang et al. *Molecular and cellular biology* 29, 6366-6379 (2009)). In *Glis*3-deficient mice all subtypes of endocrine cells, especially β and δ cells[12], are significantly reduced, causing neonatal diabetes (NDM) (Yang et al. *Diabetologia* 54, 2595-2605 (2011); Watanabe et al. *FEBS letters* 583, 2108-2113 (2009)). Glis3 is also essential for compensatory β-cell proliferation in adult mice (Yang, et al., *EMBO molecular medicine* 5, 92-104 (2013)). The absence or decreased expression of Glis3 predisposes the mice to T2D (Yang, et al., *EMBO molecular medicine* 5, 92-104 (2013); Yang et al., *Endocrinology*, en20161541 (2016). In addition, *Glis*3 mutations in non-obese diabetic (NOD) mice have been shown to underlie β-cell fragility and susceptibility to T1D (Dooley, *Nature genetics* 48, 519-527 (2016)). However, the role of GLIS3 in human pancreatic development and human β-cells remains unclear.

Human pluripotent stem cells (hPSCs) have provided robust platforms to recapitulate pancreatic β-cell defects in diabetes, including maturity-onset diabetes of the young and neonatal diabetes. Recently, we used an isogenic hESC differentiation platform to evaluate the role of T2D-associated genes in pancreatic β-cell function and survival in disease conditions (Zeng et al. *Cell Stem Cell* 19, 326-340 (2016)). However, our initial attempt using isogenic $GLIS3^{-/-}$ hESCs failed to recapitulate the defects observed in $Glis3^{-/-}$ mice (Zhu et al. Cell Stem Cell 18, 755-768 (2016)). This raised the question whether GLIS3 plays different roles in mouse and human or whether the current differentiation strategy is not optimal to model GLIS3-related pancreatic β-cell defects. To distinguish between these possibilities, we monitored GLIS3 mRNA in hESC-derived pancreatic progenitors and $INS^+$ cells and found that the expression GLIS3 mRNA is under detection, suggesting that the previous protocol (D'Amour et al. *Nature biotechnology* 24, 1392-1401 (2006)) failed to efficiently generate the disease relevant cells. Here, we describe an optimized strategy to efficiently derive $GLIS3^+$ late stage pancreatic progenitors (PP2), which give rise to mono-hormonal pancreatic β-cells (PP2-β cells). We used this platform to determine the role of GLIS3 in human pancreatic β-cell generation and survival, and to identify a lead hit candidate drug for treating the broad range of human patients who suffer from GLIS3-associated diabetes.

Results

Figure 6:
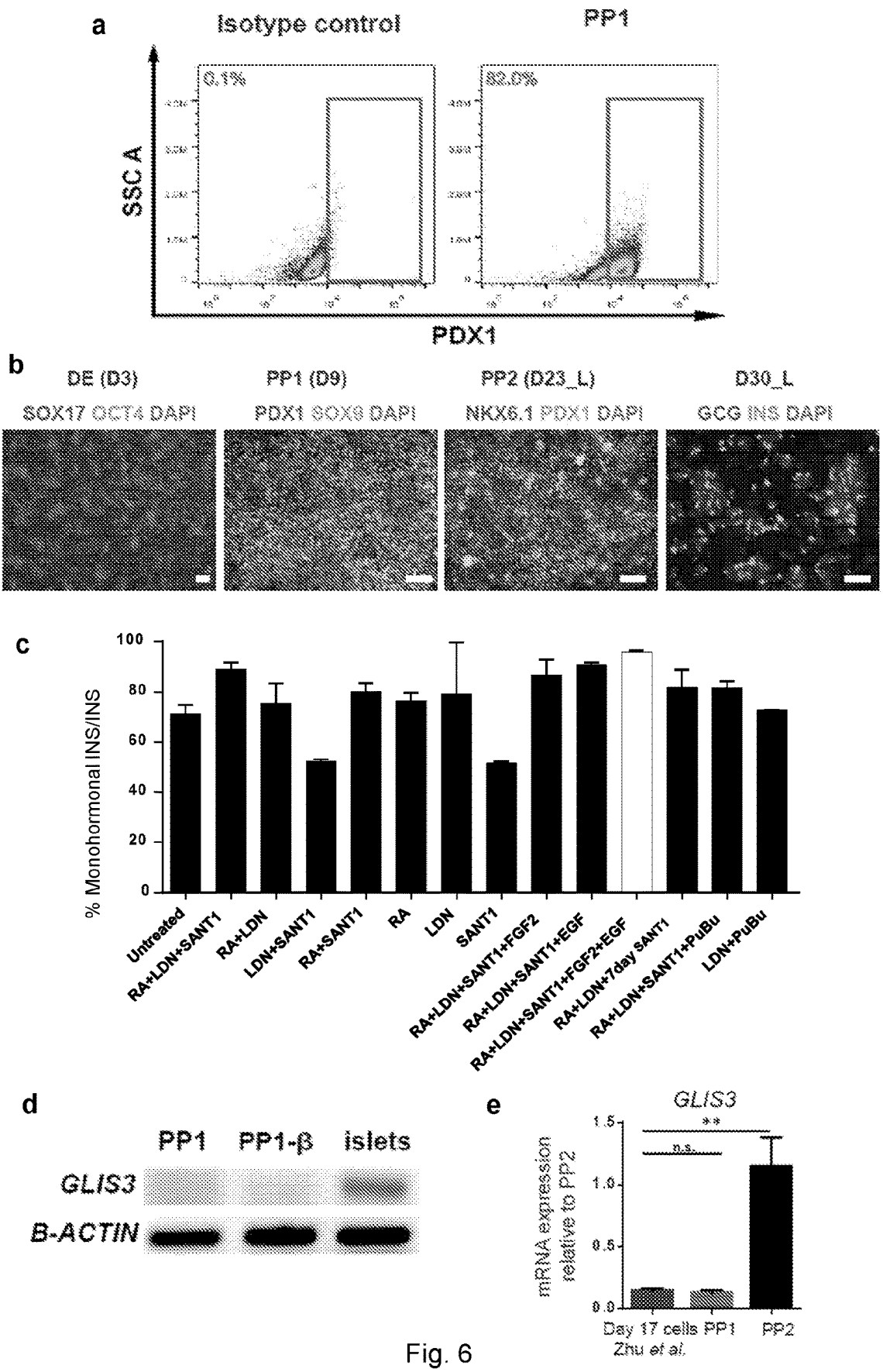
FIG. 6. A pilot screen to establish the protocol to generate late stage pancreatic progenitors that give rise to mono-hormonal PP2-β cells. (a) Intracellular flow cytometry for PDX1 expression in PP1 cells. (b) Representative images for DE, PP1, PP2 cells and cells at D30_L. Scale bar=100 µm. (c) The percentage of mono-hormonal (INS+/GCG-SST-) cells in INS+ cells derived in different culture media conditions (n=2). (d) RT-PCR analysis of GLIS3 expression in PP1, PP1-β and human islets. (e) qRT-PCR analysis of GLIS3 expression in day 17 (PH-β) cells from Zhu et al, PP1 and PP2 cells. (PH-β n=4, PP1 and PP2 n=6). (f) Time-course qRT-PCR analysis of GLIS3 expression during transition from PP1 to PP2 stages of differentiation. (Data are normalized to ES; PP1, PP2 n=6, day 12, 16, 19 n=4). (g) Immunocytochemistry analysis of INS and SST expression at D16_E and D30_L. Scale bar=100 µm. (h) Intracellular flow cytometry analysis of INS and SST expression at D16_E and D30_L.(i) Immunocytochemistry analysis of INS and GHRL expression at D16_E and D30_L. Scale bar=100 µm. (j) Intracellular flow cytometry analysis for INS and GHRL expression at D16_E and D30_L. (k) C-peptide secretion (% of total c-peptide content) in response to 2 mM (low) and 20 mM (high) D-glucose conditions. Data are shown for individual batches of cells at D30_L and human islets (PP2-β n=5, Human islets n=10). (l) Intracellular flow cytometry analysis of INS and GCG expression in cells at D30_L derived from HUES8 and H1 hESCs. (m) Intracellular flow cytometry analysis for co-expression of different endocrine hormones (GCG, SST and GHRL) at D30_L. (n) qRT-PCR analysis of UCN3 and MAFA in PP2-β cells and human primary islets (PP2-β n=5, Human islets n=7). P values by multiple unpaired student t-test were *P<0.05, P<0.01, *P<0.001, ****P<0.0001, n.s. not significant. The center value is "mean". Error bar is SEM.
Figure 6:
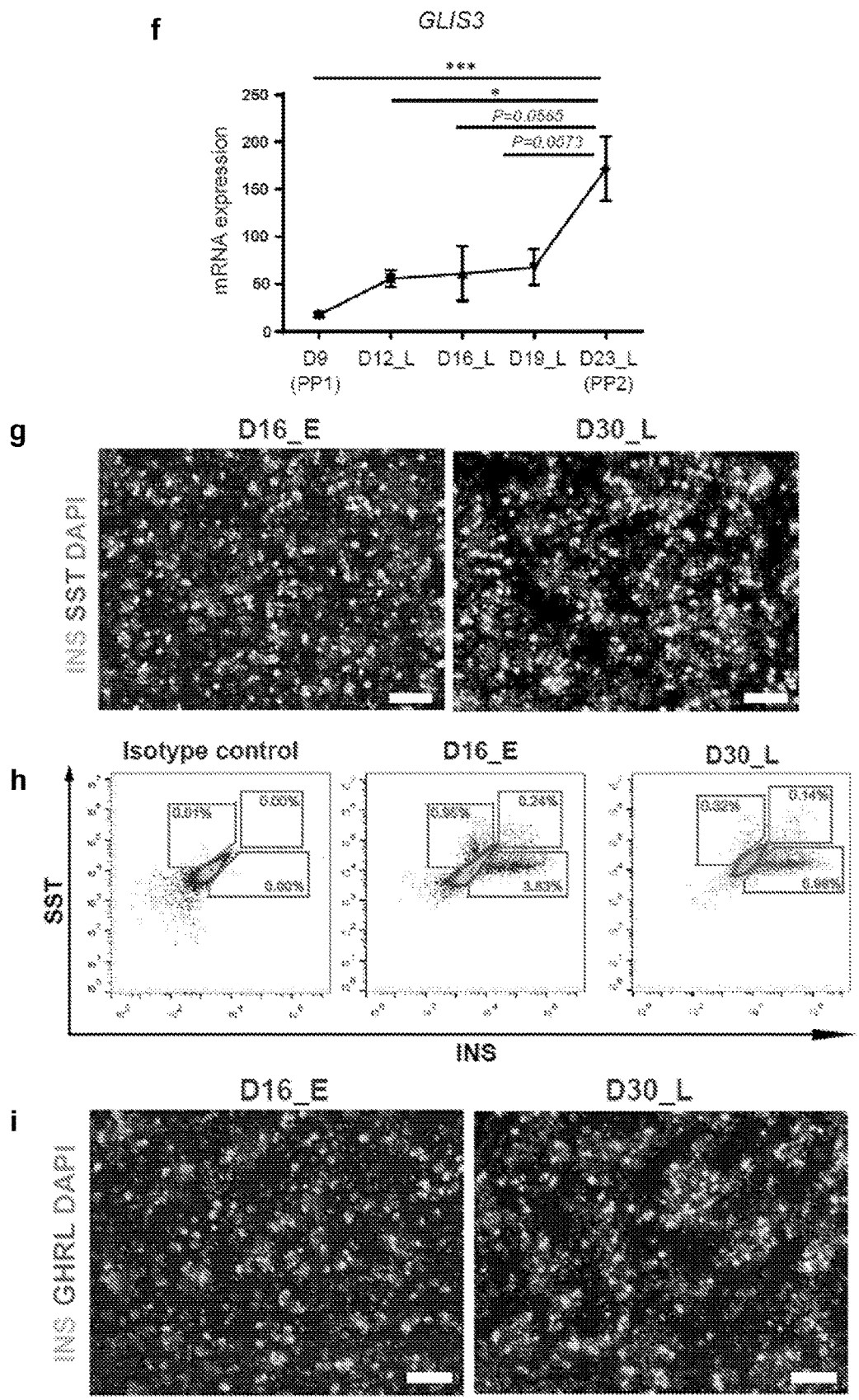
Figure 6:
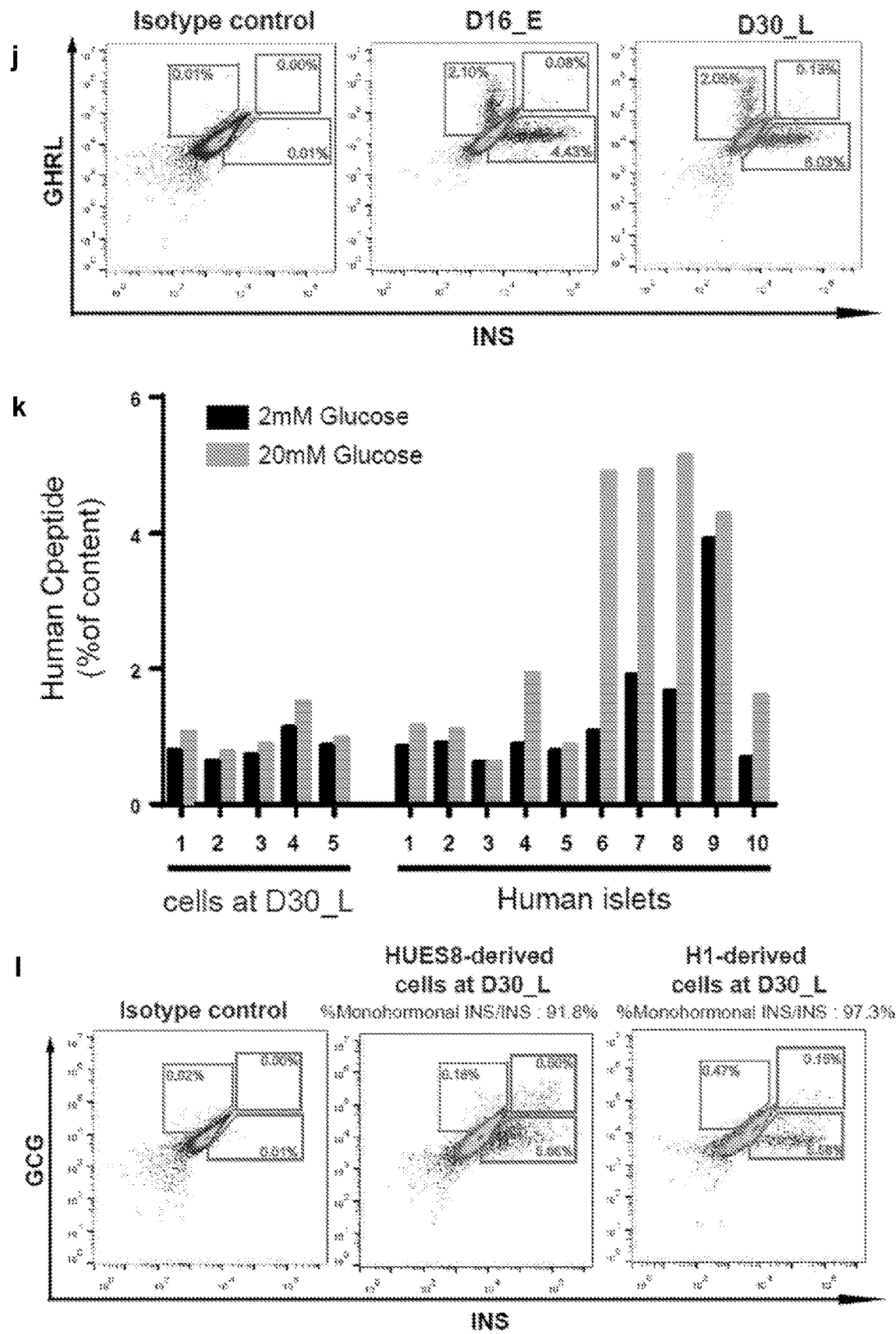
Figure 6:
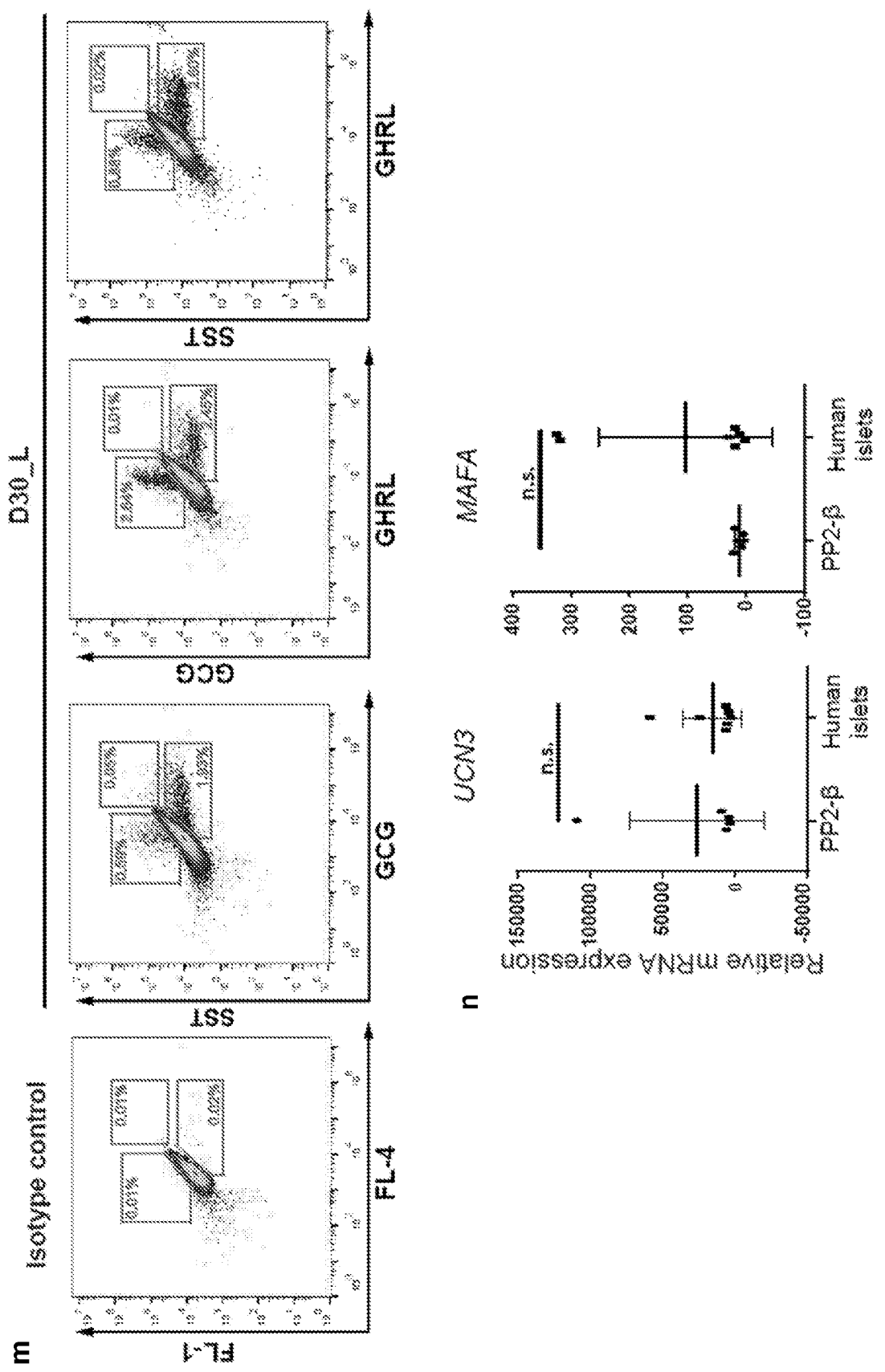

A "minimal component" protocol to derive late stage pancreatic progenitors that give rise to mono-hormonal cells. Lacking an effective antibody for analyzing GLIS3 by immunocytochemistry, we used an indirect functional readout to identify conditions that promote the generation of PP2 cells with the capacity to differentiate into mono-hormonal insulin-expressing β-like cells. To compare conditions, $INS^{GFP/W}$HES3 hESCs were differentiated to the early stage pancreatic progenitors (PP1 at day 9/D9, FIG. 1a, Table 1), giving rise to a pool that contains around 75-90% $PDX1^+$ cells (FIG. 6a, 6b). The PP1 cells can differentiate into $INS^+$ (PP1-β cells when cultured for seven additional days in basal differentiation medium (DMEM B27, FIG. 1a). However, the derived PP1-β cells are mostly poly-hormonal (comprising a population of 60-70% poly-hormonal and 30-40% mono-hormonal $INS^+$ cells), which represent the cells from older protocols[23, 24](FIG. 1d-1f). The $INS-GFP^+$ PP1-β cells do not express detectable levels of GLIS3 by RT-PCR (FIG. 6d). Poly-hormonal $INS-GFP^+$ PP1-β cells were previously shown to differentiate mostly to α-cells when transplanted in vivo[25], which suggests that their identity is closer to the primary transition cells in mouse development. We performed a pilot screen to establish a strategy to promote the generation of PP2 cells that give rise to mono-hormonal $INS^+$ cells. Among 14 different culture conditions, we found one that consistently generates the highest percentage of PP2-derived insulin$^+$/glucagon$^-$ somatostatin$^-$($INS^+$/$GCG^-SST^-$) cells for the total $INS^+$ population (FIG. 6c). This was achieved with "PP extension medium" containing 2 μM RA, 200 nM LDN193189, 0.25 μM SANT1, 10 ng/mL EGF and 10 ng/mL FGF2. After 14 days of culture (from day 9 to day 23) in PP extension medium, more than 90% of the cells expressed PDX1 at day 23/D23_L (FIG. 6b). Compared with PP1, PP2 cells express higher levels of late trunk PP markers, including NKX6.1, and NEUROD1 as indicated by qRT-PCR assays (FIG. 1b, Table 2) and RNA-seq profiling (FIG. 1c). More importantly, after seven days of differentiation, 85-95% of $INS^+$ cells derived from PP2 are mono-hormonal, expressing insulin, but not glucagon (FIG. 1d-1f), somatostatin, or ghrelin (FIG. 6g-6j). In contrast, only 30-40% of $INS^+$ PP1-β cells are mono-hormonal (FIG. 1d-1f and FIG. 6h, 6j). In addition, PP2-β cells co-express mature β-cell markers (FIG. 1g, 1h), including PDX1 (97.3%), NKX2.2 (98.8%), PAX6 (86.0%), ISL1 (91.8%) and NKX6.1 (50.8%), and they also express UCN3 (63.6%), a mature β-cell marker[26] that was not reported as expressed using any of three previously published protocols[27-29]. We also looked at the mRNA expression of UCN3 and another β-cell marker MAFA. There is no significant difference of UCN3 and MAFA expression detected between PP2-β cells and primary human islets (FIG. 6n). However, it is worth to note that big variation of UCN3 and MAFA expression was detected among different batches of human islets. RNA-seq profiling validated the downregulation of α-cell markers, ARX and glucagon, and other non-β-cell hormones in the purified $INS-GFP^+$ PP2-β cells, further confirming their mono-hormonal identity. Moreover, mature pancreatic β-cell markers are upregulated in the PP2-β $INS^+$ cells (FIG. 1h). Gene set enrichment analysis (GSEA) indicates that PP2-β cells closely resemble primary adult human β-cells. An upregulated gene set, comprising 1000 genes that are more highly expressed in adult human β-cells (~5-fold), are enriched in PP2-β cells; the downregulated gene set, comprising 1000 genes expressed at lower levels (~4-fold) in adult human β-cells, are enriched in PP1-β cells (FIG. 1i). Strikingly, PP2 and PP2-β cells express high levels of GLIS3 RNA, whereas GLIS3 transcripts are expressed at much lower levels in both PP1 and PP1-β cells (FIG. 1b, 1j, FIG. 6d, 6f). Compared to PP2 cells, the D17 cells generated using the previous protocol show limited GLIS3 expression, which explains why our previous studies did not detect defects of $GLIS3^{-/-}$ hESCs[20] (FIG. 6e). Finally, cells at D30_L release insulin in response to stimulation with 20 mM glucose (FIG. 1k and FIG. 6k) or other β-cell secretagogues, including 35 mM KCl, 30 μM Forskolin, or 10 mM Arginine (FIG. 1l). Using this strategy, mono-hormonal $INS^+$ cells were also derived with similar efficiency from HUES8 and H1 lines, demonstrating that that this differentiation strategy is not hESC line-dependent (FIG. 6l and Table 3). Also, the majority of α-like, δ-like and ε-like cells at D30_L are monohormonal (FIG. 6m).

Figure 2:
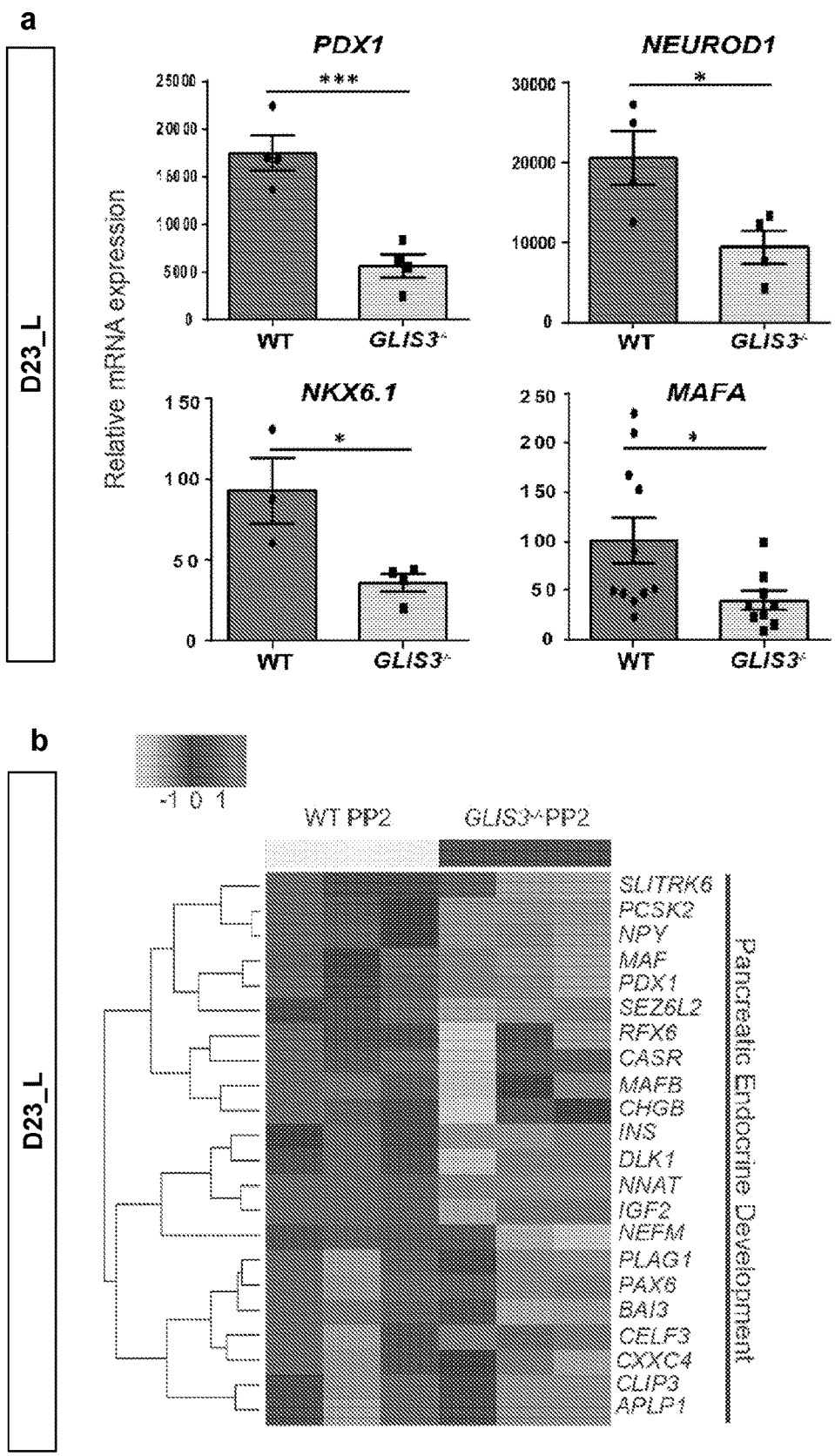
FIG. 2. Biallelic mutation of GLIS3 affects pancreatic differentiation and the generation of endocrine cells. (a) qRT-PCR analysis of pancreatic markers in the isogenic WT and GLIS3$^{-/-}$ PP2 cells. (PDX1, NEUROD1, NKX6.1 n=4, MAFA n=12) (b) Heatmap representing the relative expression levels of endocrine genes in WT and GLIS3$^{-/-}$ PP2 cells (n=3). (c) GSEA analysis showing the decrease of endocrine pancreas-related genes in GLIS3$^{-/-}$ PP2 cells. (d, e) Gene ontology (GO) analysis (d) and KEGG pathway analysis (e) of genes significantly downregulated (P<0.01) in GLIS3$^{-/-}$ PP2 cells. (f) Flow cytometry analysis of WT and GLIS3$^{-/-}$ cells at D30_L. (g) Quantification of the percentage of INS-GFP$^+$ cells of WT (n=6) and GLIS3$^{-/-}$ (n=9) cells at D30_L. The percentage of INS-GFP$^+$ cells was quantified based on flow cytometry analysis of GFP$^+$ cells. (h) Quantification of the percentage of INS$^+$ cells of WT (n=11) and GLIS3$^{-/-}$ (n=14) cells at D30_L. The percentage was quantified based on intracellular flow cytometry analysis of INS$^+$ cells. (i) Total percentage of endocrine cells in isogenic WT (n=10) and GLIS3$^{-/-}$ (n=12) cells at D30_L. The percentage of endocrine cells is calculated as the sum of the percentages of INS$^+$, GCG$^+$, SST$^+$ and GHRL$^+$ cells. (j) Plot representing the ratios of different endocrine subtypes in WT and GLIS3$^{-/-}$ cells at D30_L. (k) Immunocytochemistry analysis of pancreatic endocrine marker expression in WT and GLIS3$^{-/-}$ cells at D30_L. Scale bar=100 μm. (l, m) Histogram showing fluorescence intensity (i) and quantification of median fluorescence values (m) of INS staining of WT and GLIS3$^{-/-}$ PP2-β cells. (n=4). (n) Insulin content of the purified INS-GFP$^+$ WT and GLIS3$^{-/-}$ PP2-β cells (n=4). Data are normalized to the WT mean value. P values by unpaired two-tailed t-test were *P<0.05, P<0.01, *P<0.001, ****P<0.0001. The center value is "mean". Error bar is SEM.
Figure 2:
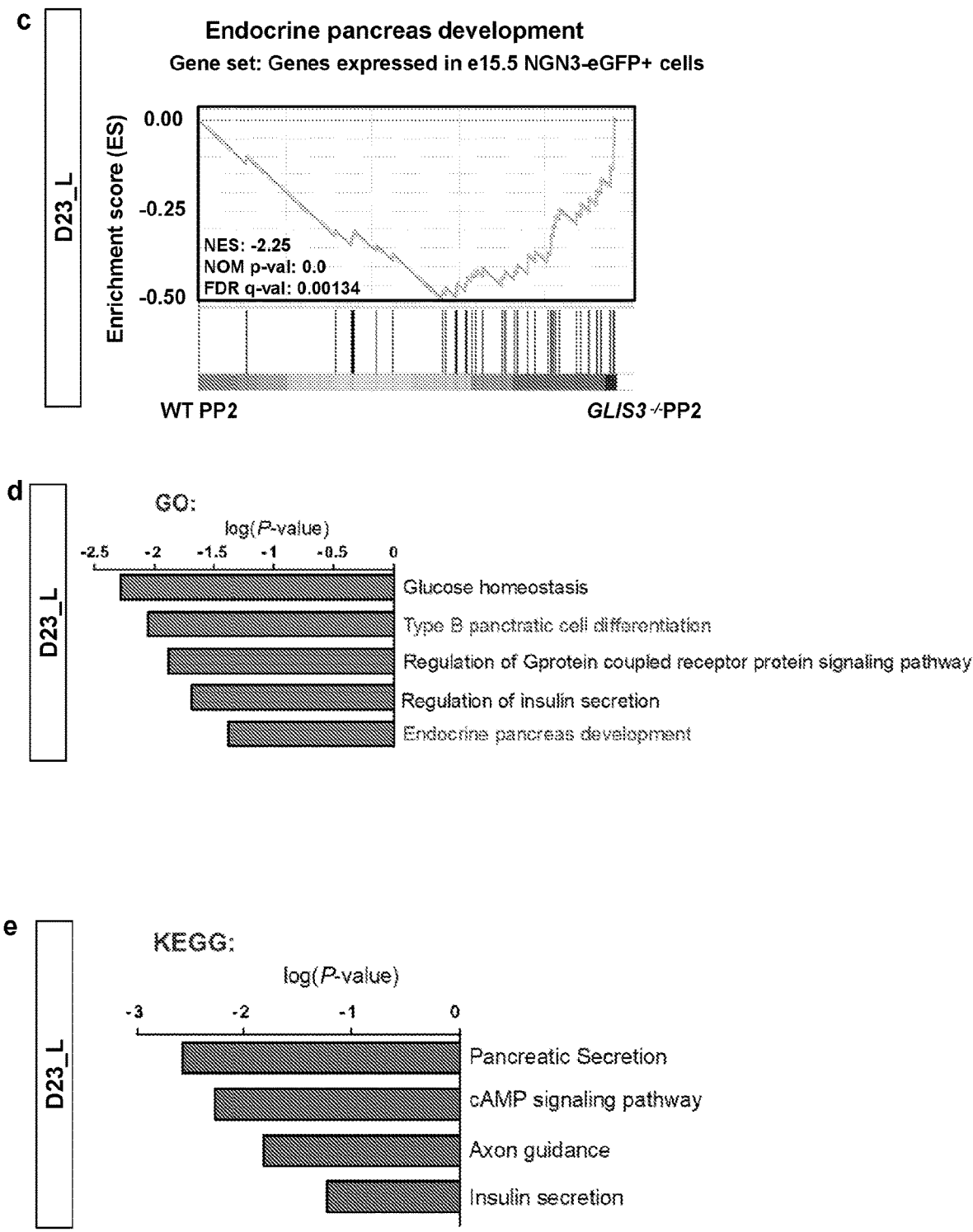
Figure 2:
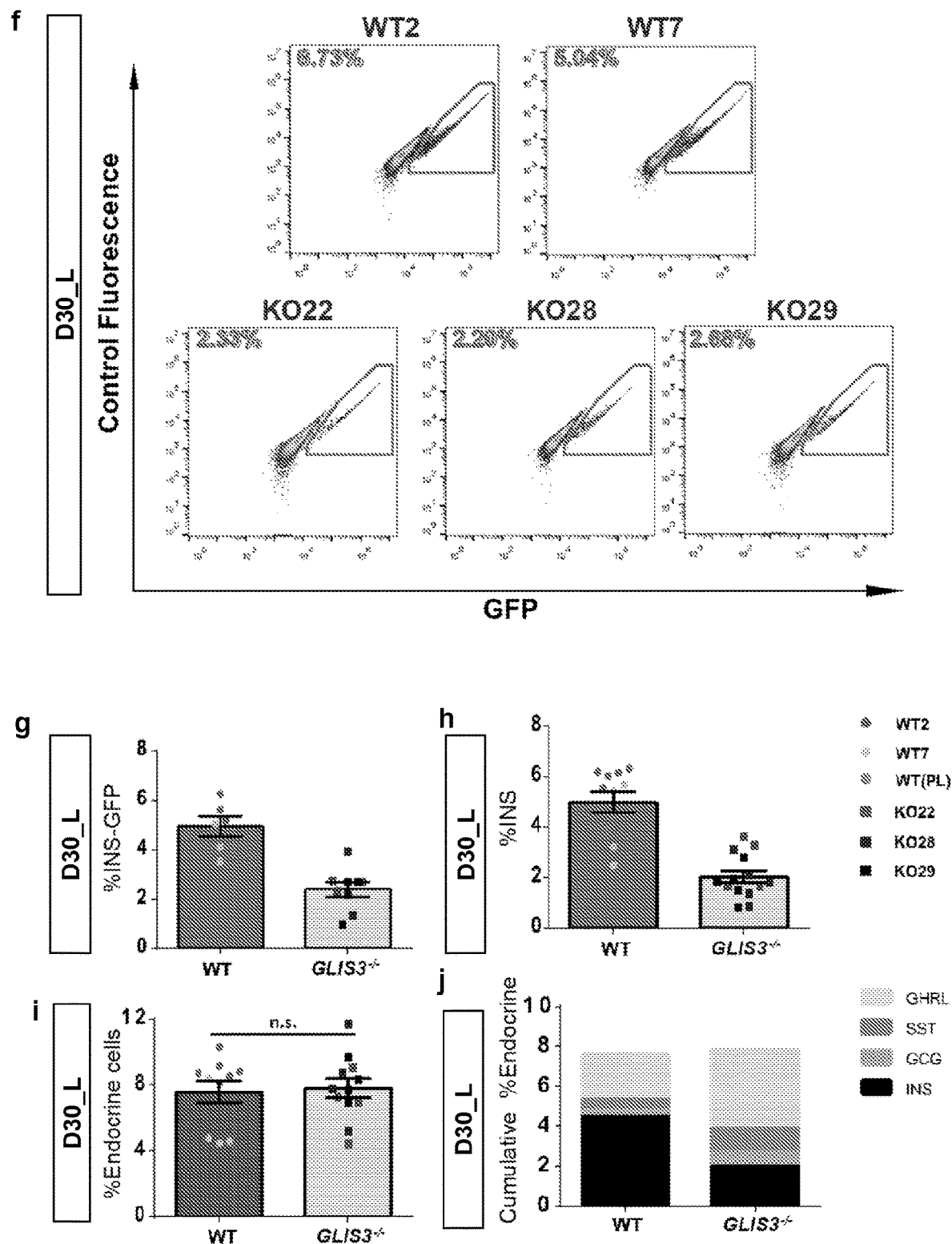
Figure 7:
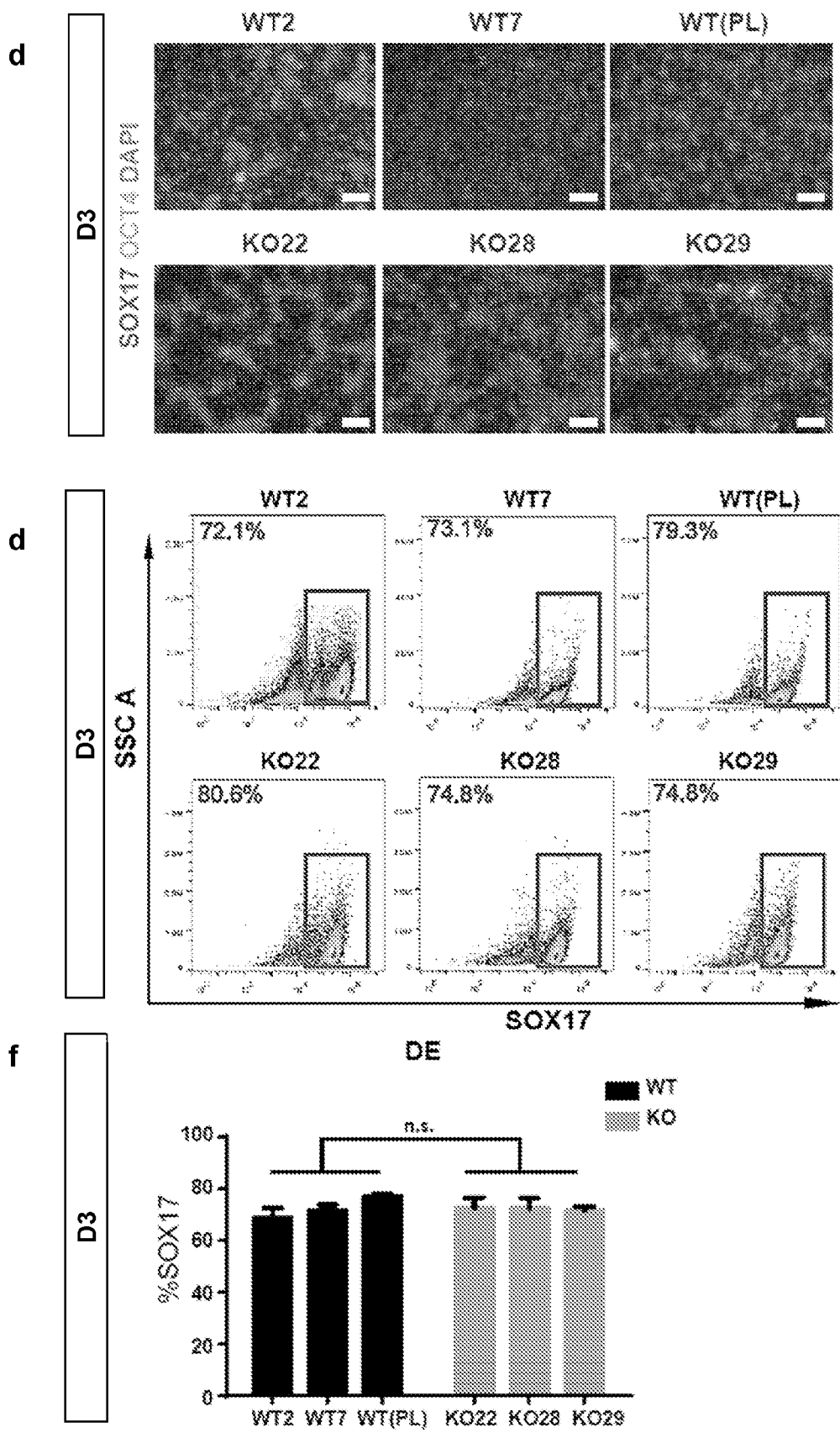
FIG. 7. Generation and characterization of GLIS3–/– hESC lines. (a) Schematic representation of the targeting strategy to induce frameshift mutations in exon 3 of the GLIS3 gene. (b) Sequencing results of two distinct WT hESC clones. (c) Sequencing results of three distinct GLIS3–/– hESC clones. (d) Immunocytochemistry analysis of WT and GLIS3–/– DE cells. Scale bar=200 (e, f) Intracellular flow cytometry analysis (e), and quantification (f) of WT and GLIS3–/– DE cells at D3. (WT2 and KO29 n=4, all other lines n=3) (g) Immunocytochemistry analysis of WT and GLIS3–/– cell at D9. Scale bar=100 µm. (h, i) Intracellular flow cytometry analysis (h), and quantification (i) of WT and GLIS3–/– cells at D9.(n=3 for WT7, n=1 for WT (PL), n=4 for all other lines). (j) Isotype control plots for PDX1 staining at D9 and D23_L. (k, l) Intracellular flow cytometry analysis (k) and the quantification (l) of WT and GLIS3–/– lines at D23_L (WT lines n=2, GLIS3–/– lines n=3). P values by multiple unpaired student t-test were *P<0.05, P<0.01, *P<0.001, ****P<0.0001, n.s. not significant. The center value is "mean". Error bar is SEM.
Figure 7:
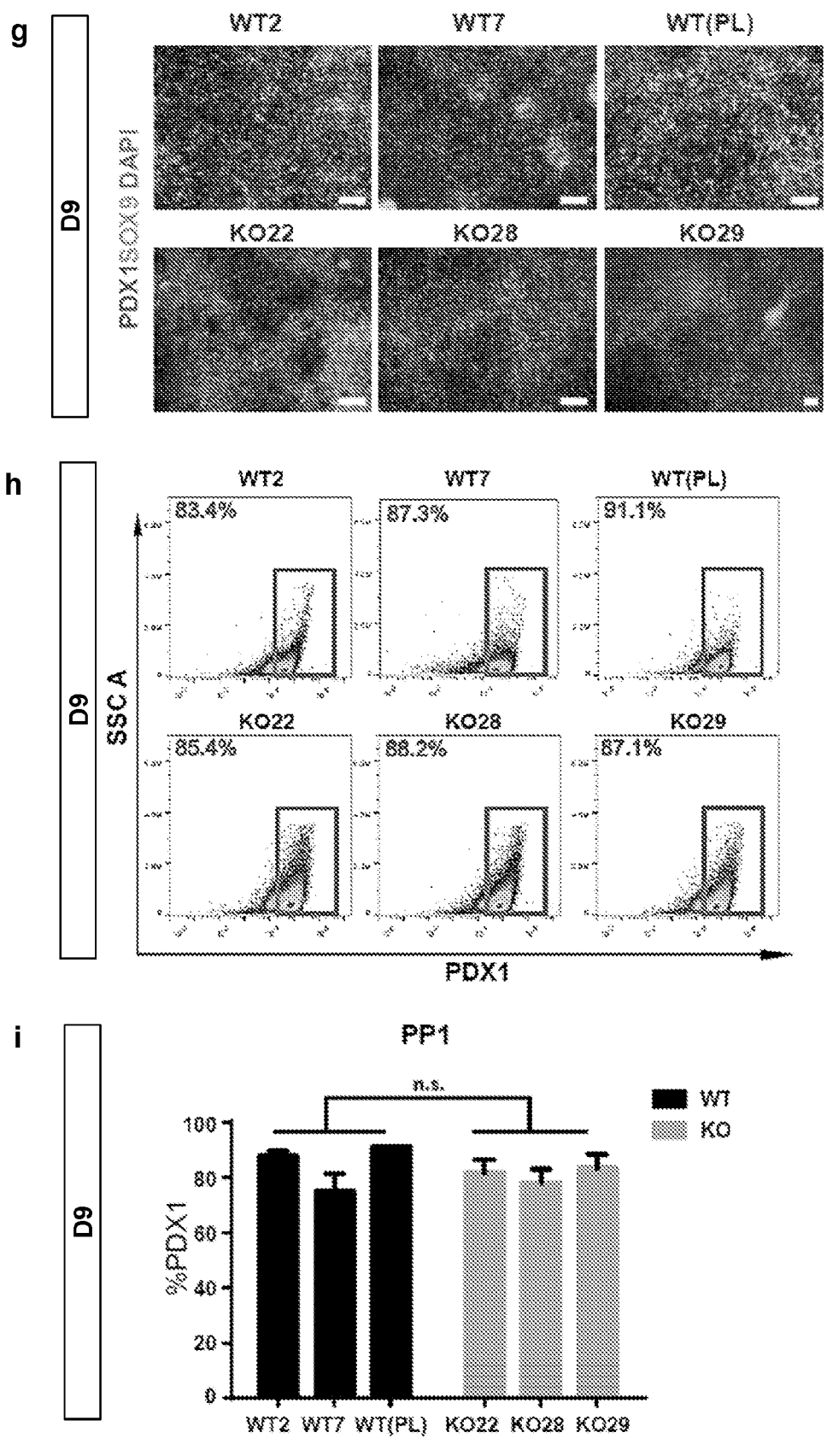
Figure 8:
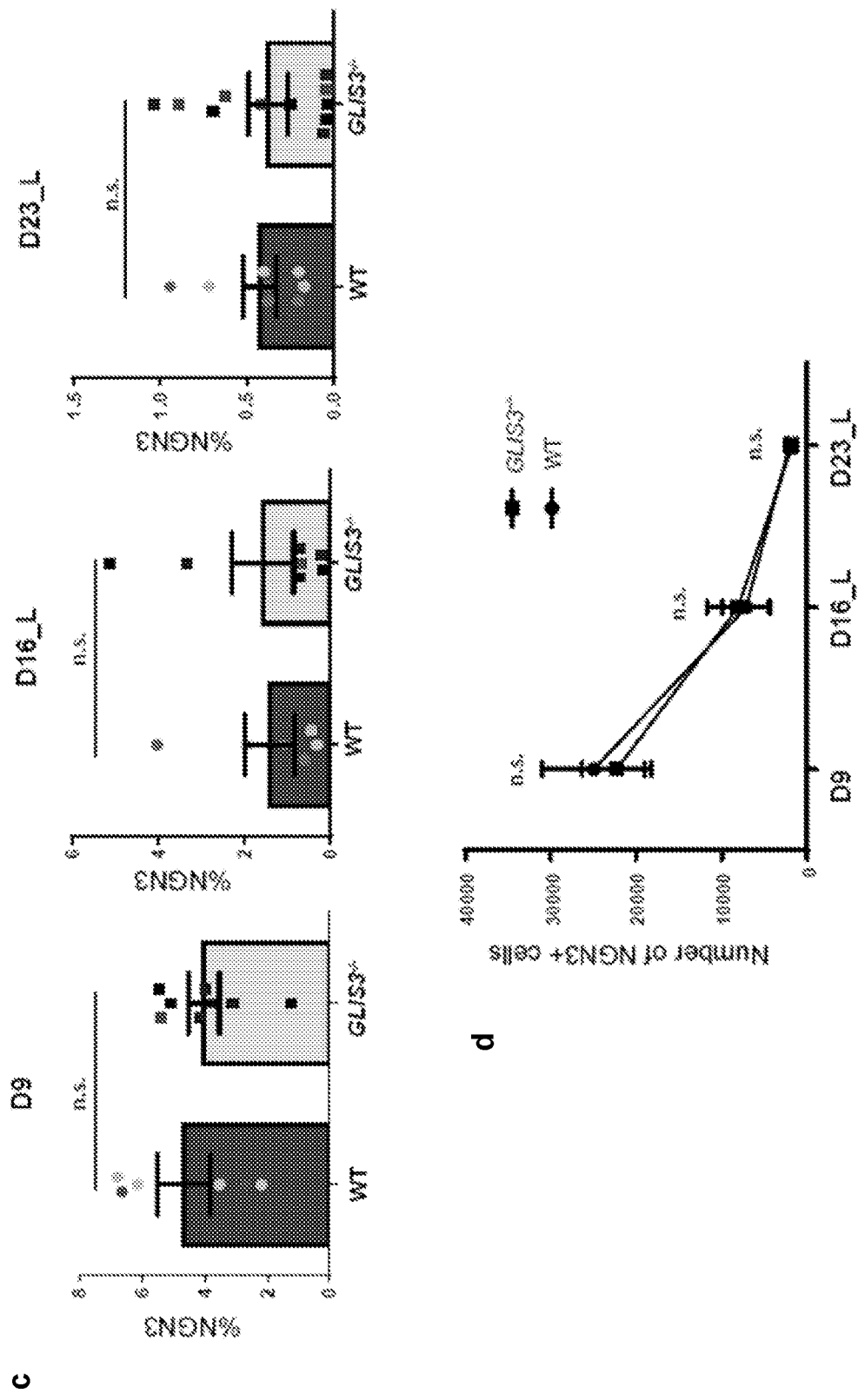
FIG. 8. Quantification and characterization of the endocrine progenitors and their derivatives. (a) GSEA analysis showing the decrease of endocrine pancreas-related genes in GLIS3−/− cells at D23_L (n=3). (b) Representative immunostaining images for NGN3 and CHGA staining on D9, D16_L and D23_L of the differentiation to derive late stage pancreatic progenitors. Scale bar=100 µm. (c, d) Immunostaining quantification of the percentage (c) and number (d) of NGN3+ cells in WT and GLIS3−/− cells D9, D16_L and D23_L of differentiation. (WT, n=6 for D9 and D16_L, n=9 for D23_L, GLIS3−/−, n=8 for D9 and D16_L, n=11 for D23_L). (e, Immunostaining quantification of the percentage (e) and number (f) of CHGA+ cells in WT and GLIS3−/− on D9, D16_L and D23_L of differentiation. (WT, n=4 for D9 and D16_L, n=6 for D23_L, GLIS3−/−, n=6 for D9 and D16_L, n=8 for D23_L). (g) Representative images of NGN3 immunostaining in WT and GLIS3−/− cells at D23_L. Scale bar=100 µm. (h) Distribution of NGN3 fluorescence intensity among NGN3+ WT and GLIS3−/− cells at D23_L. (i) Mean fluorescence intensity values for NGN3 immunostaining in WT and GLIS3−/− cells at D23_L (WT n=4, GLIS3−/− n=5).
Figure 8:
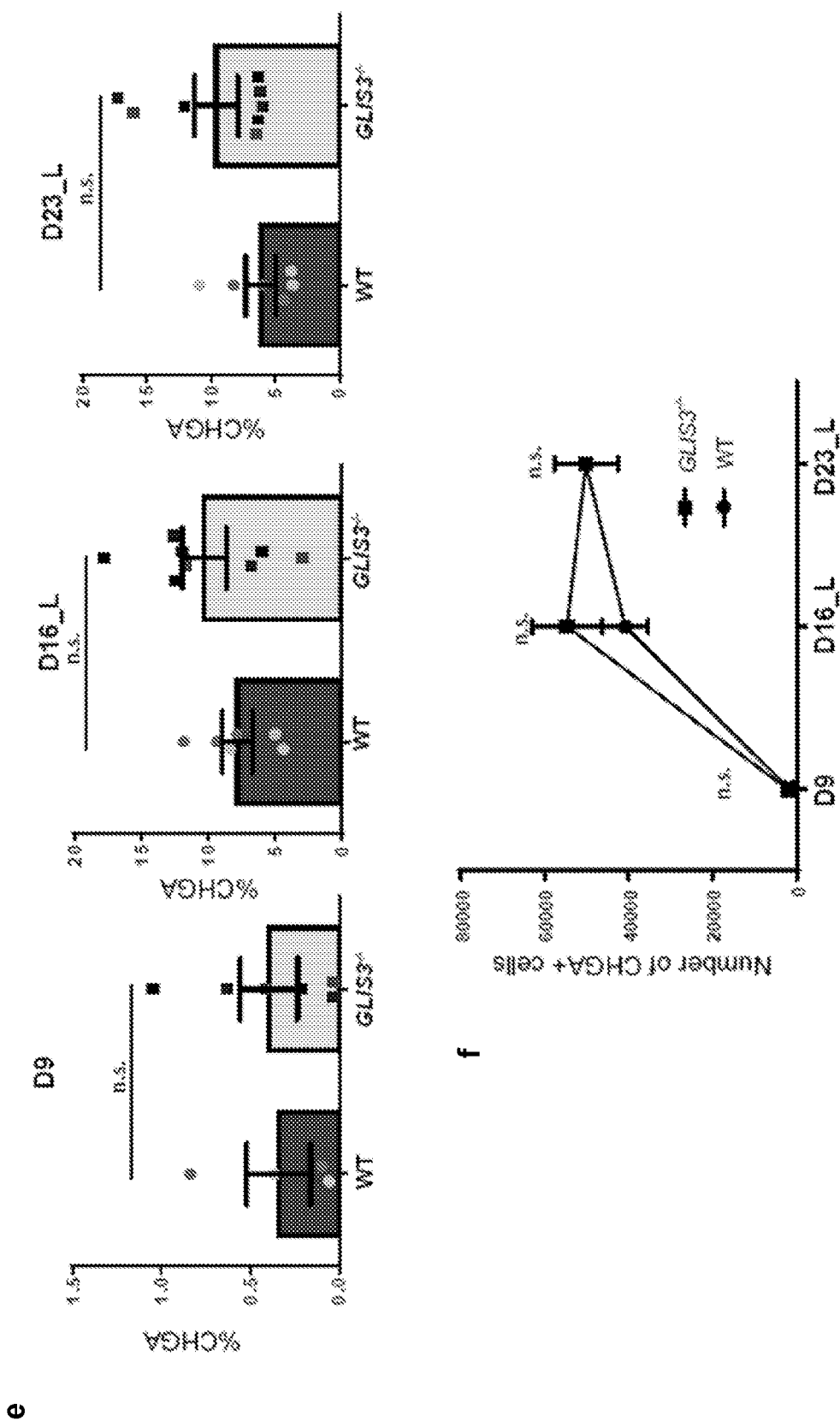
Figure 8:
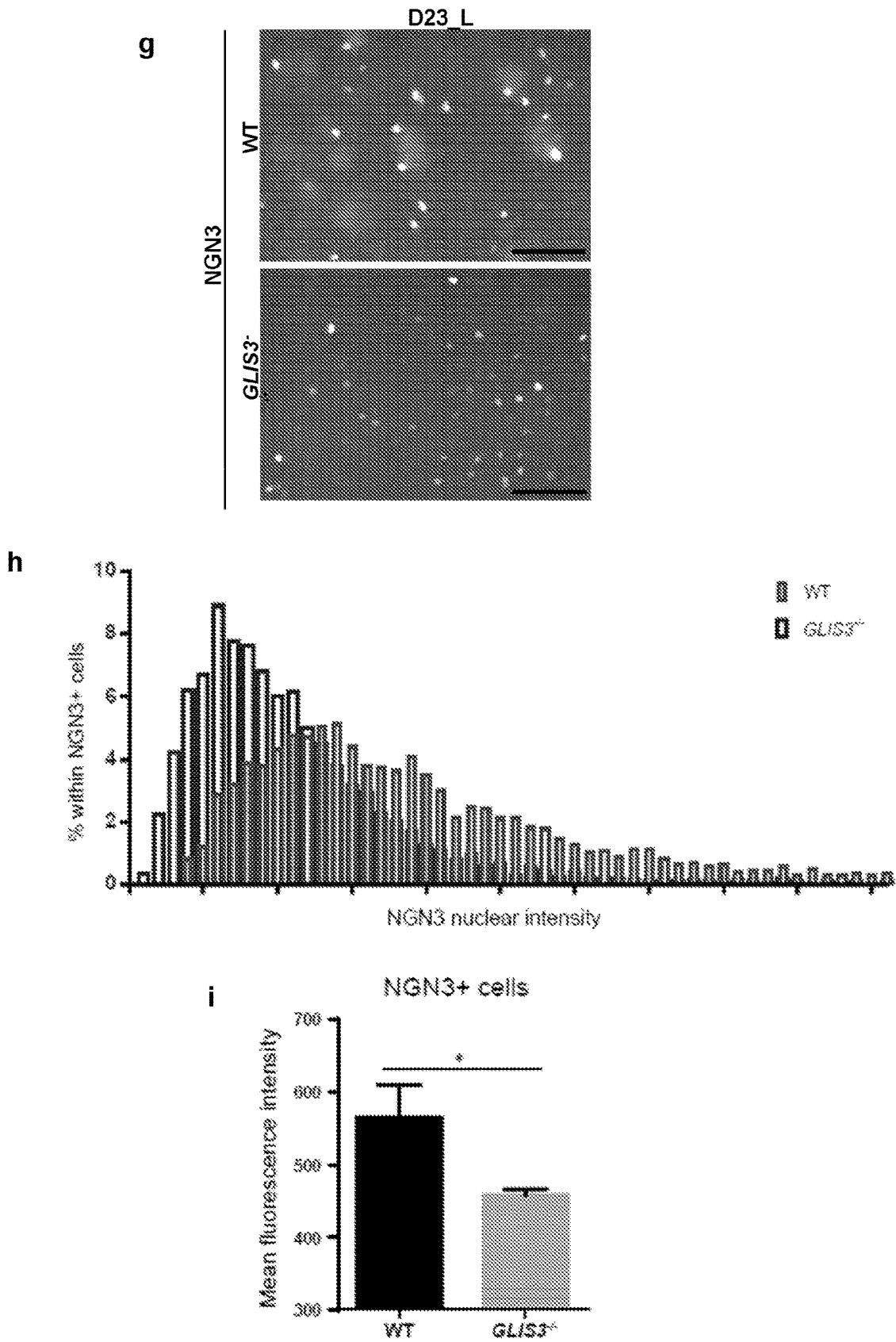

$GLIS3^{-/-}$ hESCs show impaired differentiation toward pancreatic β-like cells. We used this improved differentiation protocol to evaluate the role of GLIS3 in human pancreatic development and generation of pancreatic β-like cells. To create biallelic GLIS3 mutant hESC lines, indel mutations were induced in $INS^{GFP/W}$ HES3 cells using a sgRNA targeting exon 3 of GLIS3 gene, predicted to impact all splice variants (FIG. 7a and Table 4-6). The indel mutations were confirmed by Sanger sequencing (FIG. 7b-7c) and are predicted to create an early frameshift and generate null alleles. To account for possible clonal variation, we analyzed three GLIS3$^{-/-}$ clones (KO22, KO28 and KO29) and two wild type (WT) clones (WT2 and WT7) along with the parental HES3 line (WT (PL)). Details for clonal lines used in each experiment are listed in Table 7. These isogenic WT and mutant lines were differentiated to D30_L using our established strategy (FIG. 1a). No significant difference was detected between WT and mutant lines with respect to their capacities to differentiate toward definitive endoderm (SOX17$^+$OCT4$^-$, FIG. 7d-7f) or PP1 (PDX1$^-$7 SOX9$^+$, FIG. 7g-7i). This is in agreement with a previous study that found no obvious defects in GLIS3$^{-/-}$ HUES8 cells[20]. At D23_L, no significant difference is detected between WT and mutant lines regarding the percentage of PDX1$^+$ cells (FIG. 7k, 7l). However, qRT-PCR assays revealed decreased relative expression levels in GLIS3$^{-/-}$ PP2 cells for key pancreatic endocrine markers, including PDX1, NEUROD1, NKX6.1 and MAFA (FIG. 2a). RNA profiling (FIG. 2b) and GSEA (FIG. 2c, 8a) showed a marked decrease in the expression of genes related to the pancreatic endocrine compartment in GLIS3$^{-/-}$ PP2 cells. Consistent with these data, gene ontology (GO, FIG. 2d) and KEGG pathway (FIG. 2e) analyses highlight downregulation of Type B pancreatic cell differentiation and endocrine pancreas development in GLIS3$^{-/-}$ PP2 cells. Taken together, these findings suggest that endocrine development is compromised in GLIS3$^{-/-}$ PP2 cells. To decipher whether the decrease in endocrine-related genes is due to decreased number of endocrine cells or a reduction of transcripts per cell, the number and percentage of endocrine progenitors (NGN3$^+$) and their derivatives (CHGA$^+$) were quantified at different time points during transition from D9 to D23_L (FIG. 8a-8f). There was no significant difference between WT and GLIS3$^{-/-}$ cells at any of the steps tested. However, we observed a decrease in fluorescence intensity of NGN3 staining in GLIS3$^{-/-}$ cells at D23_L, suggesting that loss of GLIS3 might decrease the expression of NGN3 per cell, instead of affecting the percentage of NGN3$^+$ cells (FIG. 8g-8i).

Figure 9:
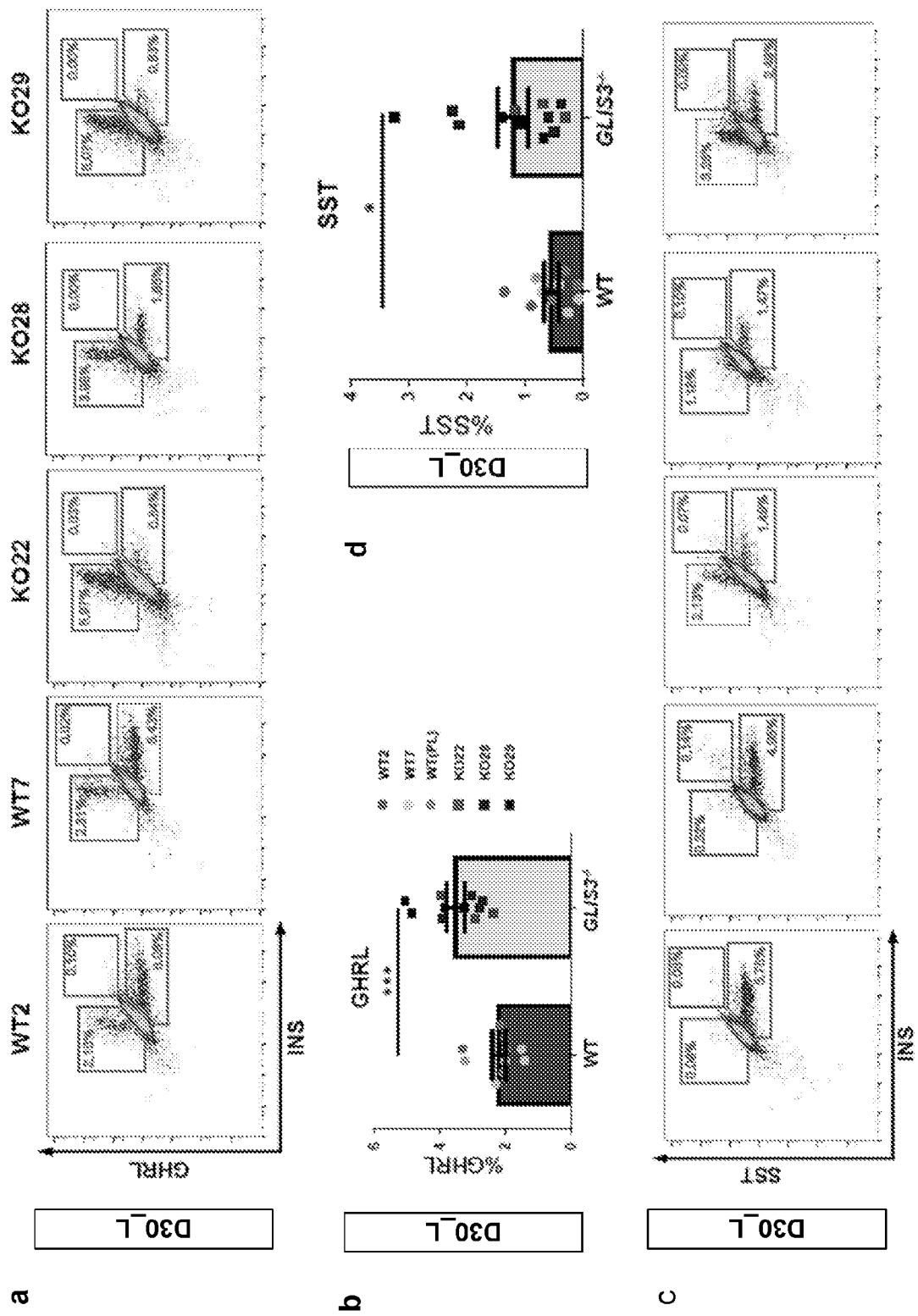
FIG. 9. Characterization of GLIS3−/− endocrine cells at D30_L. (a) Intracellular flow cytometry analysis of INS and GHRL expression in WT and GLIS3−/− cells at D30_L. (b) Quantification of the percentage of GHRL+ cells in WT and GLIS3−/− cells at D30_L (WT n=10, GLIS3−/− n=12). (c) Intracellular flow cytometry analysis of INS and SST expression in WT and GLIS3−/− cells at D30_L. (d) Quantification of the percentage of SST+ cells in WT and GLIS3−/− cells at D30_L. (WT n=10, GLIS3−/− n=12). (e) Intracellular flow cytometry analysis of INS and GCG expression in WT and GLIS3−/− cells at D30_L. (f) Quantification of the percentage of GCG+ cells in WT and GLIS3−/− cells at D30_L. (WT n=12, GLIS3−/− n=14). (g) Immunocytochemistry analysis of INS and CHGA expression in WT and GLIS3−/− cells at D30_L. Scale bar=100 µm. (h) Quantification of the percentage of CHGA+ cells in WT and GLIS3−/− cells at D30_L. The values are normalized to the WT mean. (i, j) Relative number of GHRL+ (i) and SST+ cells in WT and GLIS3−/− cells at D30_L. Data are normalized to WT values (WT n=4, GLIS3−/− n=5). (k) qRT-PCR analysis of INS expression in FACS-purified WT and GLIS3−/− INS-GFP+ PP2-β cells (WT n=3, GLIS3−/− n=2). (l) Glucose-stimulated c-peptide secretion assay of WT and GLIS3−/− cells at D30_L. The data represents the fold change of c-peptide secretion in 20 mM (high) glucose condition vs. 2 mM (low) glucose condition. (m) C-peptide secretion in response to other β-cell secretagogues is shown for the GLIS3−/− cells at D30_L. The data represents the fold change of insulin secretion with 30 mM KCl or 30 µM Forskolin or 10 mM Arginine relative to KRBH treatment (n=5). P values by unpaired two-tailed t-test were *P<0.05, P<0.01, *P<0.001, ****P<0.0001. The center value is "mean". Error bar is SEM.
Figure 9:
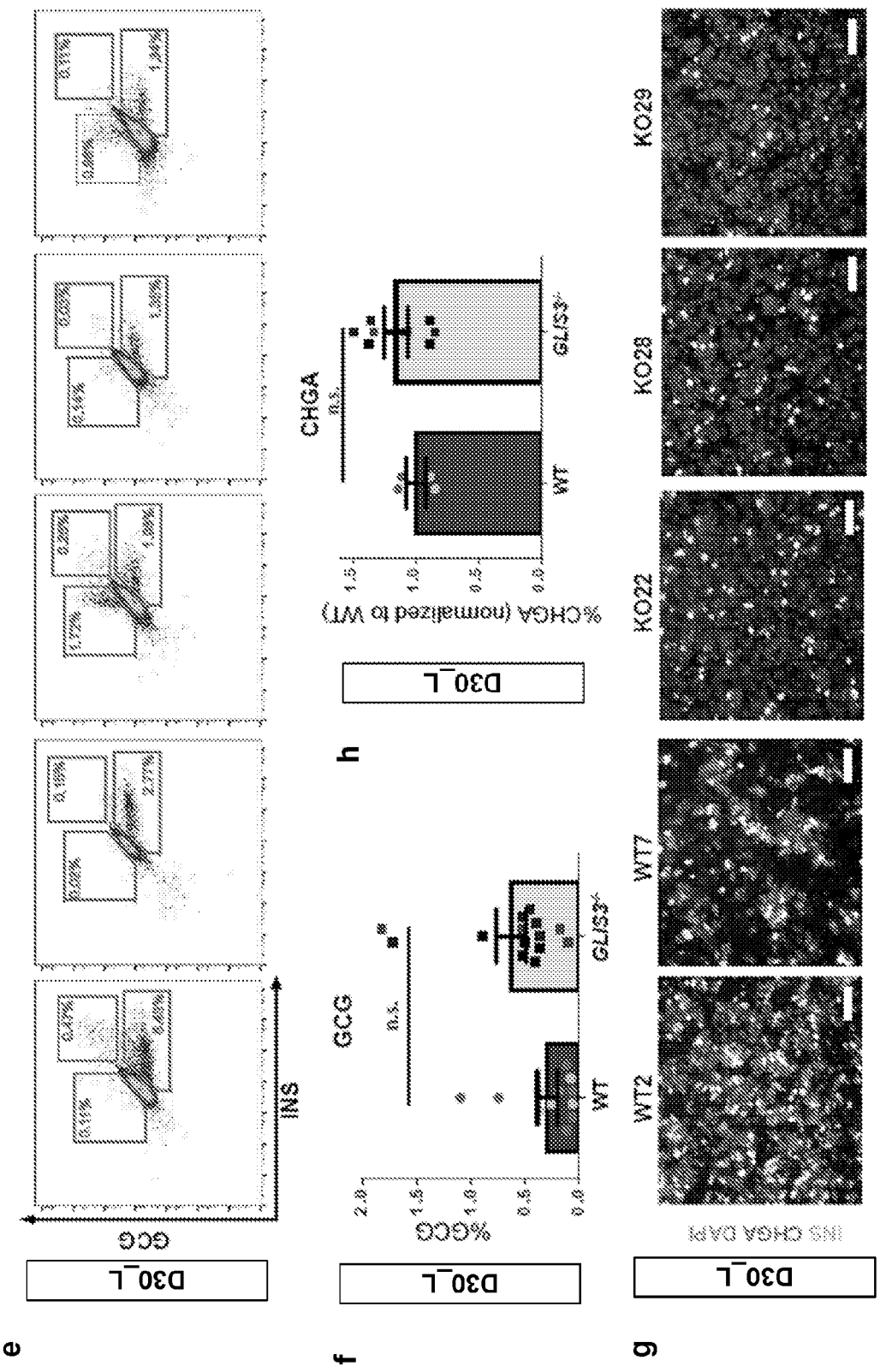
Figure 9:
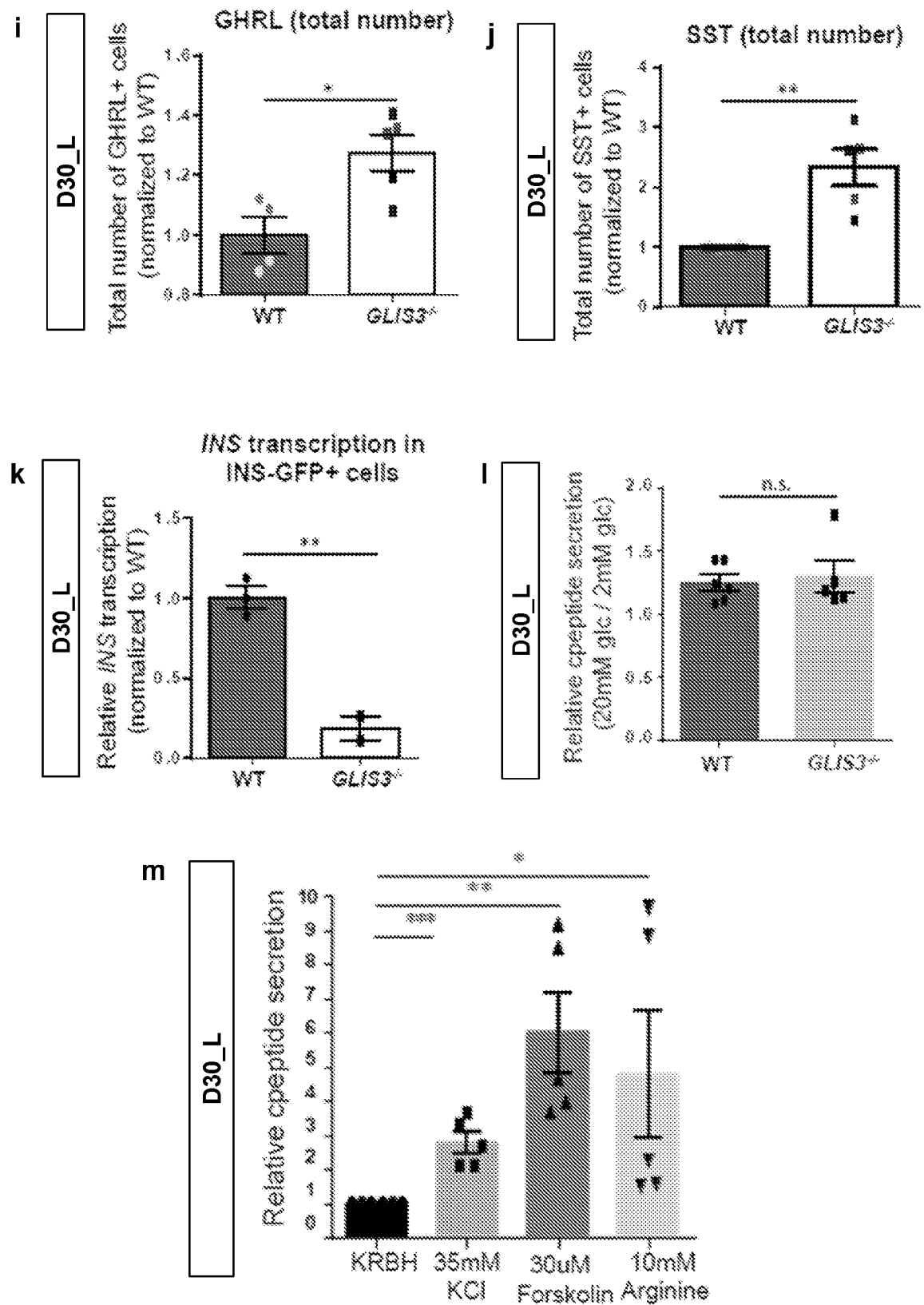

To determine whether loss of GLIS3 affects endocrine differentiation capacity, isogenic WT and GLIS3$^{-/-}$ hESCs were differentiated to D30_L and monitored for the expression of endocrine hormones. First, flow cytometry was used to quantify the percentage of INS-GFP$^+$ cells. A significant decrease of INS$^+$ cells was measured in the GLIS3$^{-/-}$ cells at D30_L (FIG. 2f, 2g). Intracellular flow cytometry and immunocytochemistry analyses for INS further validated the decrease of INS$^+$ cells in the GLIS3$^{-/-}$ cells at D30_L (FIG. 2h, 2k). In contrast, both percentage and absolute number of GHRL$^+$ cells (FIG. 9a, 9b, 9i) and SST$^+$ cells were significantly increased in the GLIS3$^{-/-}$ cells at D30_L (FIG. 9c, 9d, 9j). There was no significant change in GCG$^+$ cells (FIG. 9e, 9f). The percentage of total endocrine-like cells (GCG$^+$+INS$^+$+SST$^+$+GHRL$^+$) was not significantly different between WT and GLIS3$^{-/-}$ cells at D30_L (FIG. 2i). Similar to earlier stages, there was no significant difference between WT and GLIS3$^{-/-}$ cells at D30_L regarding the percentage of CHGA+ cells (FIG. 9g, 9h). However, the ratio of defined subtypes of endocrine cells changes in the GLIS3$^{-/-}$ population, which compared to WT is comprised of more GHRL$^+$ ε-like cells and SST$^+$ δ-like cells at the expense of INS$^+$ β-like cells, while the GCG$^+$ α-like cells remain unchanged (FIG. 2j). This change of endocrine cell subtype in the GLIS3$^{-/-}$ population was further confirmed by immunocytochemistry analysis (FIG. 2k). Finally, we monitored the function of the derived GLIS3$^{-/-}$ at D30_L and found they respond in a similar manner to their WT counterparts when stimulated with 20 mM glucose and other secretagogues including KCl, Forskolin and Arginine (FIG. 9l, 9m), suggesting that the absence of GLIS3 does not affect glucose sensing or the insulin secretory machinery. However, the median fluorescence intensity of INS staining was significantly decreased in GLIS3$^{-/-}$ INS-GFP$^+$ PP2-β cells compared to WT INS-GFP$^+$ PP2-β cells (FIG. 2l, 2m). Consistently, ELISA using lysates of the purified WT or GLIS3$^{-/-}$ INS-GFP$^+$ PP2-β cells showed significantly lower c-peptide content in GLIS3$^{-/-}$ PP2-β cells (FIG. 2n). This phenomenon could be the result of lower INS transcription, as GLIS3 is known to bind to the INS promoter and activate its expression[30][31]. Indeed, FACS-purified GLIS3$^{-/-}$ INS-GFP$^+$ PP2-β cells had lower expression of the INS mRNA compared to WT cells (FIG. 9k)

Figure 3:
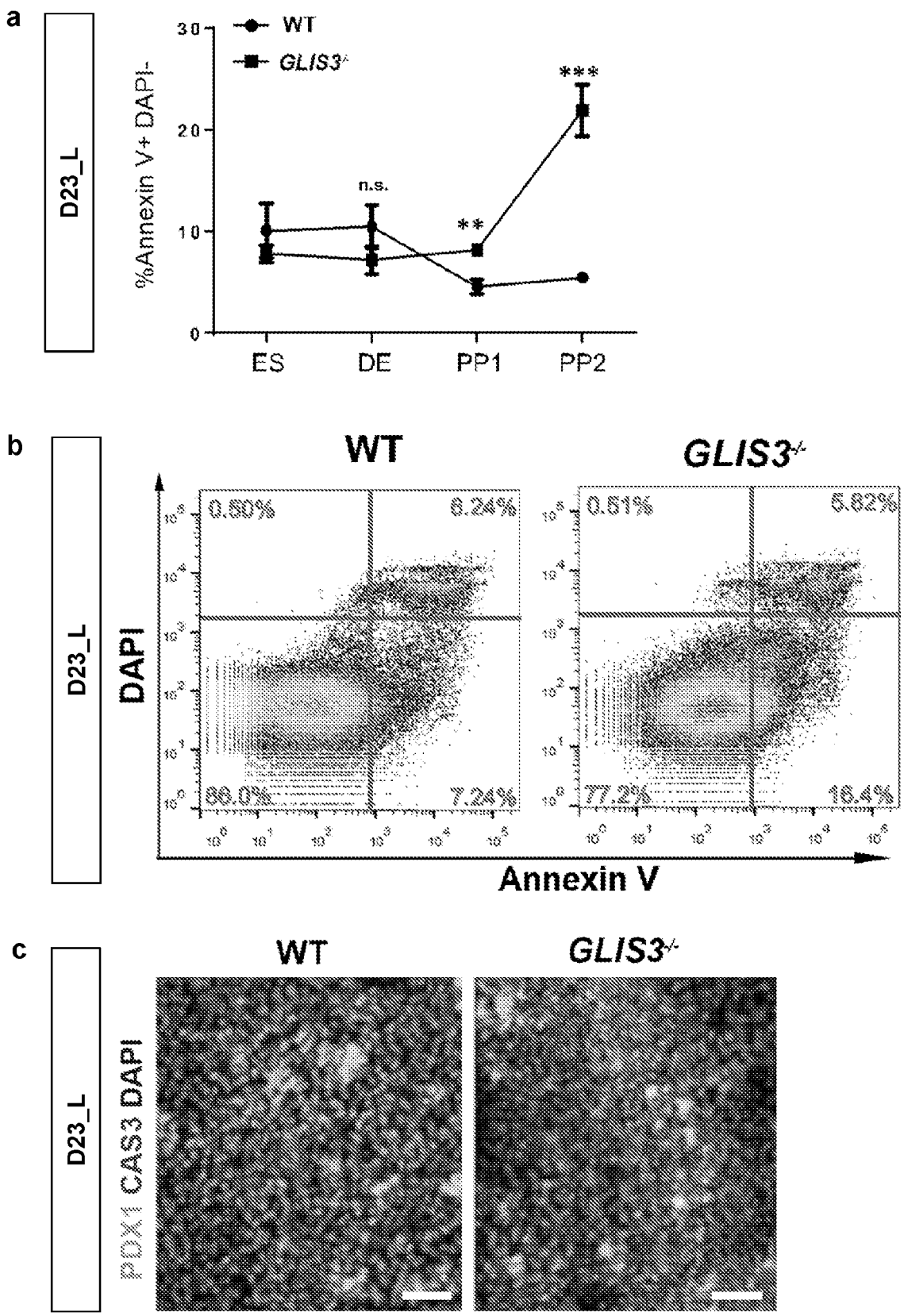
FIG. 3. Loss of GLIS3 leads to increased cell death in PP2 and PP2-β cells. (a) Quantification of early apoptotic cells (the percentage of Annexin V$^+$/DAPI$^-$ cells) in WT and GLIS3$^{-/-}$ ES, DE, PP1 and PP2 cells (n=3). (b) Representative flow cytometry analysis plots of Annexin V staining in WT and GLIS3$^{-/-}$ cells at D23_L. (c) Immunostaining for PDX1 and cleaved caspase-3 in WT and GLIS3$^{-/-}$ cells at D23_L. Scale bar=40 µm. (d, e) Annexin V staining (d) and quantification (e) of early apoptotic cells in the INS-GFP$^+$ cells at D30_L (n=6). (f, g) Histogram showing fluorescence intensity (f) and quantification of median fluorescence values (g) of Annexin V staining of WT and GLIS3$^{-/-}$ INS$^+$ DAPI$^-$ PP2-β cells. (WT n=4, GLIS3$^{-/-}$ n=6). (h) PI, cleaved caspase-3 and INS staining of WT and GLIS3$^{-/-}$ cells at D30_L. Scale bar=40 (i) Quantification of cell death rate (the percentage of PI$^+$INS$^+$ cells in INS$^+$ cells) and apoptosis rate (the percentage of cleaved caspase-3$^+$ INS$^+$ cells in INS$^+$ cells) of WT and GLIS3$^{-/-}$ INS$^+$PP2-β cells (n=3). (j) Schematic representation of an in vivo transplantation experiment. (k) Immunostaining for INS, cleaved caspase-3 and STEM121 in the grafts of mice transplanted with WT or GLIS3$^{-/-}$ cells. Scale bar=100 µm. (l) Quantification of the apoptosis rate (the percentage of cleaved caspase-3$^+$/STEM121$^+$ cells in STEM121$^+$ cells) within WT and GLIS3$^{-/-}$ grafts (n=7 for WT, n=4 for GLIS3$^{-/-}$). (m) Quantification of the percentage of apoptotic INS$^+$ cells (CAS3$^+$PDX1$^+$STEM121$^{30}$) in the INS$^+$ population within the WT and GLIS3$^{-/-}$ grafts (INS$^+$STEM121$^+$, WT n=7, GLIS3$^{-/-}$ n=4). CAS3: cleaved caspase-3. P values by unpaired two-tailed student t-test were *P<0.05, P<0.01, *P<0.001, ****P<0.0001. The center value is "mean". Error bar is SEM.
Figure 3:
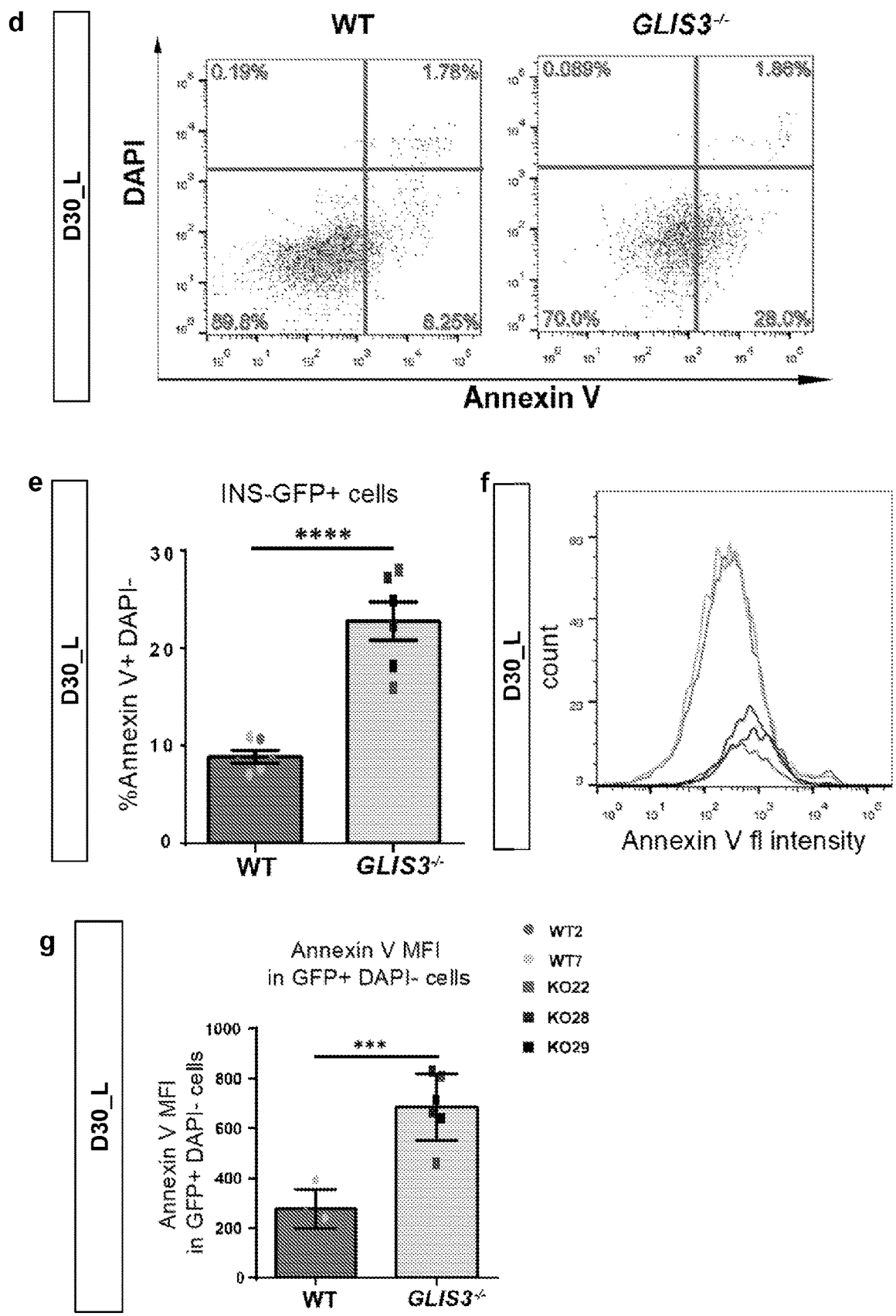
Figure 3:
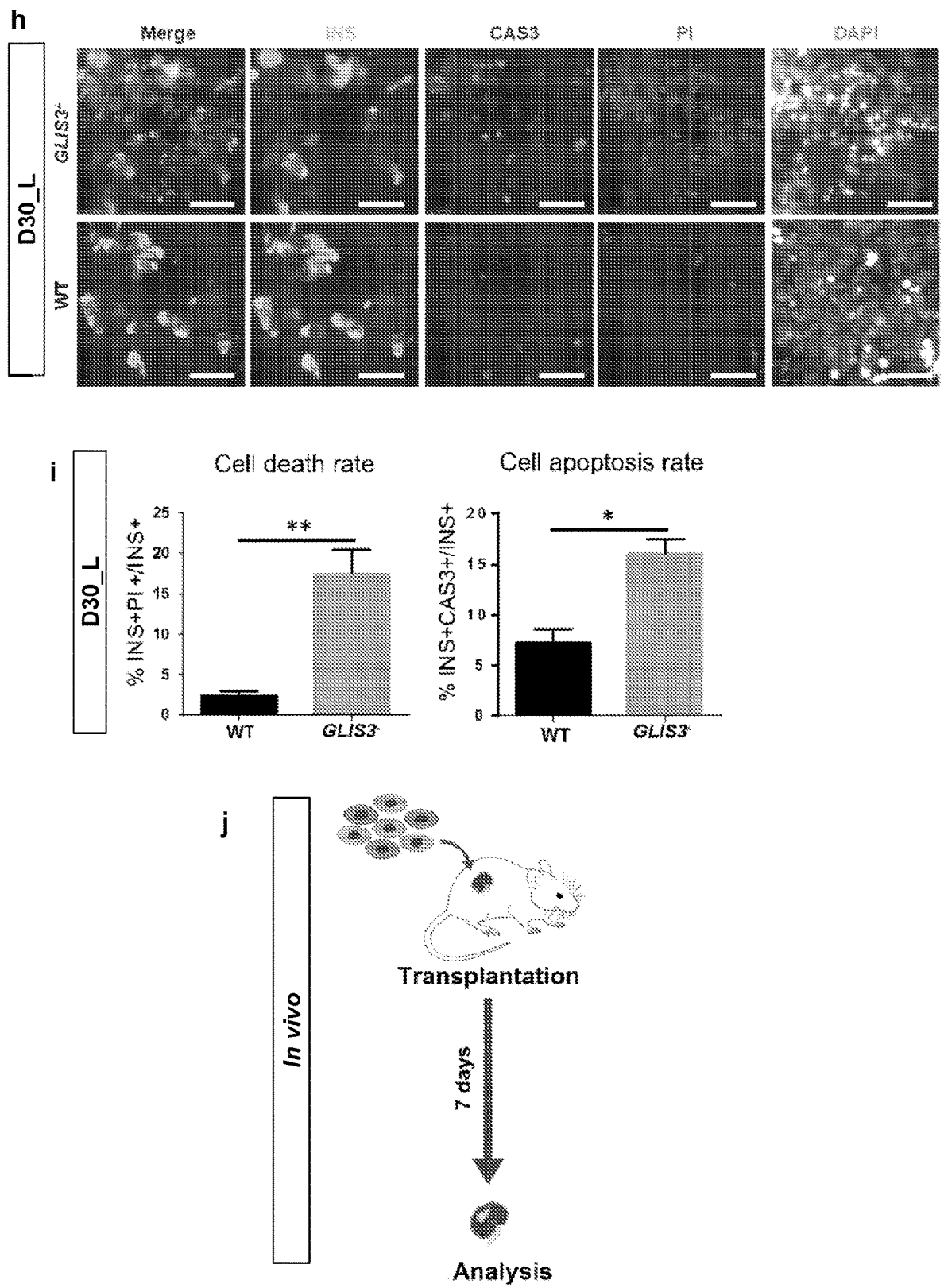
Figure 3:
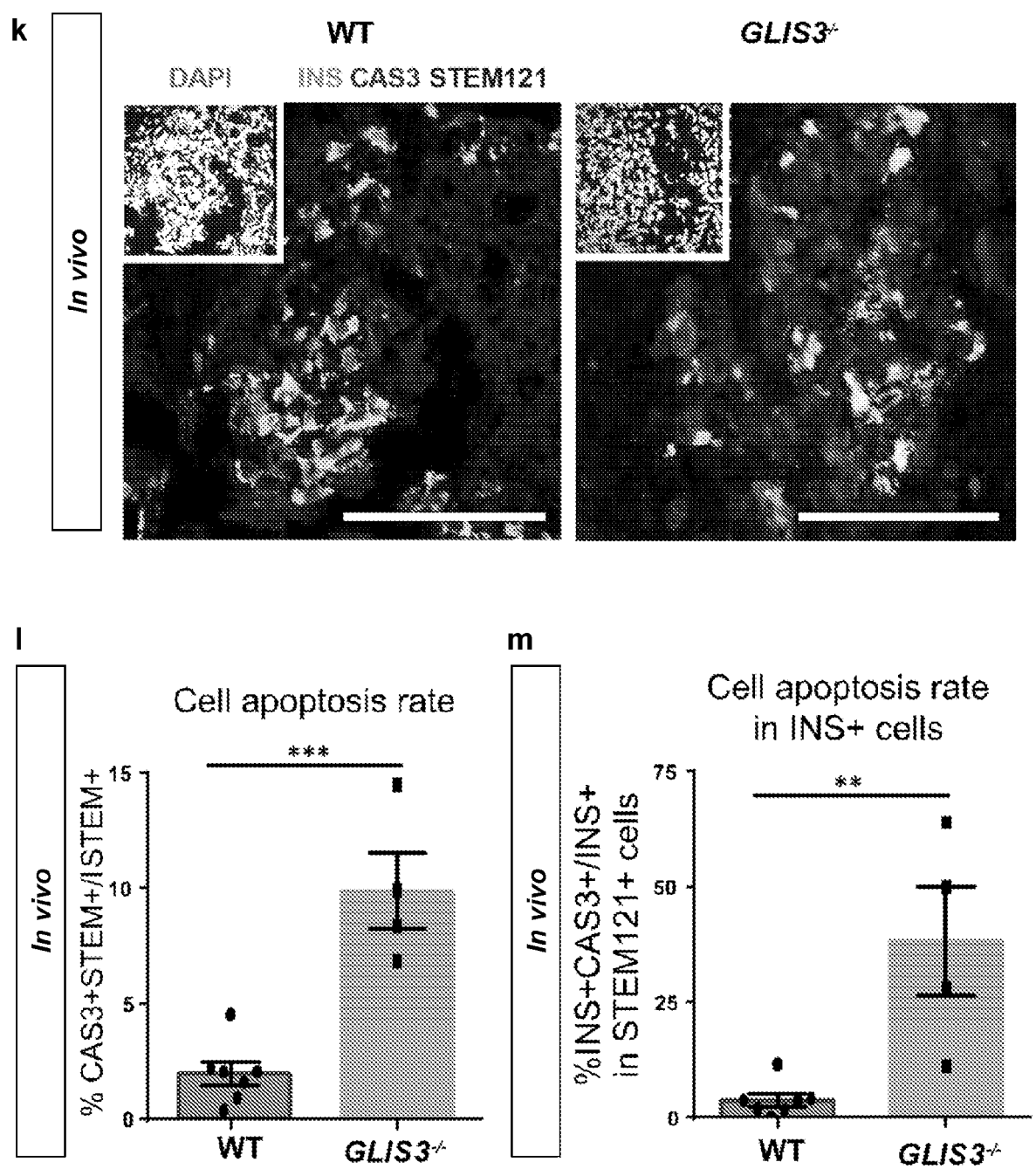
Figure 10:
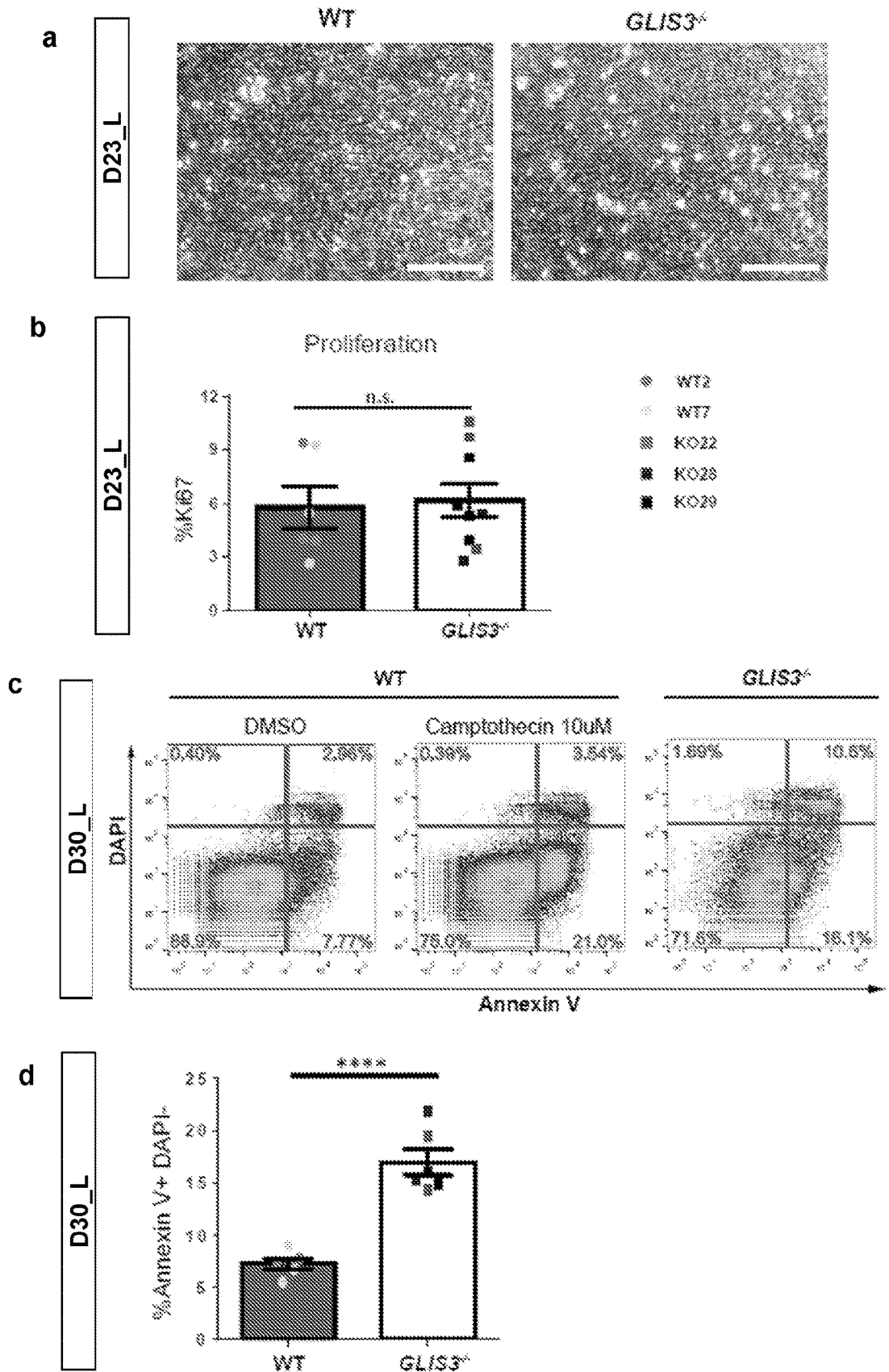
FIG. 10. Quantification of cell death in INS-cells at D23_L and D30_L. (a) Representative transmitted light images of WT and GLIS3−/− cells at D23_L (Scale bar=100 µm). (b) Immunostaining quantification of Ki67+ cells at D23_L (n=6). (c, d) Annexin V staining (c) and the quantification of early apoptotic rate (d, the percentage of Annexin V+/DAPI cells) at D30_L WT+DMSO, WT+10 µM Camptothecin and GLIS3−/− cells (WT n=9, GLIS3−/− n=12). (e) Immunostaining for PDX1, cleaved caspase-3 and INS in WT and GLIS3−/− cells at D30_L. Scale bar=100 µm. (f, g) Quantification of cell death rate (f, the percentage of PI+INS-cells in INS-cells) and apoptosis rate (g, the percentage of cleaved caspase-3+INS-cells in INS-cells) in WT and GLIS3−/− cells at D30_L (n=3). (h) Immunohistochemistry for PDX1, cleaved caspase-3 and STEM121 in WT and GLIS3−/− cells transplanted in vivo. Scale bar=50 µm. (i) quantification of the percentage of apoptotic PDX1+ cells (CAS3+PDX1+STEM121+) in the PDX1+ population within the graft (PDX1+STEM121+, WT n=7, GLIS3−/− n=4). P values by unpaired two-tailed t-test were *P<0.05, P<0.01, *P<0.001, ****P<0.0001. The center value is "mean". Error bar is SEM.
Figure 10:
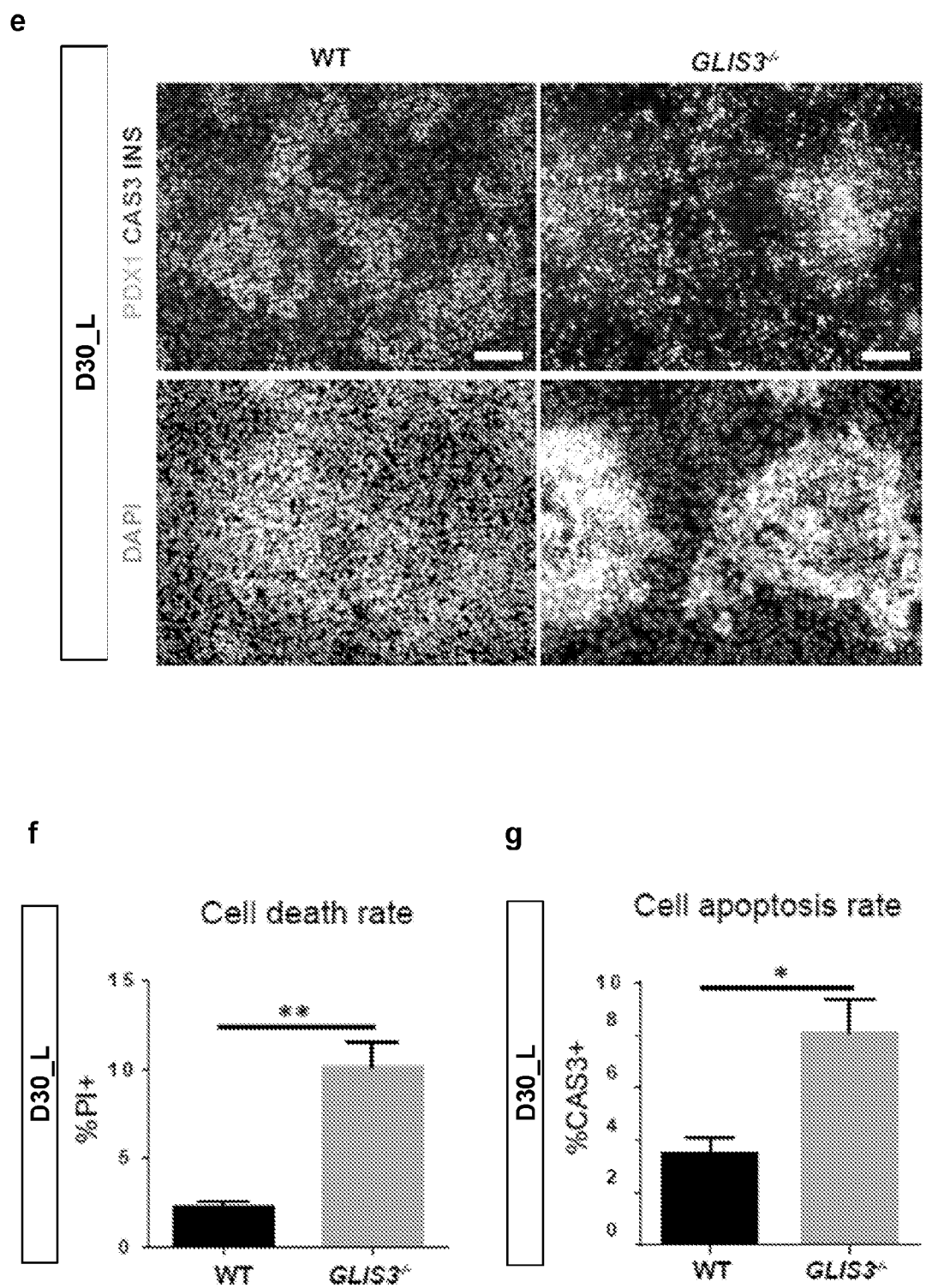

Loss of GLIS3 leads to increased apoptosis. Previous studies showed that knockdown of Glis3 induces apoptosis in a rat β-cell line[32]. Therefore, we assessed the viability of GLIS3$^{-/-}$ hESC-derived cells at different stages throughout the differentiation process. We monitored apoptosis of WT and GLIS3$^{-/-}$ hESCs, DE, PP1 and PP2 cells using Annexin V staining (FIG. 3a). The apoptotic rates of GLIS3$^{-/-}$ hESCs or DE cells arecomparable to WT cells. At D9, there is a modest yet statistically significant higher apoptosis rate in GLIS3$^{-/-}$ PP1 cells compared to WT PP1 cells (8.2%±0.3 vs 4.5%±0.7). The apoptosis rate is exacerbated in GLIS3$^{-/-}$ PP2 cells at D23_L. Around 21.9%±2.5 of GLIS3$^{-/-}$ PP2 cells stained positive for Annexin V, which is significantly higher than for WT PP2 cells (5.5%±0.4, FIG. 3a-3c). To interrogate whether the increased apoptosis was a consequence of overcrowding, we measured proliferation rate of PP2 cells. There was no significant difference in the confluency or proliferation rate between GLIS3$^{-/-}$ and WT PP2 cells (FIG. 10a, 10b). The percentage of Annexin V$^+$ cells and intensity of annexin V staining are likewise significantly higher in the GLIS3$^{-/-}$ INS-GFP$^+$ PP2-β cells compared to WT INS-GFP$^+$ PP2-β cells (GLIS3$^{-/-}$: 22.7±2.0% vs WT: 13.9±2.1%, FIG. 3d-3g). Immunocytochemistry analysis using antibodies to stain INS, cleaved caspase-3 in addition to PI further confirmed the higher cell death rate (the percentage of PI$^+$INS$^+$ cells in INS$^+$ cells) and cell apoptosis rate (the percentage of cleaved caspase-3$^+$ INS$^+$ cells in INS$^+$ cells, FIG. 3h, 3i) in GLIS3$^{-/-}$ INS-GFP$^+$ PP2-β cells than those in in WT INS-GFP$^+$ PP2-β cells. Similar to GLIS3$^{-/-}$ INS-GFP$^+$ PP2-β cells, the GLIS3$^{-/-}$ INS-GFP$^+$ cells at D30_L show higher cell death and apoptosis compared to WT INS-GFP$^-$ cells (FIG. 10c-10g); the majority of the INS$^-$ cells at D30_L are undifferentiated PDX1$^+$ cells (FIG. 10e). Intriguingly, the decrease of cellular viability in the GLIS3$^{-/-}$ cells correlates closely with expression of GLIS3 during the differentiation process (FIG. 1b), suggesting an essential role for GLIS3 for the survival of PP2 and PP2-β cells. To determine whether loss of GLIS3 leads to increased apoptosis of cells in vivo, WT or GLIS3$^{-/-}$ cells at D23_L were transplanted under the kidney capsule of 6-8 weeks old male SCID-beige mice (FIG. 3j). The mice were sacrificed after seven days and the grafts were examined for apoptosis by staining for cleaved caspase-3. Human cells were identified by labeling for human cytoplasmic marker STEM121. Consistent with our in vitro results (FIG. 3a-3i), a significantly increased cell apoptosis rate (the percentage of cleaved caspase-3$^+$/STEM121$^+$ cells in STEM121$^+$ cells, FIG. 3k, 3l) was detected in the grafts of mice transplanted with GLIS3$^{-/-}$ cells. Furthermore, the cell apoptotic rate in INS$^+$ and PDX1$^+$ cells of the GLIS3$^{-/-}$ grafts is higher than for WT grafts. (FIG. 3m and FIG. 10h, 10i).

Figure 4:
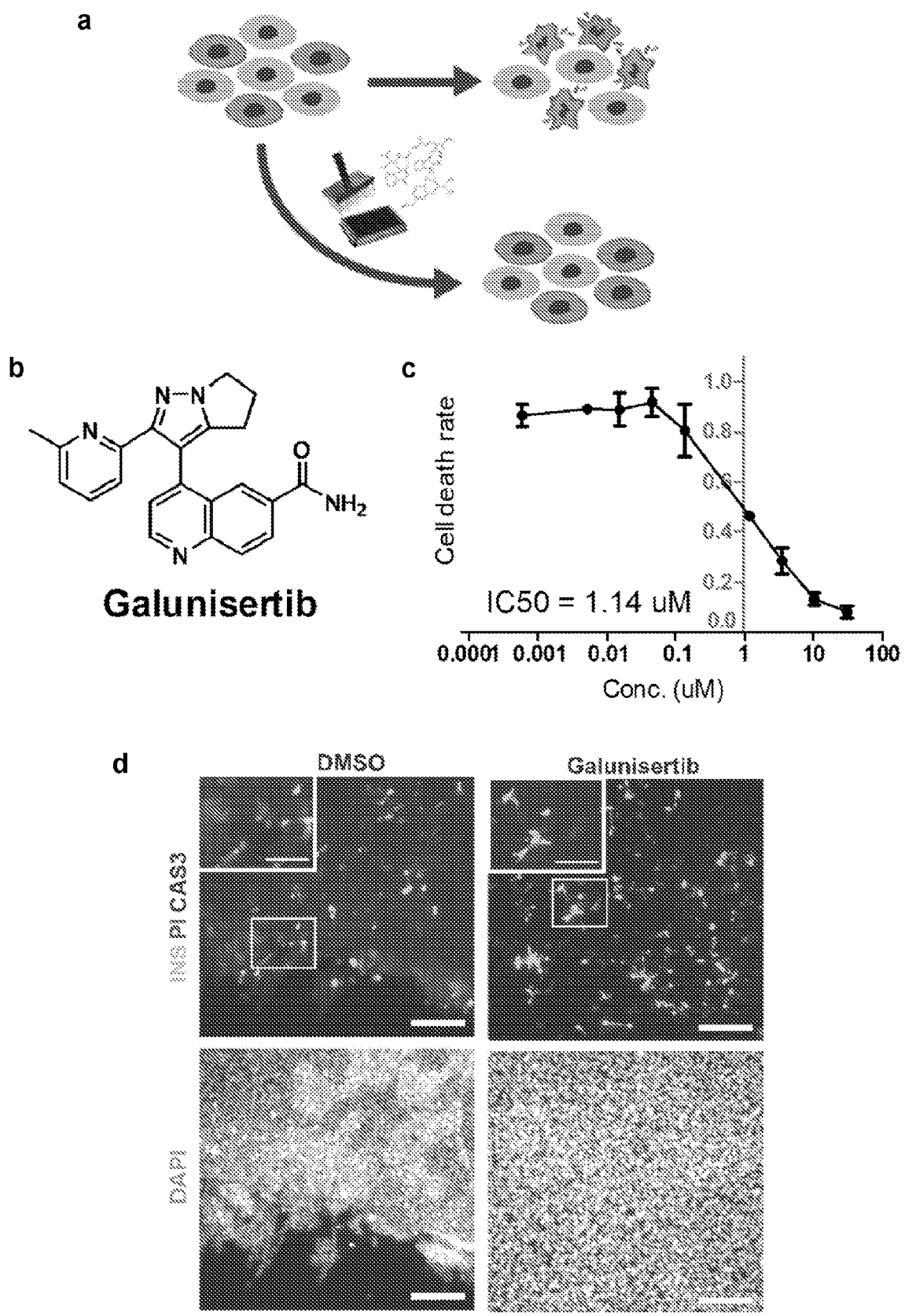
FIG. 4. A high content chemical screen identifies galunisertib as a drug candidate to rescue cell death induced by loss of GLIS3 both in vitro and in vivo. (a) Schematic representation of the high content chemical screen. (b) Chemical structure of galunisertib. (c) Inhibitory curve of galunisertib. (d) Immunocytochemistry analysis of GLIS3$^{-/-}$ PP2-β cells treated with DMSO or 10 µM galunisertib. Scale bar=100 µm, scale bar of high magnification insets=40 µm. (e, f) Quantification of the cell death rate (e, the percentage of PI$^+$ INS$^+$ cells in INS$^+$ cells, n=4) and apoptosis rate (f, the percentage of cleaved caspase-3$^+$INS$^+$ cells in INS$^+$ cells, n=3) of GLIS3$^{-/-}$ PP2-β cells treated with DMSO or 10 µM galunisertib. (g, h) Flow cytometry analysis (g) and quantification (h) of early apoptotic cells (the percentage of Annexin V$^+$/DAPI$^-$ cells) in GLIS3$^{-/-}$ INS-GFP$^+$ PP2-β cells treated with DMSO or 10 µM galunisertib (n=6). (i) Relative number of INS$^+$ cells in GLIS3$^{-/-}$ PP2-β cells treated with DMSO or 10 µM galunisertib. Data are normalized to DMSO-treated values (n=4). (j) Schematic representation of the in vivo transplantation and drug treatment experiments. (k) Immunohistochemistry analysis of INS, cleaved caspase-3 and STEM121 in the grafts isolated from vehicle- or galunisertib-treated mice. Scale bar=100 µm. (l) Quantification of immunohistochemistry data in (j) (n=7). (m) Quantification of the percentage of apoptotic INS$^+$ cells (CAS3$^+$PDX1$^+$STEM121$^+$) in the INS$^+$ population within the grafts from vehicle- or galunisertib-treated mice (INS$^+$STEM121$^+$, n=6). CAS3: cleaved caspase-3. P values by unpaired two-tailed t-test were *P<0.05, P<0.01, *P<0.001, ****P<0.0001. The center value is "mean". Error bar is SEM.
Figure 4:
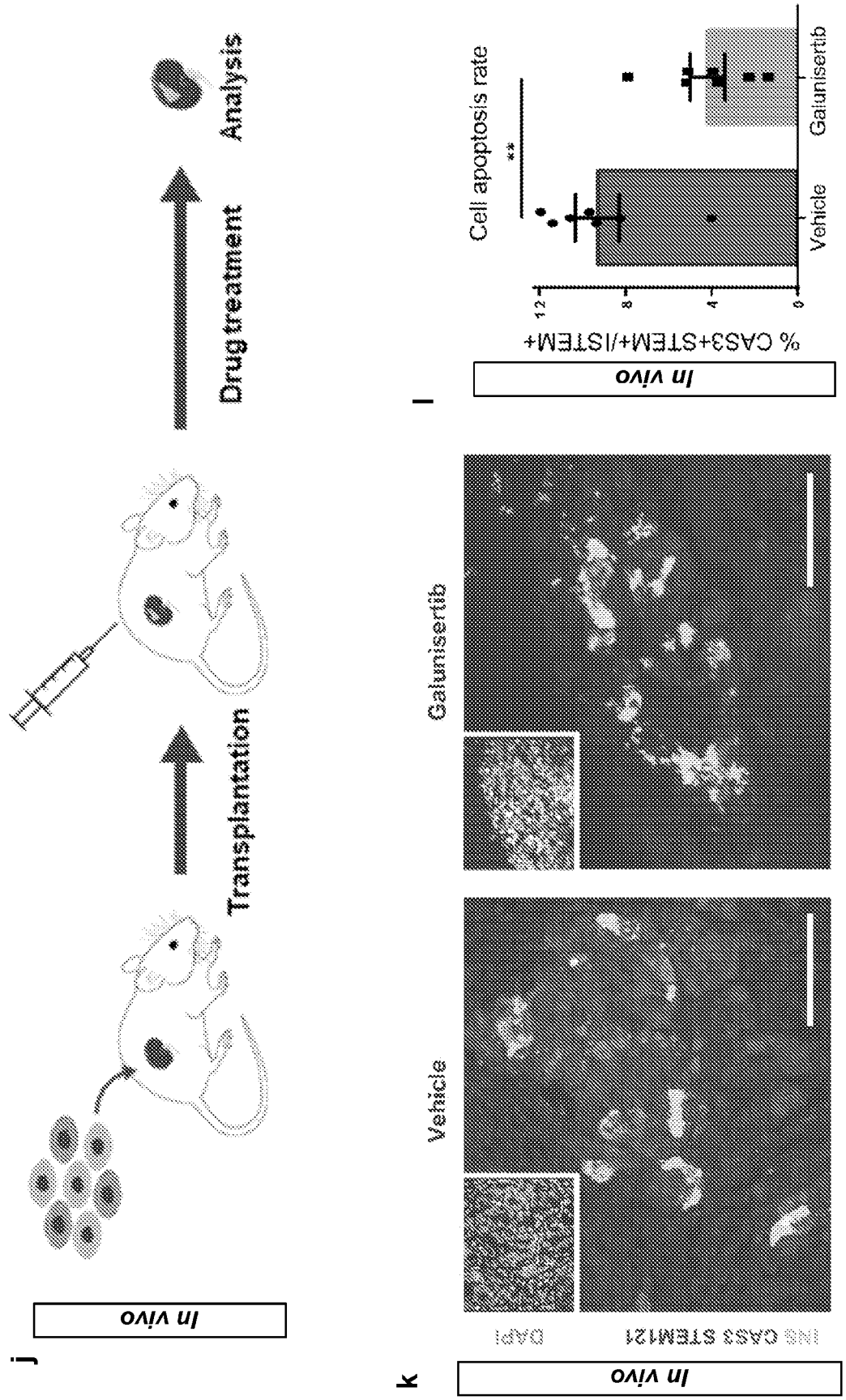
Figure 11:
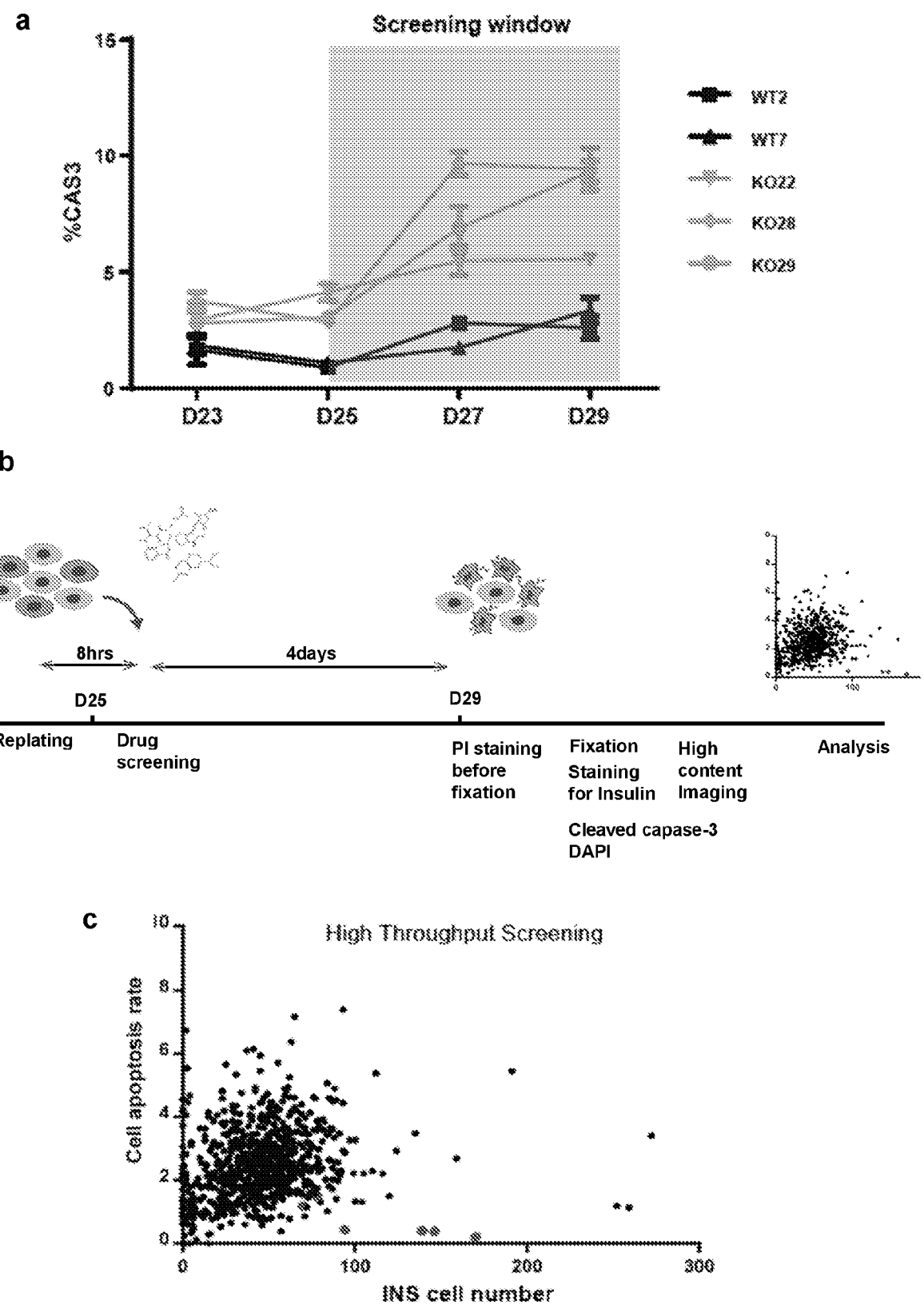
FIG. 11. Design and primary results of the high throughput drug screen. (a) Time-course staining to monitor the percentage of cleaved caspase-3+ cells in WT and GLIS3−/− cells to optimize the window for drug screening (n=2). (b) Schematic representation of the screening process. (c) Representative dot plot of the primary screening results. Dots show confirmed hits.
Figure 12:
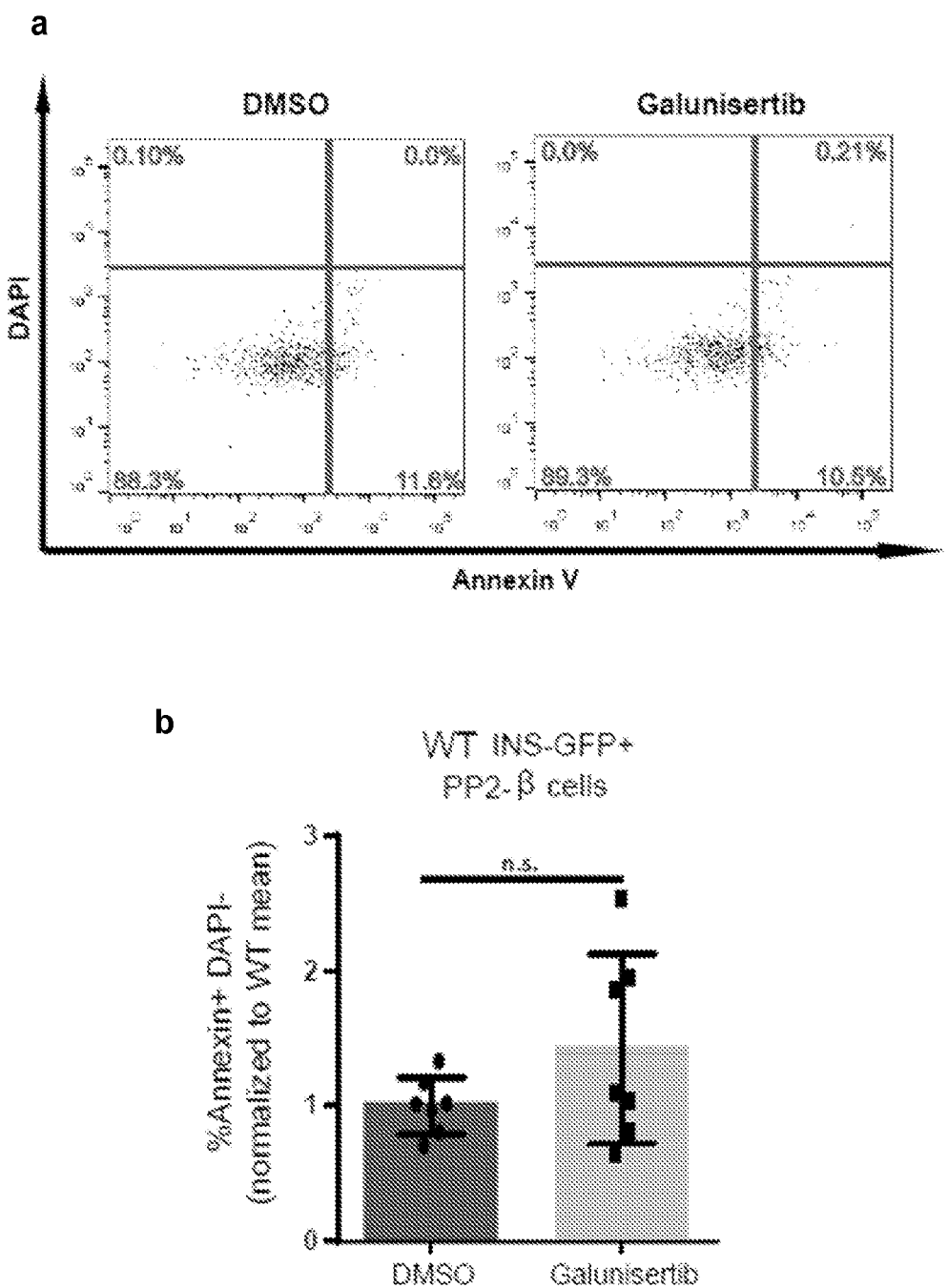
FIG. 12. Galunisertib does not affect cell apoptosis of WT PP2-β cells. (a,b) Flow cytometry analysis (a) and quantification of the percentage (b) of Annexin V+ cells in WT INS-GFP+ PP2-β treated with DMSO or 10 µM galunisertib (n=7). n.s. not significant. The center value is "mean". Error bar is SEM.
Figure 13:
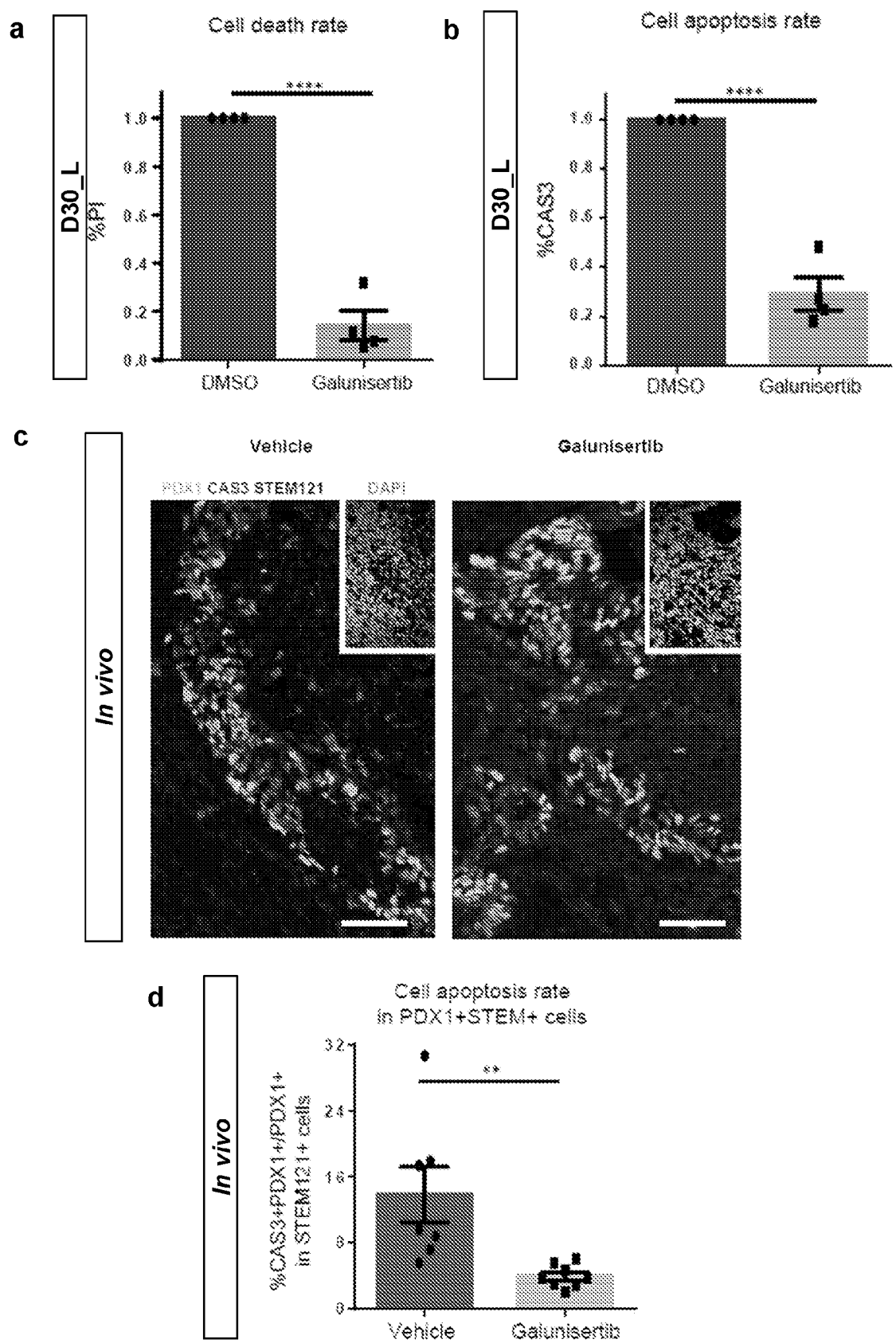
FIG. 13. Effect of galunisertib and other TGFβ inhibitors on INS-GLIS3−/− at D30_L. (a, b) Quantification of the cell death rate (a, the percentage of PI+ cells) and apoptosis rate (b, the percentage of cleaved caspase-3+ cells) of GLIS3−/− cells at D30_L treated with galunisertib or DMSO (n=4). (c) Immunohistochemistry for PDX1, cleaved caspase-3 and STEM121 in GLIS3−/− grafts treated with vehicle or galunisertib. Scale bar=50 µm. (d) Quantification of the percentage of apoptotic PDX1+ cells (CAS3+PDX1+STEM121+) in the PDX1+ population within the graft (PDX1+STEM121+, vehicle n=7, galunisertib n=8). P values by unpaired two-tailed t-test were P<0.01, *P<0.001, ****P<0.0001. The center value is "mean". Error bar is SEM.

Galunisertib rescues apoptosis induced by loss of GLIS3. Loss of function mutations in GLIS3 cause neonatal diabetes' and increased cell death caused by GLIS3 mutations may also contribute to T1D and T2D. Having access to the disease-relevant cells presenting a clear disease phenotype, we carried out a high content chemical screen to identify drug candidates that can rescue the increased cell death in GLIS3$^{-/-}$ cells. First, we performed a time course experiment to optimize the time window for the chemical screen and determined that cell apoptosis significantly increases from day 25 to day 29 of the differentiation protocol (FIG. 11a). Thus, the screen was carried out from day 25 to day 29 to identify drug candidates that block cell apoptosis induced by loss of GLIS3. To perform the screen, GLIS3$^{-/-}$ cells at D25_L were replated in 384 well plates and then exposed to compounds from multiple chemical libraries, including FDA approved drugs and drugs in clinical trials, kinase inhibitors, signaling pathway modulators and other annotated compounds. These compounds were added at 1 or 10 µM for four days followed by high content microscopy and analysis to determine the number of apoptotic and INS$^+$ cells post exposure (FIG. 4a and FIG. 11b). In the DMSO-treated condition, the percentage of cleaved caspase-3$^+$ cells was 12.6±0.9%. Compounds that decreased the percentage of cleaved caspase-3$^+$ cells by at least 2.5-fold (z score≤−1.5) were picked as primary hits. After screening ~5000 compounds, we identified 23 primary hit compounds that prevented the increased cell death in GLIS3$^{-/-}$ INS-GFP$^+$ PP2-β cells (FIG. 11c and Table 8). The Z' factor of the primary screen was 0.52. The signal to basal ratio was 0.2 with a coefficient of variation 0.39. The hit rate was ~0.45%. After several rounds of hit confirmation, we focused on one compound, galunisertib (LY2157299), that showed the highest efficacy and replicability (FIG. 4b). Galunisertib efficiently rescues loss of GLIS3-induced pancreatic β-cell apoptosis in a dose-dependent manner (IC50: 1.14 µM, FIG. 4c). Treatment of cells with 10 µM galunisertib significantly reduces cell death (FIG. 4d, 4e and FIG. 13a) and cell apoptosis (FIG. 4d, 4f-4h and FIG. 13b) in GLIS3$^{-/-}$ cells at D30_L. Consistently, galunisertib treatment increases the number of INS$^+$ cells (FIG. 4i). We also tested galunisertib using WT INS-GFP$^+$ PP2-β cells. Galunisertib does not affect cell apoptosis of WT INS$^+$ cells, showing that the rescue effect of galunisertib is specific to GLIS3$^{-/-}$ cells (FIG. 12a, 12b).

We further tested galunisertib in vivo. GLIS3$^{-/-}$ PP2 cells were pre-treated with 10 µM galunisertib for 16 hr and then transplanted under the kidney capsule of 6-8 weeks old male SCID-beige mice (FIG. 4j). The mice were randomly separated into two groups and treated with either 15 mg/kg/day of galunisertib or vehicle by intraperitoneal injection for seven days. The mice were euthanized and the grafts were analyzed for cell apoptosis. Galunisertib treatment significantly decreases the cell apoptosis rate in the transplanted cells (the percentage of cleaved caspase-3$^+$/STEM121$^+$ cells in STEM121$^+$ cells, FIG. 4k, 4l) and more specifically in INS$^+$ and PDX1$^+$ cells in the grafts (FIG. 4m and FIG. 13c, 13d), showing that in vivo galunisertib can rescue cell death induced by loss of GLIS3.

Figure 5:
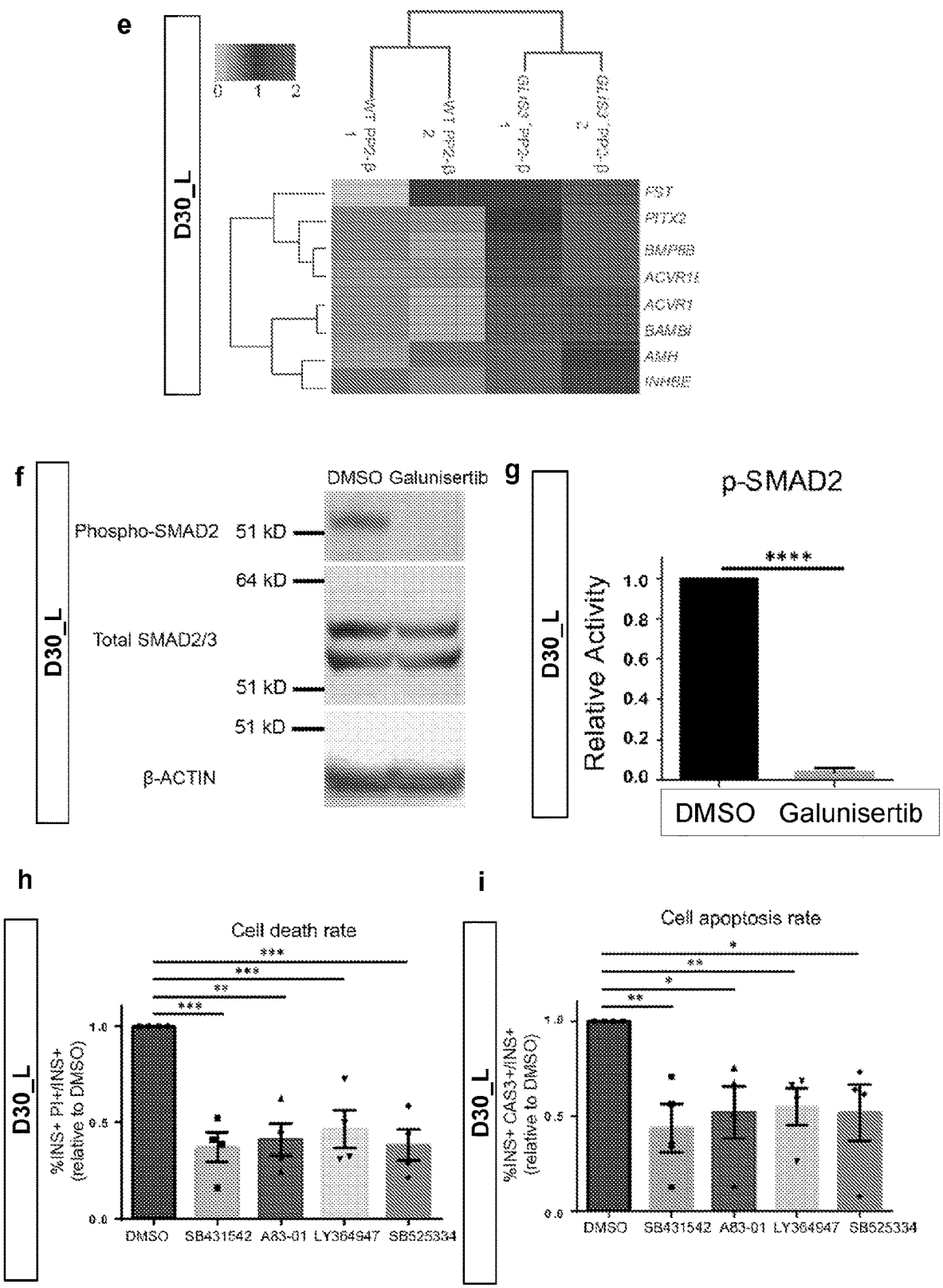
FIG. 5. Galunisertib rescues loss of GLIS3 induced cell death by inhibiting TGFβ signaling. (a, b) KEGG pathway analysis (a) and gene ontology (GO) analysis (b) of genes that are significantly (P<0.01) upregulated in in GLIS3$^{-/-}$ PP2 cells. (c, d) Western blot analysis (c) and quantification (d, n=3) of SMAD2/3 phosphorylation in WT and GLIS3$^{-/-}$ cells at D23_L. (e) Heatmap representing the relative expression levels of TGF-β-related genes upregulated at least two-fold in the purified WT and GLIS3$^{-/-}$ INS-GFP$^+$ PP2-β cells. (f, g) Western blotting analysis (f) and quantification (g, n=3) of SMAD2 phosphorylation in GLIS3$^{-/-}$ cells at D30_L treated with DMSO or 10 µM galunisertib. (h, i) Quantification of the cell death rate (h, the percentage of PI$^{30}$ INS$^+$ cells in INS$^+$ cells) and apoptosis rate (i, the percentage of cleaved caspase-3$^+$INS$^+$ cells in INS$^+$ cells) of GLIS3$^{-/-}$ PP2-β cells treated with different TGFβ inhibitors (n=4). CAS3: cleaved caspase-3. P values by unpaired two-tailed t-test were *P<0.05, P<0.01, *P<0.001, ****P<0.0001. The center value is "mean". Error bar is SEM.
Figure 14:
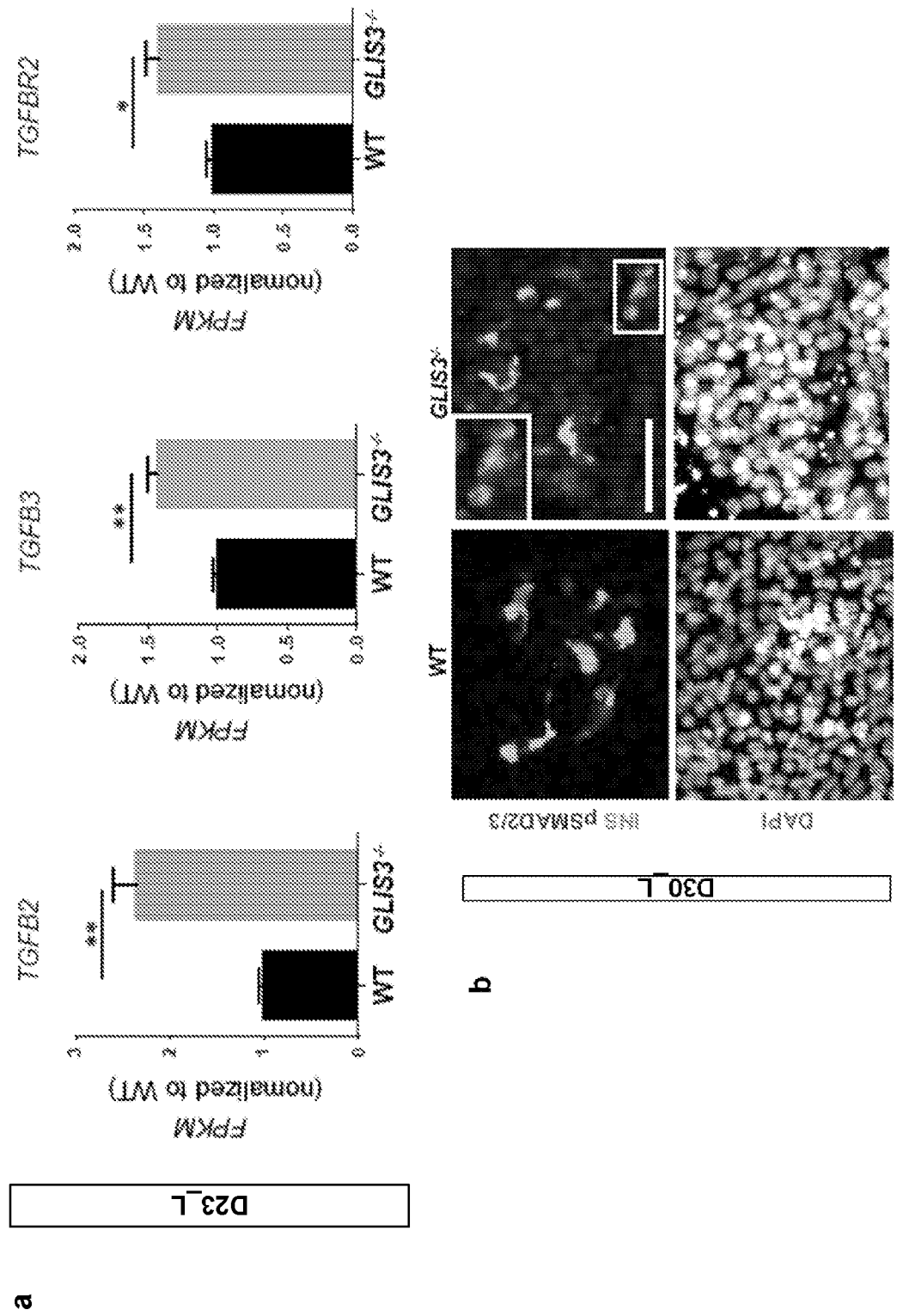
FIG. 14. GLIS3−/− pancreatic cells display increased TGFβ signaling. (a) FPKM values for TGFβ genes TGFB2, TGFB3 and TGFBR2 in WT and GLIS3−/− PP2 cells (n=3). (b) Immunostaining for pSMAD/3 and insulin WT and GLIS3−/− PP2-β cells. Scale bar=50 µm. (c) Ingenuity pathway analysis prediction of TGFβ signaling pathway activity in the WT and GLIS3−/− INS-GFP+ PP2-β cells. (d, e) Quantification of the cell death rate (d, the percentage of PI+ cells) and cell apoptosis rate (e, the percentage of cleaved caspase-3+ cells) of GLIS3−/− cells at D30_L treated with the indicated TGFβ inhibitors (n=4). P values by unpaired two-tailed t-test were P<0.01, *P<0.001, ****P<0.0001. The center value is "mean". Error bar is SEM.
Figure 15:
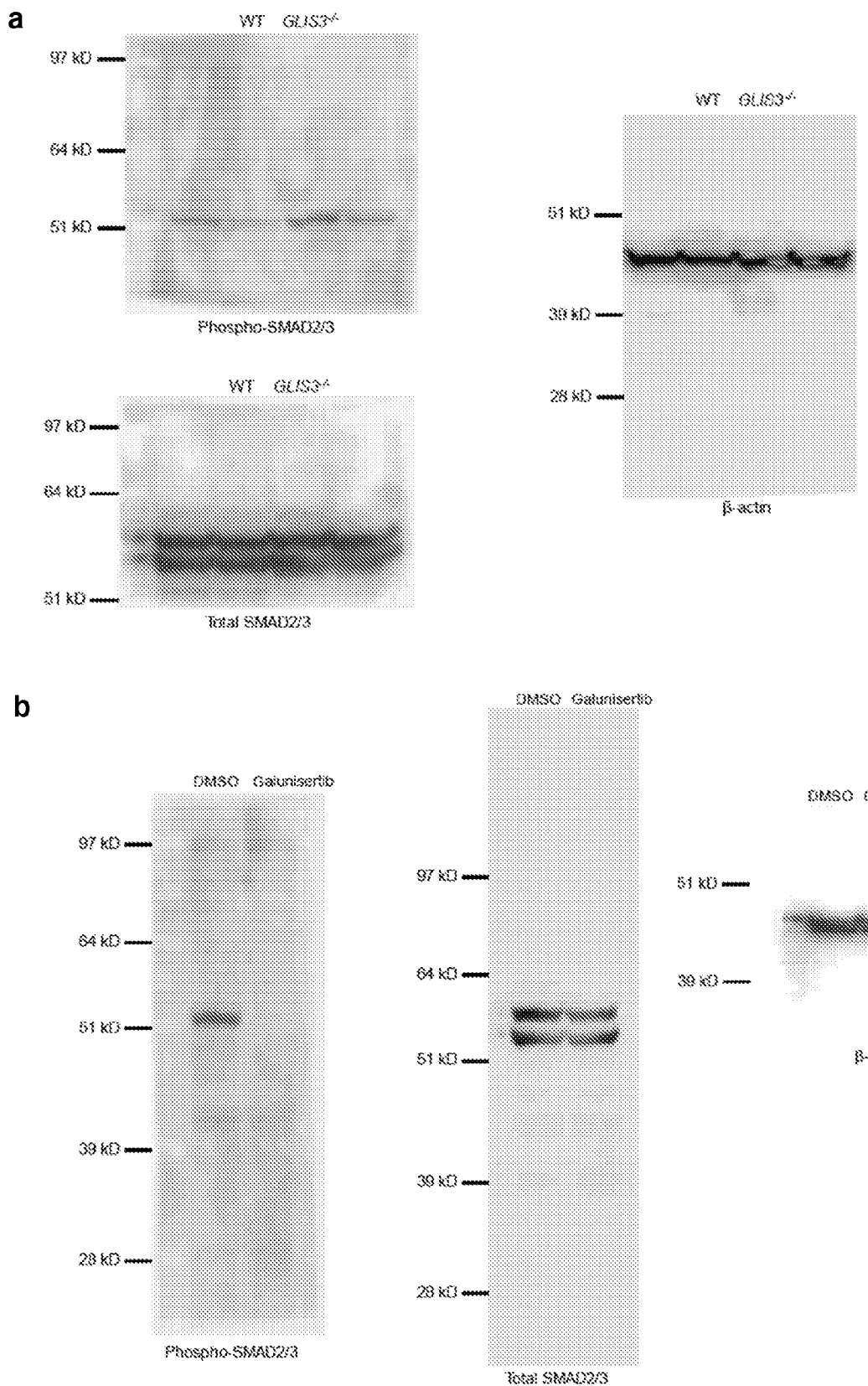
FIG. 15. Uncropped western blots of FIG. 5. (a) Related to FIG. 5c. (b) Related to FIG. 5f.

Loss of GLIS3 causes cell death by activating TGFβ pathway. Galunisertib was previously developed as a TGFβR 1 kinase inhibitor. To investigate the mechanism of action, we used RNA-seq profiling to compare the WT and GLIS3$^{-/-}$ PP2 cells. KEGG pathway analysis (FIG. 5a) highlights the upregulation of the TGFβ signaling pathway in GLIS3$^{-/-}$ PP2 cells while gene ontology analysis (FIG. 5b) further validates the upregulation of positive regulation of pathway restricted SMAD protein phosphorylation and SMAD protein signal transduction in GLIS3$^{-/-}$ PP2 cells. We observed significant upregulation in key genes involved in TGFβ activation including TGFB2, TGFB3 and TGFBR2 (FIG. 14a). Together, these data point to an upregulation of the TGFβ pathway in GLIS3$^{-/-}$ PP2 cells. Western blotting confirmed an increased SMAD2 phosphorylation level in GLIS3$^{-/-}$ PP2 cells (FIG. 5c, 5d and FIG. 15). Importantly, pSMAD2/3 staining co-localizes with INS in GLIS3$^{-/-}$ PP2-β cells (FIG. 14b). RNA-seq profiling of FACS-purified INS-GFP$^+$ WT and GLIS3$^{-/-}$ PP2-β cells confirmed the relative upregulation of TGFβ pathway related genes in the GLIS3$^{-/-}$ PP2-β cells (KEGG pathway analysis, P-value<0.05, FIG. 5e). Ingenuity Pathway Analysis predicts upregulation of the TGFβ pathway in GLIS3$^{-/-}$ PP2-β cells (FIG. 14c). Galunisertib inhibits the increased SMAD2/3 phosphorylation in GLIS3$^{-/-}$ cells at D30_L (FIG. 5f, 5g and FIG. 15). Finally, we tested other TGFβ inhibitors. Consistent with galunisertib, a range of TGFβ inhibitors, including 1 µM SB431642, 10 µM A83-01, 1 µM SB525334 and 10 µM LY-364947, significantly decrease the cell death and cell apoptosis rates in INS-GFP$^+$ GLIS3$^{-/-}$ PP2-β cells (FIG. 5h, 5i and Table 9). These TGFβ inhibitors also prevent increased cell apoptosis and cell death in INS$^-$ GLIS3$^{-/-}$ cells at D30_L, which are mainly undifferentiated PDX1$^+$ cells (FIG. 14d, 14e). Collectively, these findings indicate that galunisertib prevents increased cell death by inhibiting an inappropriate upregulation of the TGFβ signaling pathway in GLIS3$^{-/-}$ cells.

Discussion

In this disclosure, we describe a stepwise protocol that closely mimics pancreatic development, through generation of GLIS3-expressing late stage pancreatic progenitors that generate mono-hormonal glucose-responding β-like cells. The GSIS response of cells at D30_L is not indistinguishable from human primary islets. These late stage progenitors resemble second transition cells in mouse development. Our strategy incorporates limited manipulation of developmental pathways and serves thus far as an optimized protocol to model the pancreatic β-cell defects in human diabetes.

Using this "minimal component" differentiation strategy, we studied the role of GLIS3 in different stages of pancreatic differentiation. Our initial attempt using isogenic GLIS3$^{-/-}$ hESCs failed to recapitulate the defects observed in Glis3$^{-/-}$ mice (Zhu et al. Cell Stem Cell 18, 755-768 (2016)), which might be due to lack of GLIS3 expressing cells. Using our newly developed "minimal component" differentiation strategy, we found that loss of GLIS3 does not affect the induction of DE and PP1 cells. By quantification of different endocrine subtypes, we found that the percentage of INS$^+$ cells is significantly decreased in GLIS3$^{-/-}$ cells, also seen in Glis3$^{-/-}$ mice.

The present disclosure can be used for developing isogenic hESCs carrying disease-associated mutations to create a robust and disease-relevant platform for drug discovery. We used GLIS3$^{-/-}$ hESC-derived β-like cells to perform a screen using FDA approved drug and drugs in clinical trials. We discovered that galunisertib, a drug candidate in Phase II clinical trial, can effectively rescue cell death in GLIS3$^{-/-}$ β-like cells both in vitro and in vivo. More importantly, galunisertib does not affect wildtype cells, suggesting that the effect of galunisertib is specific to GLIS3$^{-/-}$ β-like cells. This disclosure has wide-ranging implications for the treatment of neonatal diabetes and broadens the scope of precision medicine for more complex conditions, including T1D and T2D.

Methods

Maintenance of hESCs. Human ESC lines $INS^{GFP/W}$ HES3, HUES8, and H1 were grown on Matrigel-coated 10 $cm^2$ plates in mTeSR1 medium (STEMCELL Technologies) supplemented with 50 µg $mL^{-1}$ Normocin (InvivoGen). Cells were maintained at 37 C with 5% $CO_2$. Cultures were passaged every 4-6 day at 1:15-1:20 with 0.5 mM EDTA. All lines were routinely tested for mycoplasma contamination. All hESC studies were approved by the Tri-Institutional Embryonic Stem Cell Research Committee (ESCRO).

In vitro differentiation of hESCs. To prepare for differentiation, hESCs were dissociated with 0.5 mM EDTA and plated on Matrigel-coated 6-well plates at a ratio of 1:1-1:2 resulting at ~95% starting confluency. The differentiation started 24-48 hr later. On day 0, cells were exposed to basal medium RPMI 1640 supplemented with 1× Glutamax (ThermoFisher Scientific), 50 µg $mL^{-1}$ Normocin, 100 ng $mL^{-1}$ Activin A (R&D), and 2 µM of CHIR99021 (GSK3β inhibitor 3, SelleckChem) for 24 hr. The medium was changed on day 1 to basal RPMI 1640 supplemented with 1× Glutamax (ThermoFisher Scientific), 50 µg $mL^{-1}$ Normocin, 0.2% fetal bovine serum (Corning), 100 ng $mL^{-1}$ Activin A (R&D) for 2 days. On day 3, the resulting definitive endoderm cells were cultured in basal RPMI 1640 supplemented with 1× Glutamax (ThermoFisher Scientific), 50 µg $mL^{-1}$ Normocin, 2% fetal bovine serum (Corning), 50 ng $mL^{-1}$ FGF7 (Peprotech) for 2 days to acquire foregut fate. On day 5, the cells were induced to differentiate to pancreatic endoderm in basal medium DMEM 4.5 g $L^{-1}$ glucose (Corning) supplemented with 1× Glutamax, 50 µg $mL^{-1}$ Normocin and 2% B27 (GIBCO), 2 µM retinoic acid (RA; Sigma), 200 nM LDN193189 (LDN, Stemgent) and 0.25 µM SANT-1 for four days (PP1). The medium was subsequently refreshed every other day. On day 9, this medium was further supplemented with 10 ng $mL^{-1}$ EGF (Peprotech) and 10 ng $mL^{-1}$ FGF2 to help maintain the cells at the pancreatic progenitor stage. In the case of the H1 line, cells were treated with 3 µM RA, 200 nM LDN, 0.25 µM SANT-1, 15 ng $mL^{-1}$ EGF and 15 ng $mL^{-1}$ FGF2 for a 14-day period. On day 23, the PP2 cells differentiate into late stage $INS^+$ PP2-β-like cells in basal differentiation medium including DMEM supplemented with 1× Glutamax, 50 µg $mL^{-1}$ Normocin, 2% B27 for 7 days (D30_L). For differentiation to PP1-β cells, PP1 cells on day 9 were cultured for 7 days in the basal differentiation medium (D16_E).

Generation of isogenic GLIS3 mutant lines. To mutate the human GLIS3 gene, two sgRNAs targeting exon three of the gene were designed and cloned into a vector carrying a CRISPR-Cas9 gene (Addgene plasmid #42230). The sgRNAs were validated using the surveyor assay in 293T cells. The construct containing validated sgRNA was then co-electroporated together with a vector expressing puromycin into dissociated $INS^{GFP/W}$ HES3 cells suspended in Human Stem Cell Nucleofector solution (Lonza) following the manufacturer's instructions. After replating, the electroporated cells were selected with 500 ng/ml puromycin. After 2 days of puromycin selection, hESCs were dissociated into single cells by Accutase (Innovative Cell Technologies) and replated at low density. The cells were supplemented with 10 µM Y-27632. After approximately 10 days, individual colonies were picked, mechanically disaggregated, and replated into two individual wells of 96-well plates. A portion of the cells was lysed and analyzed by Sanger sequencing. For biallelic frameshift mutants, we chose both homozygous mutants and compound heterozygous mutants. Wild-type clonal lines from the targeting experiment were included as wild-type controls to account for potential nonspecific effects associated with the gene-targeting process.

Immunofluorescence staining. Cells were fixed in 4% paraformaldehyde solution (Affymetrix) for 20 min, then blocked and permeabilized in PBS solution containing 5% horse serum and 0.3% Triton for 1 hr at room temperature. The cells were incubated with primary antibodies overnight at 4 C followed by 1 hr incubation with fluorescence-conjugated secondary antibodies (Alexafluor, ThermoFisher Scientific) at RT. For pSMAD2/3 staining, cells were permeabilized with ice-cold methanol at ~20 C for 10 min after fixation and prior to blocking. The following primary antibodies were used: anti-OCT4 (1:200, Santa Cruz), anti-SOX17 (1:500, R&D), anti-PDX1 (1:500, R&D), anti-SOX9 (1:1000, Millipore), anti-NKX6.1 (1:500, DSHB), anti-NKX2.2 (1:500, DSHB), anti-PAX6 (1:1000, Covance), anti-ISL1 (1:200, DSHB), anti-UCN3 (1:500, Phoenix Pharmaceuticals), anti-NGN3 (1:500, R&D), anti-chromogranin A (1:1000, Immunostar), anti-glucagon (1:2000, Sigma) anti-somatostatin (1:1000, DAKO), anti-ghrelin (1:500, Santa Cruz), anti-insulin (1:500, DAKO) and anti-cleaved caspase-3 (1:1000, BD Biosciences), anti-pSMAD2/3 (1:200, Cell Signaling).

Flow cytometry and Intracellular FACS analysis. hESC-derived cells were dissociated using Accutase. To analyze GFP expression, the cells were resuspended in PBS and used directly for analysis. For intracellular staining, the cells were fixed and stained using Foxp3 staining buffer set (eBiosciences) according to the manufacturer's instructions. Briefly, cells were first blocked with 2% horse serum for 15 min and then incubated with primary antibody for 45 min at RT, washed twice, incubated with fluorescence-conjugated secondary antibody for 30 min at 4C, washed twice and re-suspended in FACS buffer for analysis. The following primary antibodies were used: anti-SOX17 (1:500, R&D), anti-PDX1 (1:500, R&D), anti-pro-insulin (1:500, Millipore), anti-glucagon (1:100, Cell Signaling), anti-somatostatin (1:1000, DAKO), anti-ghrelin (1:500, Santa Cruz). Samples were analyzed with an Accuri C6 flow cytometry instrument and the data was processed using Flowjo v10 software.

Annexin V cellular apoptosis analysis. hESC derived cells were dissociated by Accutase and washed with cold PBS, stained with the PE/Annexin V apoptosis detection Kit (BD Bioscience, 559763) or A647-conjugated annexin V (Thermo Fisher Scientific) according to manufacturer's instructions, the samples were the analyzed by flow cytometry (BD Bioscience, FASC ARIA2) within 30 min. To include a positive control for apoptosis, cells were incubated with 10 µM Camptothecin (Sigma Aldrich) or DMSO for 4 hours prior to Annexin V staining.

Insulin secretion assays. Cells were starved in 2 ml glucose-free DMEM (with GlutaMax) for 3 hr followed by 1 hr incubation in KRBH buffer (with 0.1% BSA) in a 5% CO2/37 C incubator. To perform GSIS, cells were exposed sequentially to 400 µl of KRBH, 2 mM glucose, and 20 mM glucose; supernatants were collected after 30 min and spun down to eliminate the cells and debris. The same procedure was carried out for treatments with 30 mM KCl, 10 mM arginine (Sigma A5006), or 30 µM forskolin. Supernatants were used for ELISA (Human C-peptide ELISA kit, Millipore, EZHCP-20K). To measure the total c-peptide levels in each sample, cells were lysed in RIPA buffer supplemented with 1× protease inhibitor cocktail (ThermoFisher Scientific) for 3 hr at 4C. Lysates were spun down and supernatant was used for ELISA (Human C-peptide ELISA kit, Millipore, EZHCP-20K). C-peptide secretion from cells in each condition was normalized to KRBH treatment.

Insulin content measurement. Cells at D30_L were dissociated using Accutase and resuspended in DMEM containing 2% FBS and 1 mM EDTA. 20,000 INS-GFP$^+$ DAPI$^-$ cells were FACS sorted by an ARIA2 instrument, washed once with PBS and lysed in 200 μL RIPA buffer supplemented with 1× protease inhibitor cocktail (ThermoFisher Scientific). The Insulin content in the lysates was measured by ELISA (Human C-peptide ELISA kit, Millipore, EZHCP-20K).

Propium iodide cell viability staining. Cells at D30_L were dissociated using Accutase and replated onto 96-well plates coated with 804-G conditioned medium. Once attached, cells were stained by 2.5 μg mL$^{-1}$ propium iodide in DMEM for 12 min, washed once with DMEM and fixed with 4% paraformaldehyde for 20 min. DAPI was used to quantify total number of cells after fixation. Plates were analyzed using a Molecular Devices ImageXpress High-Content Analysis System. Data was quantified using MetaXpress software.

High throughput chemical screening. To perform the high throughput small molecule screening, GLIS3$^{-/-}$ cells at D26_L were dissociated using Accutase and replated onto 804G-coated 384-well plates at 20,000 cells/80 μl medium/well. After 8 hr, cells were treated at 1 μM and 10 μM with compounds from an in-house library of 300 signaling pathway modulators, an epigenetics library (Cayman Chemical), Prestwick library of approved drugs (FDA, EMA and other agencies), LOPAC (Sigma Aldrich) and the MicroSource library totaling 5000 chemicals. DMSO treatment was used as a negative control. Untreated wells containing WT cells were included as positive control. After 4 days of culture, cells were first stained with 2.5 μg/mL PI and then fixed and stained using antibodies against Insulin (DAKO) and cleaved caspase-3 (BD biosciences). Plates were analyzed using a Molecular Devices ImageXpress High-Content Analysis System. Two-dimensional analysis was used. Compounds inducing lower % cleaved caspase-3 (Z-score<−1.5) and a similar or higher number of INS$^+$ cells compared to DMSO treated wells were selected as primary hits.

Quantitative real-time PCR analysis. Total RNA was isolated using the Qiagen RNeasy Plus mini kit following manufacturer's instructions. First strand cDNA was generated using the Superscript III FirstStrand Synthesis System (ThermoFisher Scientific). First strand cDNA products were used as qPCR templates in SYBR Green-based qPCR using a Roche 480 Lightcycler. Triplicate reactions (technical replicates) were carried out for each biological replicate. ACTB was used as a housekeeping control to normalize target gene expression. Sequences of primers used are listed in Supplementary Table 2.

Purification of human I3-cells from islets for RNA-seq. Human islets were provided by the IIDP (Integrated Islet Distribution Program). Briefly, 10,000 islets from a healthy donor were partially disaggregated using 0.25% Trypsin/EDTA (Corning), resuspended in RPMI 1640 supplemented with 10% FBS, 1× GlutaMax, 100 U mL$^{-1}$ Penicillin/100 μg mL$^{-1}$ Streptomycin (GIBCO) and infected with an insulin reporter adenovirus construct pAd-RIP-Zsgreen. 4 days later, the cells were dissociated with 0.25% Trypsin/EDTA. Zsgreen$^+$ DAPI$^-$ cells were FACS sorted directly into Trizol LS (ThermoFisher Scientific). RNA was extracted according to the manufacturer's instructions.

RNA-seq. Sample QC analysis, cDNA library synthesis and RNA sequencing were carried out by the Weill Cornell Genomics Core. In brief, the quality of RNA samples was examined by Agilent bioanalyzer (Agilent). cDNA libraries were generated using TruSeq RNA Sample Preparation (Illumina). Each library was sequenced using single-reads in HiSeq4000 (Illumina). Gene expression levels were analyzed using Cufflinks.

Bioinformatics analysis. To generate a heatmap plot on three or more samples, the expression values were normalized per gene over all samples. For each gene we calculated the mean and standard deviation (stdev) of expression over all samples, and linearly transformed the expression value using the formula (RPKM-mean)/stdev. The heatmaps were then generated using heatmap.2 in the R gplots package. Gene set enrichment analysis (GSEA) was performed using GSEA software (Broad Institute). To compare PP1-β and PP2-β cells with adult β-cells, gene sets listing the top 1000 genes differentially expressed between PP1-β and adult β-cells were used (UP for genes higher expressed and DN for genes lower expressed in adult β-cells). To create a gene set to analyze the endocrine gene expression signature in WT and GLIS3$^{-/-}$ PP2 cells, genes enriched in NGN3-GFP$^+$ cells from e15.5 mouse pancreas were used (discovery-.lifemapsc.com/in-vivo-development/pancreas/dorsal-pancreatic-bud/endocrine-progenitor-cells). Gene Ontology (GO) and KEGG pathway analysis on up/down-regulated genes in WT and GLIS3$^{-/-}$ cells were performed using DAVID v6.8 functional annotation tool (https://david.ncifcrf.gov/). Pathways prediction with Ingenuity Pathway Analysis (IPA, QIAGEN Bioinformatics) was carried out using as the input genes up/downregulated≥two-fold in WT and GLIS3$^{-/-}$ GFP$^+$ PP2-β cells.

In vivo transplantation and drug treatment. WT and isogenic mutant hESCs at day 24 of differentiation (around 1 million cells) were harvested by cell scraper, mixed with 20 μl Matrigel (Corning) and transplanted under the kidney capsule of 6-8 weeks old male SCID-beige mice. For drug treatment, mice were injected intraperitoneally with 15 mg/kg/day galunisertib or vehicle for seven days. To prepare the injection cocktail, 200 mM galunisertib in DMSO was diluted ~15 times with a 50:50 mixture of PEG300 (Sigma Aldrich) and saline (APP Pharmaceuticals). All animal work was conducted in agreement with NIH guidelines and approved by the local Institutional Animal Care and Use Committee (IACUC), the Institutional Biosafety Committee (IBC) as well as the Embryonic Stem Cell Research Committee (ESCRO).

Immunohistochemistry. Mouse kidneys with cells grafted under the capsules were washed with PBS, fixed with 4% paraformaldehyde at 4C overnight and transferred to 30% sucrose solution for dehydration. The tissues were embedded in a 2:1 mixture of OCT: 30% sucrose and sectioned using a cryostat microtome. The slides were blocked and permeabilized in PBS solution containing 5% horse serum and 0.3% Triton for 1 hr at RT and then incubated with primary antibodies overnight at 4C followed by 1 hr incubation with fluorescence-conjugated secondary antibodies (Alexafluor, ThermoFisher Scientific) at RT. The following primary antibodies were used: anti-PDX1 (1:500, R&D), anti-insulin (1:500, DAKO) and anti-cleaved caspase-3 (1:1000, BD Biosciences) and anti-STEM121 (1:1000, Stem Cells Inc.). Fluorescent images were scored using Meta-Morph® image analysis software (Molecular Devices).

Western blot analysis. Whole-cell lysates were generated by scraping cultures on day 24 of differentiation in cold PBS, and re-suspending in complete lysis buffer (20 mM Tris pH 7.0, 150 mM NaCl, 50 mM NaF, 1% NP-40 substitute, and Thermo Scientific HALT protease inhibitor cocktail 1:100). Lysates were loaded onto 10% NuPage Bis-Tris gels (Invitrogen), resolved by electrophoresis, and transferred to PVDF membranes (Bio-Rad). Membranes were blocked with 5% bovine serum albumin in TBS+ 0.05% Tween and probed overnight with primary antibody. The antibodies were rabbit anti-phospho-SMAD2/3 (1:250, Cell Signaling), rabbit anti-SMAD2/3 XP (1:5000, Cell Signaling), and mouse anti-β-actin (1:50000, Sigma A1978). Membranes were washed and incubated for 1 hr with HRP-conjugated secondary antibody (Bio-Rad) in 5% milk-TBS-0.05% Tween and developed using SuperSignal West Pico (Thermo Scientific) or Immobilon (Millipore) ECL substrate.

Statistical Analysis. Data are presented as mean±SEM derived from at least three independent biological replicates. Data on biological replicates (n) and the type of statistical test are described in the figure legends. Statistical analysis was performed using GraphPad Prism 6 software. P values by unpaired two-tailed t-test were *P<0.05, P<0.01, *P<0.001, ****P<0.0001. n. s. not significant.

While the present invention has been described through various specific embodiments, routine modification to these embodiments will be apparent to those skilled in the art, which modifications are intended to be included within the scope of this disclosure.

What is claimed is:

1. A method of generating an enriched population of monohormonal cells from pluripotent stem cells comprising the following steps exposing pluripotent stem cells sequentially to:
   a) a basal medium supplemented with at least CHIR99021 and Activin A;
   b) a basal medium supplemented with Activin A;
   c) a basal medium supplemented with at least FGF7;
   d) a basal medium supplemented with retinoic acid, LDN 193189, and SANT1;
   e) a basal medium supplemented with components consisting of 2 µM retinoic acid, 200 nM LDN193189, 0.25 UM SANT1, 10 ng/ml EGF and 10 ng/ml FGF2; and
   f) a basal differentiation medium,
   wherein step a is carried out for 1 day, step b is carried out for 2 days, step c is carried out for 2 days, step d is carried out for 4 days, step e is carried out for 14 days and step f is carried out for 7 days; and
   wherein at least 90% of the cells in the resulting population are monohormonal and express insulin, but not glucagon, somatostatin, or ghrelin and are Glis3+.

2. The method of claim 1, wherein the cells after step e express NKX6.1 and NEUROD1 at levels higher than the cells after step d.

3. The method of claim 1, wherein the enriched population after step f has all of the following features:
   a) at least 95% of the cells express PDX1;
   b) at least 95% of the cells NKX2.2;
   c) at least 85% of the cells express PAX6;
   d) at least 90% of the cells express ISL1;
   e) at least 50% of the cells express NKK6.1; and
   f) at least 60% of the cells express UCN3.

4. The method of claim 1, wherein the pluripotent stem cells are human pluripotent stem cells.

* * * * *